United States Patent
Valton et al.

(10) Patent No.: US 10,813,951 B2
(45) Date of Patent: Oct. 27, 2020

(54) METHOD OF ENGINEERING CHEMOTHERAPY DRUG RESISTANT T-CELLS FOR IMMUNOTHERAPY

(71) Applicant: CELLECTIS, Paris (FR)

(72) Inventors: Julien Valton, New York, NY (US); Philippe Duchateau, Draveil (FR); David Sourdive, Levallois-Perret (FR)

(73) Assignee: CELLECTIS, Paris (FR)

( * ) Notice: Subject to any disclaimer, the term of this patent is extended or adjusted under 35 U.S.C. 154(b) by 713 days.

(21) Appl. No.: 15/037,988

(22) PCT Filed: Nov. 21, 2014

(86) PCT No.: PCT/EP2014/075317
§ 371 (c)(1),
(2) Date: May 19, 2016

(87) PCT Pub. No.: WO2015/075195
PCT Pub. Date: May 28, 2015

(65) Prior Publication Data
US 2016/0361359 A1 Dec. 15, 2016

Related U.S. Application Data

(60) Provisional application No. 61/907,874, filed on Nov. 22, 2013.

(30) Foreign Application Priority Data

Jun. 17, 2014 (DK) .................................. 201470362

(51) Int. Cl.
*A61K 35/17* (2015.01)
*C12N 5/0783* (2010.01)
*A61K 45/06* (2006.01)
*A61K 31/7076* (2006.01)

(52) U.S. Cl.
CPC .......... *A61K 35/17* (2013.01); *A61K 31/7076* (2013.01); *A61K 45/06* (2013.01); *C12N 5/0636* (2013.01); *A61K 2300/00* (2013.01); *C12N 2510/00* (2013.01)

(58) Field of Classification Search
None
See application file for complete search history.

(56) References Cited

FOREIGN PATENT DOCUMENTS

| WO | 2011/053750 A2 | 5/2011 |
| WO | 2013/176915 A1 | 11/2013 |

OTHER PUBLICATIONS

Valton et al, Mol. Therapy, 2015, pp. 1507-1518.*
Toy et al, PNAS, 2010, pp. 5551-5556.*

Jensen M C et al: "Antitransgene Rejection Responses Contribute to Attenuated Persistence of Adoptively Transferred CD20/CD19-Specific Chimeric Antigen Receptor Redirected T Cells in Humans", Biology of Blood and Marrow Transplantation, Kluge Carden Jennings Publishing, Charlottesville, VA, US, vol. 16, No. 9, Sep. 1, 2010 (Sep. 1, 2010), pp. 1245-1256.

Falta et al: "Azathioprine Associated T-Cell Mutations in Insulin-Dependent Diabetes Mellitus", Scandinavian Journal of Immunology, Jun. 1, 2000 (Jun. 1, 2000), pp. 626-633.

Laurent Poirot et al: HT-Cell Engineering 1-32 For "off-The-shelf" Adoptive Immunotherapy, Blood Journal: 122, Nov. 15, 2013 (Nov. 15, 2013).

Emma Mansson et al: "Down-regulation of deoxycytidine kinase in human leukemic cell lines resistant to cladribine and clofarabine and increased ribonucleotide reductase activity contributes to fludarabine resistance", Biochemical Pharmacology, vol. 65, No. 2, Jan. 1, 2003 (Jan. 1, 2003), pp. 237-247.

Lawrences. Lamb et al: "Engineered Drug Resistant [gamma][delta] T Cells Kill Glioblastoma Cell Lines during a Chemotherapy Challenge: A Strategy for Combining Chemo- and Immunotherapy", PLOSONE, vol. 8, No. 1, Jan. 11, 2013 (Jan. 11, 2013), p. e51805.

Anindya Dasgupta et al: "Treatment of a Solid Tumor Using Engineered Drug-Resistant Immunocompetent Cells and Cytotoxic Chemotherapy", Humangene Therapy, vol. 23, No. 7, Jul. 1, 2012 (Jul. 1, 2012), pp. 711-721.

Chottiner et al., Cloning and expression of human deoxycytidine kinase cDNA, Proc. Natl. Acad. Sci. USA vol. 88, pp. 1531-1535, Feb. 1991.

Takeuchi et al., Redesign of extensive protein—DNA interfaces of meganucleases using iterative cycles of in vitro compartmentalization, Proc. Natl. Acad. Sci. USA vol. 111 pp. 14061-14066, Mar. 2014.

(Continued)

*Primary Examiner* — Michael D Burkhart
(74) *Attorney, Agent, or Firm* — Arrigo, Lee, Guttman & Mouta-Bellum LLP

(57) ABSTRACT

The present invention relates to the use of "off-the-shelf" allogeneic therapeutic cells for immunotherapy in conjunction with chemotherapy to treat patients with cancer. In particular, the inventors develop a method of engineering allogeneic T-cell resistant to chemotherapeutic agents. The therapeutic benefits afforded by this strategy should be enhanced by the synergistic effects between chemotherapy and immunotherapy. In particular, the present invention relates to a method for modifying T-cells by inactivating at least one gene encoding T-cell receptor component and by modifying said T-cells to confer drug resistance. The invention opens the way to standard and affordable adoptive immunotherapy strategies for treating cancer.

17 Claims, 29 Drawing Sheets

Specification includes a Sequence Listing.

(56) References Cited

OTHER PUBLICATIONS

Wilson et al., Expanding the Repertoire of Target Sites for Zinc Finger Nuclease-mediated Genome Modification, Molecular Therapy—Nucleic Acids (2013) 2, e8.
Ran et al., Genome engineering using the CRISPR-Cas9 system, Nat Protoc. Nov. 2013; 8(11): 2281-2308.

* cited by examiner

T7 assay (D4)

SEQUENCE LISTING

```
<160> NUMBER OF SEQ ID NOS: 79

<210> SEQ ID NO 1
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within T cell receptor alpha
      chain gene (TRAC_T01)

<400> SEQUENCE: 1
ttgtcccaca gatatccaga accctgaccc tgccgtgtac cagctgaga          49

<210> SEQ ID NO 2
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within T cell receptor alpha
      chain gene (TRAC_T02)

<400> SEQUENCE: 2
```
tttagaaagt tcctgtgatg tcaagctggt cgagaaaagc tttgaaaca          49

<210> SEQ ID NO 3
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within T cell receptor alpha
      chain gene (TRAC_T03)

<400> SEQUENCE: 3
tccagtgaca agtctgtctg cctattcacc gattttgatt ctcaaacaa          49

<210> SEQ ID NO 4
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within T cell receptor alpha
      chain gene (TRAC_T04)

<400> SEQUENCE: 4
tatatcacag acaaaactgt gctagacatg aggtctatgg acttcaaga          49

<210> SEQ ID NO 5
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within T cell receptor alpha
      chain gene (TRAC_T05)

<400> SEQUENCE: 5
tgaggtctat ggacttcaag agcaacagtg ctgtggcctg gagcaacaa          49

<210> SEQ ID NO 6
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within T cell receptor beta
      chain gene (TRBC_T01)

<400> SEQUENCE: 6
tgtgtttgag ccatcagaag cagagatctc ccacacccaa aaggccaca          49

<210> SEQ ID NO 7
<211> LENGTH: 50
<212> TYPE: DNA
<213> ORGANISM: Homo sapiens
<220> FEATURE:
<221> NAME/KEY: misc_feature
<223> OTHER INFORMATION: Target sequence within T cell receptor beta
      chain gene (TRBC_T02)

<400> SEQUENCE: 7
ttcccacccg aggtcgctgt gtttgagcca tcagaagcag agatctccca          50

<210> SEQ ID NO 8
<211> LENGTH: 530
<212> TYPE: PRT
<213> ORGANISM: Artificial sequence
<220> FEATURE:
<223> OTHER INFORMATION: synthetic polypeptide: Repeat TRAC_T01-L

<400> SEQUENCE: 8

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
        210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
            275                 280                 285

Gln Ala Leu Glu Thr Val Gln Ala Leu Leu Pro Val Leu Cys Gln Ala
        290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Val Ala Ile Ala
        370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala

```
                    405                 410                 415
Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 9
<211> LENGTH: 530
<212> TYPE: PRT
<213> ORGANISM: Artificial sequence
<220> FEATURE:
<223> OTHER INFORMATION: synthetic polypeptide: Repeat TRAC_T01-R

<400> SEQUENCE: 9

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
```

```
                225                 230                 235                 240
Pro Gln Gln Val Val Ala Ile Ala Ser Asn Asn Gly Gly Lys Gln Ala
                    245                 250                 255
Leu Glu Thr Val Gln Arg Leu Leu Pro Val Leu Cys Gln Ala His Gly
                260                 265                 270
Leu Thr Pro Gln Gln Val Val Ala Ile Ala Ser Asn Asn Gly Gly Lys
            275                 280                 285
Gln Ala Leu Glu Thr Val Gln Arg Leu Leu Pro Val Leu Cys Gln Ala
        290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                    325                 330                 335
Gln Ala His Gly Leu Thr Pro Glu Gln Val Val Ala Ile Ala Ser Asn
                340                 345                 350
Ile Gly Gly Lys Gln Ala Leu Glu Thr Val Gln Ala Leu Leu Pro Val
            355                 360                 365
Leu Cys Gln Ala His Gly Leu Thr Pro Glu Gln Val Val Ala Ile Ala
        370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                    405                 410                 415
Ile Ala Ser Asn Ile Gly Gly Lys Gln Ala Leu Glu Thr Val Gln Ala
                420                 425                 430
Leu Leu Pro Val Leu Cys Gln Ala His Gly Leu Thr Pro Glu Gln Val
            435                 440                 445
Val Ala Ile Ala Ser His Asp Gly Gly Lys Gln Ala Leu Glu Thr Val
        450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
                    485                 490                 495
Thr Val Gln Arg Leu Leu Pro Val Leu Cys Gln Ala His Gly Leu Thr
                500                 505                 510
Pro Gln Gln Val Val Ala Ile Ala Ser Asn Gly Gly Gly Arg Pro Ala
            515                 520                 525
Leu Glu
    530

<210> SEQ ID NO 10
<211> LENGTH: 530
<212> TYPE: PRT
<213> ORGANISM: Artificial sequence
<220> FEATURE:
<223> OTHER INFORMATION: synthetic polypeptide: Repeat TRBC_T01-L

<400> SEQUENCE: 10

Leu Thr Pro Gln Gln Val Val Ala Ile Ala Ser Asn Asn Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Gln Gln Val Val Ala Ile Ala Ser Asn Gly Gly
            35                  40                  45
Gly Lys Gln Ala Leu Glu Thr Val Gln Arg Leu Leu Pro Val Leu Cys
```

```
                50                  55                  60
Gln Ala His Gly Leu Thr Pro Gln Gln Val Val Ala Ile Ala Ser Asn
 65                  70                  75                  80

Asn Gly Gly Lys Gln Ala Leu Glu Thr Val Gln Arg Leu Leu Pro Val
                 85                  90                  95

Leu Cys Gln Ala His Gly Leu Thr Pro Gln Gln Val Val Ala Ile Ala
                100                 105                 110

Ser Asn Gly Gly Lys Gln Ala Leu Glu Thr Val Gln Arg Leu Leu
                115                 120                 125

Pro Val Leu Cys Gln Ala His Gly Leu Thr Pro Gln Gln Val Val Ala
                130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
                180                 185                 190

Gln Arg Leu Leu Pro Val Leu Cys Gln Ala His Gly Leu Thr Pro Gln
                195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Asn Gly Gly Lys
                275                 280                 285

Gln Ala Leu Glu Thr Val Gln Arg Leu Leu Pro Val Leu Cys Gln Ala
                290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
                340                 345                 350

Asp Gly Gly Lys Gln Ala Leu Glu Thr Val Gln Arg Leu Leu Pro Val
                355                 360                 365

Leu Cys Gln Ala His Gly Leu Thr Pro Glu Gln Val Val Ala Ile Ala
                370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
                420                 425                 430

Leu Leu Pro Val Leu Cys Gln Ala His Gly Leu Thr Pro Glu Gln Val
                435                 440                 445

Val Ala Ile Ala Ser His Asp Gly Gly Lys Gln Ala Leu Glu Thr Val
                450                 455                 460

Gln Arg Leu Leu Pro Val Leu Cys Gln Ala His Gly Leu Thr Pro Glu
465                 470                 475                 480
```

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 11
<211> LENGTH: 530
<212> TYPE: PRT
<213> ORGANISM: Artificial sequence
<220> FEATURE:
<223> OTHER INFORMATION: synthetic polypeptide: Repeat TRBC_T01-R

<400> SEQUENCE: 11

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
        340                 345                 350

Asn Gly Gly Lys Gln Ala Leu Glu Thr Val Gln Arg Leu Leu Pro Val
    355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Asn Gly Gly Lys Gln Ala Leu Glu Thr Val Gln Arg
        420                 425                 430

Leu Leu Pro Val Leu Cys Gln Ala His Gly Leu Thr Pro Gln Gln Val
    435                 440                 445

Val Ala Ile Ala Ser Asn Gly Gly Lys Gln Ala Leu Glu Thr Val
450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
    515                 520                 525

Leu Glu
    530

<210> SEQ ID NO 12
<211> LENGTH: 530
<212> TYPE: PRT
<213> ORGANISM: Artificial sequence
<220> FEATURE:
<223> OTHER INFORMATION: synthetic polypeptide: Repeat TRBC_T02-L

<400> SEQUENCE: 12

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
        100                 105                 110

Ser Asn Ile Gly Gly Lys Gln Ala Leu Glu Thr Val Gln Ala Leu Leu
    115                 120                 125

```
Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

```
<210> SEQ ID NO 13
<211> LENGTH: 530
<212> TYPE: PRT
<213> ORGANISM: Artificial sequence
<220> FEATURE:
<223> OTHER INFORMATION: synthetic polypeptide: Repeat TRBC_T02-R

<400> SEQUENCE: 13

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365
```

```
Leu Cys Gln Ala His Gly Leu Thr Pro Gln Gln Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 14
<211> LENGTH: 186
<212> TYPE: PRT
<213> ORGANISM: homo sapiens
<220> FEATURE:
<221> NAME/KEY: misc_feature
<223> OTHER INFORMATION: Dihydrofolate reductase protein

<400> SEQUENCE: 14

Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Tyr Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

-continued

```
<210> SEQ ID NO 15
<211> LENGTH: 514
<212> TYPE: PRT
<213> ORGANISM: homo sapiens
<220> FEATURE:
<221> NAME/KEY: MISC_FEATURE
<223> OTHER INFORMATION: inosine-5'-monophosphate dehydrogenase 2

<400> SEQUENCE: 15

Met Ala Asp Tyr Leu Ile Ser Gly Gly Thr Ser Tyr Val Pro Asp Asp
1               5                   10                  15

Gly Leu Thr Ala Gln Gln Leu Phe Asn Cys Gly Asp Gly Leu Thr Tyr
            20                  25                  30

Asn Asp Phe Leu Ile Leu Pro Gly Tyr Ile Asp Phe Thr Ala Asp Gln
        35                  40                  45

Val Asp Leu Thr Ser Ala Leu Thr Lys Lys Ile Thr Leu Lys Thr Pro
    50                  55                  60

Leu Val Ser Ser Pro Met Asp Thr Val Thr Glu Ala Gly Met Ala Ile
65                  70                  75                  80

Ala Met Ala Leu Thr Gly Gly Ile Gly Phe Ile His His Asn Cys Thr
                85                  90                  95

Pro Glu Phe Gln Ala Asn Glu Val Arg Lys Val Lys Lys Tyr Glu Gln
            100                 105                 110

Gly Phe Ile Thr Asp Pro Val Val Leu Ser Pro Lys Asp Arg Val Arg
        115                 120                 125

Asp Val Phe Glu Ala Lys Ala Arg His Gly Phe Cys Gly Ile Pro Ile
    130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu Glu His Asp Cys Phe Leu Glu
                165                 170                 175

Glu Ile Met Thr Lys Arg Glu Asp Leu Val Val Ala Pro Ala Gly Ile
            180                 185                 190

Thr Leu Lys Glu Ala Asn Glu Ile Leu Gln Arg Ser Lys Lys Gly Lys
        195                 200                 205

Leu Pro Ile Val Asn Glu Asp Asp Glu Leu Val Ala Ile Ile Ala Arg
    210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
                245                 250                 255

Lys Tyr Arg Leu Asp Leu Leu Ala Gln Ala Gly Val Asp Val Val Val
            260                 265                 270

Leu Asp Ser Ser Gln Gly Asn Ser Ile Phe Gln Ile Asn Met Ile Lys
        275                 280                 285

Tyr Ile Lys Asp Lys Tyr Pro Asn Leu Gln Val Ile Gly Gly Asn Val
    290                 295                 300

Val Thr Ala Ala Gln Ala Lys Asn Leu Ile Asp Ala Gly Val Asp Ala
305                 310                 315                 320

Leu Arg Val Gly Met Gly Ser Gly Ser Ile Cys Ile Thr Gln Glu Val
                325                 330                 335

Leu Ala Cys Gly Arg Pro Gln Ala Thr Ala Val Tyr Lys Val Ser Glu
            340                 345                 350

Tyr Ala Arg Arg Phe Gly Val Pro Val Ile Ala Asp Gly Gly Ile Gln
```

```
                    355                 360                 365

Asn Val Gly His Ile Ala Lys Ala Leu Ala Leu Gly Ala Ser Thr Val
        370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
                405                 410                 415

Leu Asp Ala Met Asp Lys His Leu Ser Ser Gln Asn Arg Tyr Phe Ser
            420                 425                 430

Glu Ala Asp Lys Ile Lys Val Ala Gln Gly Val Ser Gly Ala Val Gln
        435                 440                 445

Asp Lys Gly Ser Ile His Lys Phe Val Pro Tyr Leu Ile Ala Gly Ile
    450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
                485                 490                 495

Ala Gln Val Glu Gly Gly Val His Ser Leu His Ser Tyr Glu Lys Arg
            500                 505                 510

Leu Phe

<210> SEQ ID NO 16
<211> LENGTH: 521
<212> TYPE: PRT
<213> ORGANISM: Artificial sequence
<220> FEATURE:
<223> OTHER INFORMATION: Synthetic construct: Calcineurin A

<400> SEQUENCE: 16

Met Ser Glu Pro Lys Ala Ile Asp Pro Lys Leu Ser Thr Thr Asp Arg
1               5                   10                  15

Val Val Lys Ala Val Pro Phe Pro Pro Ser His Arg Leu Thr Ala Lys
            20                  25                  30

Glu Val Phe Asp Asn Asp Gly Lys Pro Arg Val Asp Ile Leu Lys Ala
        35                  40                  45

His Leu Met Lys Glu Gly Arg Leu Glu Glu Ser Val Ala Leu Arg Ile
    50                  55                  60

Ile Thr Glu Gly Ala Ser Ile Leu Arg Gln Glu Lys Asn Leu Leu Asp
65                  70                  75                  80

Ile Asp Ala Pro Val Thr Val Cys Gly Asp Ile His Gly Gln Phe Phe
                85                  90                  95

Asp Leu Met Lys Leu Phe Glu Val Gly Gly Ser Pro Ala Asn Thr Arg
            100                 105                 110

Tyr Leu Phe Leu Gly Asp Tyr Val Asp Arg Gly Tyr Phe Ser Ile Glu
        115                 120                 125

Cys Val Leu Tyr Leu Trp Ala Leu Lys Ile Leu Tyr Pro Lys Thr Leu
    130                 135                 140

Phe Leu Leu Arg Gly Asn His Glu Cys Arg His Leu Thr Glu Tyr Phe
145                 150                 155                 160

Thr Phe Lys Gln Glu Cys Lys Ile Lys Tyr Ser Glu Arg Val Tyr Asp
                165                 170                 175

Ala Cys Met Asp Ala Phe Asp Cys Leu Pro Leu Ala Ala Leu Met Asn
            180                 185                 190

Gln Gln Phe Leu Cys Val His Gly Gly Leu Ser Pro Glu Ile Asn Thr
        195                 200                 205
```

```
Leu Asp Asp Ile Arg Lys Leu Asp Arg Phe Lys Glu Pro Pro Ala Tyr
210                 215                 220

Gly Pro Met Cys Asp Ile Leu Trp Ser Asp Pro Leu Glu Asp Phe Gly
225                 230                 235                 240

Asn Glu Lys Thr Gln Glu His Phe Thr His Asn Thr Val Arg Gly Cys
                245                 250                 255

Ser Tyr Phe Tyr Ser Tyr Pro Ala Val Cys Glu Phe Leu Gln His Asn
                260                 265                 270

Asn Leu Leu Ser Ile Leu Arg Ala His Glu Ala Gln Asp Ala Gly Tyr
            275                 280                 285

Arg Met Tyr Arg Lys Ser Gln Thr Thr Gly Phe Pro Ser Leu Ile Thr
290                 295                 300

Ile Phe Ser Ala Pro Asn Tyr Leu Asp Val Tyr Asn Asn Lys Ala Ala
305                 310                 315                 320

Val Leu Lys Tyr Glu Asn Asn Val Met Asn Ile Arg Gln Phe Asn Cys
                325                 330                 335

Ser Pro His Pro Tyr Trp Leu Pro Asn Phe Met Asp Val Phe Thr Trp
                340                 345                 350

Ser Leu Pro Phe Val Gly Glu Lys Val Thr Glu Met Leu Val Asn Val
            355                 360                 365

Leu Asn Ile Cys Ser Asp Asp Glu Leu Gly Ser Glu Glu Asp Gly Phe
370                 375                 380

Asp Gly Ala Thr Ala Ala Ala Arg Lys Glu Val Ile Arg Asn Lys Ile
385                 390                 395                 400

Arg Ala Ile Gly Lys Met Ala Arg Val Phe Ser Val Leu Arg Glu Glu
                405                 410                 415

Ser Glu Ser Val Leu Thr Leu Lys Gly Leu Thr Pro Thr Gly Met Leu
                420                 425                 430

Pro Ser Gly Val Leu Ser Gly Gly Lys Gln Thr Leu Gln Ser Ala Thr
            435                 440                 445

Val Glu Ala Ile Glu Ala Asp Glu Ala Ile Lys Gly Phe Ser Pro Gln
450                 455                 460

His Lys Ile Thr Ser Phe Glu Glu Ala Lys Gly Leu Asp Arg Ile Asn
465                 470                 475                 480

Glu Arg Met Pro Pro Arg Arg Asp Ala Met Pro Ser Asp Ala Asn Leu
                485                 490                 495

Asn Ser Ile Asn Lys Ala Leu Thr Ser Glu Thr Asn Gly Thr Asp Ser
            500                 505                 510

Asn Gly Ser Asn Ser Ser Asn Ile Gln
        515                 520
```

<210> SEQ ID NO 17
<211> LENGTH: 170
<212> TYPE: PRT
<213> ORGANISM: Artificial sequence
<220> FEATURE:
<223> OTHER INFORMATION: Synthetic construct: Calcineurin B

<400> SEQUENCE: 17

```
Met Gly Asn Glu Ala Ser Tyr Pro Leu Glu Met Cys Ser His Phe Asp
1               5                   10                  15

Ala Asp Glu Ile Lys Arg Leu Gly Lys Arg Phe Lys Lys Leu Asp Leu
                20                  25                  30

Asp Asn Ser Gly Ser Leu Ser Val Glu Glu Phe Met Ser Leu Pro Glu
            35                  40                  45
```

```
Leu Gln Gln Asn Pro Leu Val Gln Arg Val Ile Asp Ile Phe Asp Thr
        50                  55                  60

Asp Gly Asn Gly Glu Val Asp Phe Lys Glu Phe Ile Glu Gly Val Ser
65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
            100                 105                 110

Phe Gln Val Leu Lys Met Met Val Gly Asn Asn Leu Lys Asp Thr Gln
        115                 120                 125

Leu Gln Gln Ile Val Asp Lys Thr Ile Ile Asn Ala Asp Lys Asp Gly
    130                 135                 140

Asp Gly Arg Ile Ser Phe Glu Glu Phe Cys Ala Val Val Gly Gly Leu
145                 150                 155                 160

Asp Ile His Lys Lys Met Val Val Asp Val
                165                 170

<210> SEQ ID NO 18
<211> LENGTH: 207
<212> TYPE: PRT
<213> ORGANISM: homo sapiens
<220> FEATURE:
<221> NAME/KEY: MISC_FEATURE
<223> OTHER INFORMATION: Alkyl guanine transferase

<400> SEQUENCE: 18

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Pro Ile Leu Ile Pro
    130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205

<210> SEQ ID NO 19
<211> LENGTH: 495
<212> TYPE: PRT
```

<213> ORGANISM: artificial sequence
<220> FEATURE:
<223> OTHER INFORMATION: synthetic polypeptide: 4G7-CAR version 1

<400> SEQUENCE: 19

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
                245                 250                 255

Pro Phe Thr Phe Gly Ala Gly Thr Lys Leu Glu Leu Lys Arg Ala Asp
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
```

```
                385                 390                 395                 400
Asn Gln Leu Tyr Asn Glu Leu Asn Leu Gly Arg Arg Glu Glu Tyr Asp
                    405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 20
<211> LENGTH: 495
<212> TYPE: PRT
<213> ORGANISM: artificial sequence
<220> FEATURE:
<223> OTHER INFORMATION: synthetic polypeptide:4G7-CAR version 2

<400> SEQUENCE: 20

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
                20                  25                  30

Lys Pro Gly Ala Ser Val Lys Met Ser Cys Lys Ala Ser Gly Tyr Thr
            35                  40                  45

Phe Thr Ser Tyr Val Met His Trp Val Lys Gln Lys Pro Gly Gln Gly
        50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
                100                 105                 110

Val Tyr Tyr Cys Ala Arg Gly Thr Tyr Tyr Tyr Gly Ser Arg Val Phe
            115                 120                 125

Asp Tyr Trp Gly Gln Gly Thr Thr Leu Thr Val Ser Ser Gly Gly Gly
        130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
                180                 185                 190

Tyr Leu Tyr Trp Phe Leu Gln Arg Pro Gly Gln Ser Pro Gln Leu Leu
            195                 200                 205

Ile Tyr Arg Met Ser Asn Leu Ala Ser Gly Val Pro Asp Arg Phe Ser
        210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
```

Thr Thr Thr Pro Ala Pro Arg Pro Pro Thr Pro Ala Pro Thr Ile Ala
            260                 265                 270
                275                 280                 285

Ser Gln Pro Leu Ser Leu Arg Pro Glu Ala Cys Arg Pro Ala Ala Gly
                290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
                355                 360                 365

Cys Ser Cys Arg Phe Pro Glu Glu Glu Glu Gly Gly Cys Glu Leu Arg
                370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Leu Tyr Asn Glu Leu Gln Lys Asp
                435                 440                 445

Lys Met Ala Glu Ala Tyr Ser Glu Ile Gly Met Lys Gly Glu Arg Arg
                450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 21
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within CTLA4 gene

<400> SEQUENCE: 21
tggccctgca ctctcctgtt ttttcttctc ttcatccctg tcttctgca                49

<210> SEQ ID NO 22
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within CTLA4 gene

<400> SEQUENCE: 22
ttttccatgc tagcaatgca cgtggcccag cctgctgtgg tactggcca                49

<210> SEQ ID NO 23
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within CTLA4 gene

```
<400> SEQUENCE: 23
tccatgctag caatgcacgt ggcccagcct gctgtggtac tggccagca         49

<210> SEQ ID NO 24
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within PDCD1 gene

<400> SEQUENCE: 24
ttctccccag ccctgctcgt ggtgaccgaa ggggacaacg ccaccttca         49

<210> SEQ ID NO 25
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within PDCD1 gene

<400> SEQUENCE: 25
tacctctgtg gggccatctc cctggccccc aaggcgcaga tcaaagaga         49

<210> SEQ ID NO 26
<211> LENGTH: 530
<212> TYPE: PRT
<213> ORGANISM: Artificial sequence
<220> FEATURE:
<223> OTHER INFORMATION: Synthetic polypeptide: Repeat CTLA4_T01L

<400> SEQUENCE: 26
```

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

```
Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 27
<211> LENGTH: 530
<212> TYPE: PRT
<213> ORGANISM: Artificial sequence
<220> FEATURE:
<223> OTHER INFORMATION: Synthetic polypeptide: Repeat CTLA4_T01R

<400> SEQUENCE: 27

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30
```

-continued

```
His Gly Leu Thr Pro Glu Gln Val Ala Ile Ala Ser His Asp Gly
         35                  40                  45
Gly Lys Gln Ala Leu Glu Thr Val Gln Arg Leu Leu Pro Val Leu Cys
 50                  55                  60
Gln Ala His Gly Leu Thr Pro Glu Gln Val Val Ala Ile Ala Ser Asn
 65                  70                  75                  80
Ile Gly Gly Lys Gln Ala Leu Glu Thr Val Gln Ala Leu Leu Pro Val
                 85                  90                  95
Leu Cys Gln Ala His Gly Leu Thr Pro Gln Gln Val Val Ala Ile Ala
             100                 105                 110
Ser Asn Asn Gly Gly Lys Gln Ala Leu Glu Thr Val Gln Arg Leu Leu
             115                 120                 125
Pro Val Leu Cys Gln Ala His Gly Leu Thr Pro Glu Gln Val Val Ala
         130                 135                 140
Ile Ala Ser Asn Ile Gly Gly Lys Gln Ala Leu Glu Thr Val Gln Ala
145                 150                 155                 160
Leu Leu Pro Val Leu Cys Gln Ala His Gly Leu Thr Pro Glu Gln Val
                165                 170                 175
Val Ala Ile Ala Ser Asn Ile Gly Gly Lys Gln Ala Leu Glu Thr Val
            180                 185                 190
Gln Ala Leu Leu Pro Val Leu Cys Gln Ala His Gly Leu Thr Pro Gln
        195                 200                 205
Gln Val Val Ala Ile Ala Ser Asn Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Glu Gln Val Val Ala Ile Ala Ser Asn Ile Gly Gly Lys Gln Ala
                245                 250                 255
Leu Glu Thr Val Gln Ala Leu Leu Pro Val Leu Cys Gln Ala His Gly
            260                 265                 270
Leu Thr Pro Glu Gln Val Val Ala Ile Ala Ser His Asp Gly Gly Lys
        275                 280                 285
Gln Ala Leu Glu Thr Val Gln Arg Leu Leu Pro Val Leu Cys Gln Ala
    290                 295                 300
His Gly Leu Thr Pro Glu Gln Val Val Ala Ile Ala Ser Asn Ile Gly
305                 310                 315                 320
Gly Lys Gln Ala Leu Glu Thr Val Gln Ala Leu Leu Pro Val Leu Cys
                325                 330                 335
Gln Ala His Gly Leu Thr Pro Gln Gln Val Val Ala Ile Ala Ser Asn
            340                 345                 350
Asn Gly Gly Lys Gln Ala Leu Glu Thr Val Gln Arg Leu Leu Pro Val
        355                 360                 365
Leu Cys Gln Ala His Gly Leu Thr Pro Gln Gln Val Val Ala Ile Ala
    370                 375                 380
Ser Asn Asn Gly Gly Lys Gln Ala Leu Glu Thr Val Gln Arg Leu Leu
385                 390                 395                 400
Pro Val Leu Cys Gln Ala His Gly Leu Thr Pro Gln Gln Val Val Ala
                405                 410                 415
Ile Ala Ser Asn Asn Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser Asn Ile Gly Gly Lys Gln Ala Leu Glu Thr Val
```

```
                450             455             460
Gln Ala Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 28
<211> LENGTH: 530
<212> TYPE: PRT
<213> ORGANISM: Artificial sequence
<220> FEATURE:
<223> OTHER INFORMATION: Synthetic polypeptide: Repeat CTLA4_T03L

<400> SEQUENCE: 28

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
```

```
                275                 280                 285
Gln Ala Leu Glu Thr Val Gln Arg Leu Leu Pro Val Leu Cys Gln Ala
290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Gln Gln Val Val Ala Ile Ala
370                 375                 380
Ser Asn Asn Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser Asn Ile Gly Gly Lys Gln Ala Leu Glu Thr Val
450                 455                 460
Gln Ala Leu Leu Pro Val Leu Cys Gln Ala His Gly Leu Thr Pro Glu
465                 470                 475                 480
Gln Val Val Ala Ile Ala Ser Asn Ile Gly Gly Lys Gln Ala Leu Glu
                485                 490                 495
Thr Val Gln Ala Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530

<210> SEQ ID NO 29
<211> LENGTH: 530
<212> TYPE: PRT
<213> ORGANISM: Artificial sequence
<220> FEATURE:
<223> OTHER INFORMATION: Synthetic polypeptide: Repeat CTLA4_T03R

<400> SEQUENCE: 29

Leu Thr Pro Gln Gln Val Val Ala Ile Ala Ser Asn Asn Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Asn Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
```

```
              100                 105                 110
Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
            130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
                180                 185                 190

Gln Arg Leu Leu Pro Val Leu Cys Gln Ala His Gly Leu Thr Pro Gln
            195                 200                 205

Gln Val Val Ala Ile Ala Ser Asn Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Glu Gln Val Val Ala Ile Ala Ser His Asp Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
                340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Glu Gln Val Val Ala Ile Ala
            370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Gln Gln Val
            435                 440                 445

Val Ala Ile Ala Ser Asn Asn Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Arg Pro Ala
            515                 520                 525
```

Leu Glu
    530

<210> SEQ ID NO 30
<211> LENGTH: 530
<212> TYPE: PRT
<213> ORGANISM: Artificial sequence
<220> FEATURE:
<223> OTHER INFORMATION: Synthetic polypeptide: Repeat CTLA4_T04L

<400> SEQUENCE: 30

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

```
Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
        420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
        515                 520                 525

Leu Glu
    530

<210> SEQ ID NO 31
<211> LENGTH: 530
<212> TYPE: PRT
<213> ORGANISM: Artificial sequence
<220> FEATURE:
<223> OTHER INFORMATION: Synthetic polypeptide: Repeat CTLA4_T04R

<400> SEQUENCE: 31

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Lys Gln Ala Leu Glu Thr Val Gln Arg Leu Leu Pro Val
            85                  90                  95

Leu Cys Gln Ala His Gly Leu Thr Pro Gln Gln Val Val Ala Ile Ala
                100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175
```

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 32
<211> LENGTH: 530
<212> TYPE: PRT
<213> ORGANISM: Artificial sequence
<220> FEATURE:
<223> OTHER INFORMATION: Synthetic polypeptide: Repeat PDCD1_T01R

<400> SEQUENCE: 32

-continued

```
Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
 50                  55                  60

Gln Ala His Gly Leu Thr Pro Gln Gln Val Val Ala Ile Ala Ser Asn
 65                  70                  75                  80

Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
            130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Ala His Gly Leu Thr Pro Glu
            195                 200                 205

Gln Val Val Ala Ile Ala Ser His Asp Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
                340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
            370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415
```

```
Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
    435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                    485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 33
<211> LENGTH: 529
<212> TYPE: PRT
<213> ORGANISM: Artificial sequence
<220> FEATURE:
<223> OTHER INFORMATION: Synthetic polypeptide: Repeat PDCD1_T01L

<400> SEQUENCE: 33

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser Asn Ile Gly
            35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
    115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240
```

```
Pro Gln Gln Val Val Ala Ile Ala Ser Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser Asn Gly Gly Lys Gln
        275                 280                 285

Ala Leu Glu Thr Val Gln Arg Leu Leu Pro Val Leu Cys Gln Ala His
        290                 295                 300

Gly Leu Thr Pro Gln Gln Val Val Ala Ile Ala Ser Asn Asn Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Gln Gln Val Val Ala Ile Ala Ser Asn Gly
            340                 345                 350

Gly Gly Lys Gln Ala Leu Glu Thr Val Gln Arg Leu Leu Pro Val Leu
        355                 360                 365

Cys Gln Ala His Gly Leu Thr Pro Gln Gln Val Val Ala Ile Ala Ser
        370                 375                 380

Asn Gly Gly Gly Lys Gln Ala Leu Glu Thr Val Gln Arg Leu Leu Pro
385                 390                 395                 400

Val Leu Cys Gln Ala His Gly Leu Thr Pro Gln Gln Val Val Ala Ile
                405                 410                 415

Ala Ser Asn Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
        435                 440                 445

Ala Ile Ala Ser Asn Gly Gly Gly Lys Gln Ala Leu Glu Thr Val Gln
        450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
        515                 520                 525

Glu

<210> SEQ ID NO 34
<211> LENGTH: 530
<212> TYPE: PRT
<213> ORGANISM: Artificial sequence
<220> FEATURE:
<223> OTHER INFORMATION: Synthetic polypeptide: Repeat PDCD1_T03R

<400> SEQUENCE: 34

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
```

```
                65                  70                  75                  80
Asp Gly Gly Lys Gln Ala Leu Glu Thr Val Gln Arg Leu Leu Pro Val
                    85                  90                  95

Leu Cys Gln Ala His Gly Leu Thr Pro Gln Gln Val Val Ala Ile Ala
                   100                 105                 110

Ser Asn Gly Gly Lys Gln Ala Leu Glu Thr Val Gln Arg Leu Leu
                   115                 120             125

Pro Val Leu Cys Gln Ala His Gly Leu Thr Pro Glu Gln Val Val Ala
                   130                 135             140

Ile Ala Ser His Asp Gly Gly Lys Gln Ala Leu Glu Thr Val Gln Arg
145                     150                 155                 160

Leu Leu Pro Val Leu Cys Gln Ala His Gly Leu Thr Pro Gln Gln Val
                    165                 170                 175

Val Ala Ile Ala Ser Asn Gly Gly Lys Gln Ala Leu Glu Thr Val
                    180                 185             190

Gln Arg Leu Leu Pro Val Leu Cys Gln Ala His Gly Leu Thr Pro Gln
                    195                 200                 205

Gln Val Val Ala Ile Ala Ser Asn Gly Gly Lys Gln Ala Leu Glu
                210                 215                 220

Thr Val Gln Arg Leu Leu Pro Val Leu Cys Gln Ala His Gly Leu Thr
225                     230                 235                 240

Pro Gln Gln Val Val Ala Ile Ala Ser Asn Gly Gly Lys Gln Ala
                    245                 250                 255

Leu Glu Thr Val Gln Arg Leu Leu Pro Val Leu Cys Gln Ala His Gly
                260                 265                 270

Leu Thr Pro Gln Gln Val Val Ala Ile Ala Ser Asn Gly Gly Lys
                275                 280                 285

Gln Ala Leu Glu Thr Val Gln Arg Leu Leu Pro Val Leu Cys Gln Ala
                290                 295                 300

His Gly Leu Thr Pro Gln Gln Val Val Ala Ile Ala Ser Asn Asn Gly
305                     310                 315                 320

Gly Lys Gln Ala Leu Glu Thr Val Gln Arg Leu Leu Pro Val Leu Cys
                    325                 330                 335

Gln Ala His Gly Leu Thr Pro Gln Gln Val Val Ala Ile Ala Ser Asn
                    340                 345                 350

Asn Gly Gly Lys Gln Ala Leu Glu Thr Val Gln Arg Leu Leu Pro Val
                    355                 360                 365

Leu Cys Gln Ala His Gly Leu Thr Pro Gln Gln Val Val Ala Ile Ala
                    370                 375             380

Ser Asn Asn Gly Gly Lys Gln Ala Leu Glu Thr Val Gln Arg Leu Leu
385                     390                 395                 400

Pro Val Leu Cys Gln Ala His Gly Leu Thr Pro Glu Gln Val Val Ala
                    405                 410                 415

Ile Ala Ser His Asp Gly Gly Lys Gln Ala Leu Glu Thr Val Gln Arg
                    420                 425                 430

Leu Leu Pro Val Leu Cys Gln Ala His Gly Leu Thr Pro Glu Gln Val
                    435                 440                 445

Val Ala Ile Ala Ser His Asp Gly Gly Lys Gln Ala Leu Glu Thr Val
                    450                 455                 460

Gln Arg Leu Leu Pro Val Leu Cys Gln Ala His Gly Leu Thr Pro Glu
465                     470                 475                 480

Gln Val Val Ala Ile Ala Ser Asn Ile Gly Gly Lys Gln Ala Leu Glu
                    485                 490                 495
```

```
Thr Val Gln Ala Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 35
<211> LENGTH: 529
<212> TYPE: PRT
<213> ORGANISM: Artificial sequence
<220> FEATURE:
<223> OTHER INFORMATION: Synthetic polypeptide: Repeat PDCD1_T03L

<400> SEQUENCE: 35

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320
```

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
            340                 345                 350

Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
        435                 440                 445

Ala Ile Ala Ser Asn Asn Gly Gly Lys Gln Ala Leu Glu Thr Val Gln
    450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
        515                 520                 525

Glu

<210> SEQ ID NO 36
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within glucocorticoid receptor
      gene (GRex2)

<400> SEQUENCE: 36
tattcactga tggactccaa agaatcatta actcctggta gagaagaaa          49

<210> SEQ ID NO 37
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within glucocorticoid receptor
      gene (GRex3T2)

<400> SEQUENCE: 37
tgcctggtgt gctctgatga agcttcagga tgtcattatg gagtcttaa           49

<210> SEQ ID NO 38
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within glucocorticoid receptor
      gene (GRex3T4)

```
<400> SEQUENCE: 38
tgctctgatg aagcttcagg atgtcattat ggagtcttaa cttgtggaa                49

<210> SEQ ID NO 39
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within glucocorticoid receptor
      gene (GRex5T1)

<400> SEQUENCE: 39
tggtgtcact gttggaggtt attgaacctg aagtgttata tgcaggata                49

<210> SEQ ID NO 40
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within glucocorticoid receptor
      gene (GRex5T2)

<400> SEQUENCE: 40
tatgatagct ctgttccaga ctcaacttgg aggatcatga ctacgctca                49

<210> SEQ ID NO 41
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within glucocorticoid receptor
      gene (GRex5T3)

<400> SEQUENCE: 41
ttatatgcag gatatgatag ctctgttcca gactcaactt ggaggatca                49

<210> SEQ ID NO 42
<211> LENGTH: 530
<212> TYPE: PRT
<213> ORGANISM: Artificial sequence
<220> FEATURE:
<223> OTHER INFORMATION: synthetic polypeptide: Repeat-GRex2-LPT9-L1

<400> SEQUENCE: 42

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
```

```
            115                 120                 125
Pro Val Leu Cys Gln Ala His Gly Leu Thr Pro Glu Gln Val Val Ala
            130                 135                 140
Ile Ala Ser Asn Ile Gly Gly Lys Gln Ala Leu Glu Thr Val Gln Ala
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
                180                 185                 190
Gln Arg Leu Leu Pro Val Leu Cys Gln Ala His Gly Leu Thr Pro Gln
            195                 200                 205
Gln Val Val Ala Ile Ala Ser Asn Gly Gly Gly Lys Gln Ala Leu Glu
        210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
                260                 265                 270
Leu Thr Pro Glu Gln Val Val Ala Ile Ala Ser Asn Ile Gly Gly Lys
            275                 280                 285
Gln Ala Leu Glu Thr Val Gln Ala Leu Leu Pro Val Leu Cys Gln Ala
        290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Gln Gln Val Val Ala Ile Ala Ser Asn
                340                 345                 350
Asn Gly Gly Lys Gln Ala Leu Glu Thr Val Gln Arg Leu Leu Pro Val
            355                 360                 365
Leu Cys Gln Ala His Gly Leu Thr Pro Gln Gln Val Val Ala Ile Ala
        370                 375                 380
Ser Asn Asn Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
                420                 425                 430
Leu Leu Pro Val Leu Cys Gln Ala His Gly Leu Thr Pro Glu Gln Val
            435                 440                 445
Val Ala Ile Ala Ser His Asp Gly Gly Lys Gln Ala Leu Glu Thr Val
        450                 455                 460
Gln Arg Leu Leu Pro Val Leu Cys Gln Ala His Gly Leu Thr Pro Gln
465                 470                 475                 480
Gln Val Val Ala Ile Ala Ser Asn Gly Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530
```

<210> SEQ ID NO 43
<211> LENGTH: 530
<212> TYPE: PRT
<213> ORGANISM: Artificial sequence
<220> FEATURE:
<223> OTHER INFORMATION: synthetic polypeptide: Repeat-GRex2-LPT9-R1

<400> SEQUENCE: 43

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365
```

```
Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Gln Gln Val
            435                 440                 445

Val Ala Ile Ala Ser Asn Asn Gly Gly Lys Gln Ala Leu Glu Thr Val
        450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
            515                 520                 525

Leu Glu
    530

<210> SEQ ID NO 44
<211> LENGTH: 530
<212> TYPE: PRT
<213> ORGANISM: Artificial sequence
<220> FEATURE:
<223> OTHER INFORMATION: synthetic polypeptide: Repeat-GRex3T2-L1

<400> SEQUENCE: 44

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
        130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
                180                 185                 190
```

Gln Arg Leu Leu Pro Val Leu Cys Gln Ala His Gly Leu Thr Pro Gln
            195                 200                 205

Gln Val Val Ala Ile Ala Ser Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
            245                 250                 255

Leu Glu Thr Val Gln Arg Leu Leu Pro Val Leu Cys Gln Ala His Gly
                260                 265                 270

Leu Thr Pro Gln Gln Val Val Ala Ile Ala Ser Asn Gly Gly Gly Lys
            275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser His Asp Gly Gly Lys Gln Ala Leu Glu Thr Val Gln Arg
        420                 425                 430

Leu Leu Pro Val Leu Cys Gln Ala His Gly Leu Thr Pro Gln Gln Val
            435                 440                 445

Val Ala Ile Ala Ser Asn Gly Gly Gly Lys Gln Ala Leu Glu Thr Val
        450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
            485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
            515                 520                 525

Leu Glu
    530

<210> SEQ ID NO 45
<211> LENGTH: 530
<212> TYPE: PRT
<213> ORGANISM: Artificial sequence
<220> FEATURE:
<223> OTHER INFORMATION: synthetic polypeptide: Repeat-GRex3T2-R1

<400> SEQUENCE: 45

Leu Thr Pro Gln Gln Val Val Ala Ile Ala Ser Asn Gly Gly Gly Lys
1               5                   10                  15

```
Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430
```

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
        450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 46
<211> LENGTH: 530
<212> TYPE: PRT
<213> ORGANISM: Artificial sequence
<220> FEATURE:
<223> OTHER INFORMATION: synthetic polypeptide: Repeat-GRex3T4-L1

<400> SEQUENCE: 46

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

```
Leu Glu Thr Val Gln Arg Leu Leu Pro Val Leu Cys Gln Ala His Gly
                260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 47
<211> LENGTH: 530
<212> TYPE: PRT
<213> ORGANISM: Artificial sequence
<220> FEATURE:
<223> OTHER INFORMATION: synthetic polypeptide: Repeat-GRex3T4-R1

<400> SEQUENCE: 47

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80
```

-continued

```
Asp Gly Gly Lys Gln Ala Leu Glu Thr Val Gln Arg Leu Leu Pro Val
             85                  90                  95
Leu Cys Gln Ala His Gly Leu Thr Pro Glu Gln Val Val Ala Ile Ala
        100                 105                 110
Ser Asn Ile Gly Gly Lys Gln Ala Leu Glu Thr Val Gln Ala Leu Leu
        115                 120                 125
Pro Val Leu Cys Gln Ala His Gly Leu Thr Pro Glu Gln Val Val Ala
130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser Asn Ile Gly Gly Lys Gln Ala Leu Glu Thr Val
            180                 185                 190
Gln Ala Leu Leu Pro Val Leu Cys Gln Ala His Gly Leu Thr Pro Glu
        195                 200                 205
Gln Val Val Ala Ile Ala Ser Asn Ile Gly Gly Lys Gln Ala Leu Glu
    210                 215                 220
Thr Val Gln Ala Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
Leu Thr Pro Gln Gln Val Val Ala Ile Ala Ser Asn Gly Gly Gly Lys
        275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Glu Gln Val Val Ala Ile Ala
    370                 375                 380
Ser Asn Ile Gly Gly Lys Gln Ala Leu Glu Thr Val Gln Ala Leu Leu
385                 390                 395                 400
Pro Val Leu Cys Gln Ala His Gly Leu Thr Pro Gln Gln Val Val Ala
                405                 410                 415
Ile Ala Ser Asn Asn Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser Asn Ile Gly Gly Lys Gln Ala Leu Glu Thr Val
    450                 455                 460
Gln Ala Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
```

```
                       500                 505                 510
Pro Gln Gln Val Val Ala Ile Ala Ser Asn Gly Gly Arg Pro Ala
            515                 520                 525

Leu Glu
    530

<210> SEQ ID NO 48
<211> LENGTH: 530
<212> TYPE: PRT
<213> ORGANISM: Artificial sequence
<220> FEATURE:
<223> OTHER INFORMATION: synthetic polypeptide: Repeat-GRex5T1-LPT8-L1

<400> SEQUENCE: 48

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
```

```
                        325                 330                 335
Gln Ala His Gly Leu Thr Pro Gln Gln Val Val Ala Ile Ala Ser Asn
            340                 345                 350
Gly Gly Gly Lys Gln Ala Leu Glu Thr Val Gln Arg Leu Leu Pro Val
            355                 360                 365
Leu Cys Gln Ala His Gly Leu Thr Pro Gln Gln Val Val Ala Ile Ala
            370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Gln Gln Val Val Ala
                405                 410                 415
Ile Ala Ser Asn Asn Gly Gly Lys Gln Ala Leu Glu Thr Val Gln Arg
            420                 425                 430
Leu Leu Pro Val Leu Cys Gln Ala His Gly Leu Thr Pro Gln Gln Val
            435                 440                 445
Val Ala Ile Ala Ser Asn Asn Gly Gly Lys Gln Ala Leu Glu Thr Val
            450                 455                 460
Gln Arg Leu Leu Pro Val Leu Cys Gln Ala His Gly Leu Thr Pro Glu
465                 470                 475                 480
Gln Val Val Ala Ile Ala Ser Asn Ile Gly Gly Lys Gln Ala Leu Glu
                485                 490                 495
Thr Val Gln Ala Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
            515                 520                 525
Leu Glu
    530

<210> SEQ ID NO 49
<211> LENGTH: 530
<212> TYPE: PRT
<213> ORGANISM: Artificial sequence
<220> FEATURE:
<223> OTHER INFORMATION: synthetic polypeptide: Repeat-GRex5T1-LPT8-R1

<400> SEQUENCE: 49

Leu Thr Pro Glu Gln Val Val Ala Ile Ala Ser Asn Ile Gly Gly Lys
1               5                   10                  15
Gln Ala Leu Glu Thr Val Gln Ala Leu Leu Pro Val Leu Cys Gln Ala
            20                  25                  30
His Gly Leu Thr Pro Gln Gln Val Val Ala Ile Ala Ser Asn Gly Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
Ser His Asp Gly Gly Lys Gln Ala Leu Glu Thr Val Gln Arg Leu Leu
        115                 120                 125
Pro Val Leu Cys Gln Ala His Gly Leu Thr Pro Gln Gln Val Val Ala
    130                 135                 140
Ile Ala Ser Asn Gly Gly Gly Lys Gln Ala Leu Glu Thr Val Gln Arg
```

```
                145                 150                 155                 160
Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
                180                 185                 190

Gln Arg Leu Leu Pro Val Leu Cys Gln Ala His Gly Leu Thr Pro Glu
                195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Gly Gly Gly Lys
                275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
                340                 345                 350

Gly Gly Gly Lys Gln Ala Leu Glu Thr Val Gln Arg Leu Leu Pro Val
                355                 360                 365

Leu Cys Gln Ala His Gly Leu Thr Pro Glu Gln Val Val Ala Ile Ala
                370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Glu Gln Val
                435                 440                 445

Val Ala Ile Ala Ser His Asp Gly Gly Lys Gln Ala Leu Glu Thr Val
                450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
                515                 520                 525

Leu Glu
    530

<210> SEQ ID NO 50
<211> LENGTH: 530
<212> TYPE: PRT
<213> ORGANISM: Artificial sequence
```

<220> FEATURE:
<223> OTHER INFORMATION: synthetic polypeptide: Repeat-GRex5T2-L1

<400> SEQUENCE: 50

```
Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400
```

```
Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 51
<211> LENGTH: 530
<212> TYPE: PRT
<213> ORGANISM: Artificial sequence
<220> FEATURE:
<223> OTHER INFORMATION: synthetic polypeptide: Repeat-GRex5T2-R1

<400> SEQUENCE: 51

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
            35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
            210                 215                 220
```

```
Thr Val Gln Ala Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Gly Gly Gly Lys
    275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
        340                 345                 350

Ile Gly Gly Lys Gln Ala Leu Glu Thr Val Gln Ala Leu Leu Pro Val
    355                 360                 365

Leu Cys Gln Ala His Gly Leu Thr Pro Gln Gln Val Val Ala Ile Ala
370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Asn Gly Gly Lys Gln Ala Leu Glu Thr Val Gln Arg
        420                 425                 430

Leu Leu Pro Val Leu Cys Gln Ala His Gly Leu Thr Pro Glu Gln Val
    435                 440                 445

Val Ala Ile Ala Ser Asn Ile Gly Gly Lys Gln Ala Leu Glu Thr Val
450                 455                 460

Gln Ala Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
    515                 520                 525

Leu Glu
    530

<210> SEQ ID NO 52
<211> LENGTH: 530
<212> TYPE: PRT
<213> ORGANISM: Artificial sequence
<220> FEATURE:
<223> OTHER INFORMATION: synthetic polypeptide: Repeat-GRex5T3-L1

<400> SEQUENCE: 52

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45
```

```
Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460
```

```
Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 53
<211> LENGTH: 530
<212> TYPE: PRT
<213> ORGANISM: Artificial sequence
<220> FEATURE:
<223> OTHER INFORMATION: synthetic polypeptide: Repeat-GRex5T3-R1

<400> SEQUENCE: 53

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285
```

Gln Ala Leu Glu Thr Val Gln Ala Leu Leu Pro Val Leu Cys Gln Ala
    290                 295                 300
His Gly Leu Thr Pro Glu Gln Val Val Ala Ile Ala Ser Asn Ile Gly
305                 310                 315                 320
Gly Lys Gln Ala Leu Glu Thr Val Gln Ala Leu Leu Pro Val Leu Cys
                325                 330                 335
Gln Ala His Gly Leu Thr Pro Gln Gln Val Val Ala Ile Ala Ser Asn
            340                 345                 350
Asn Gly Gly Lys Gln Ala Leu Glu Thr Val Gln Arg Leu Leu Pro Val
        355                 360                 365
Leu Cys Gln Ala His Gly Leu Thr Pro Gln Gln Val Val Ala Ile Ala
370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Gln Gln Val Val Ala
                405                 410                 415
Ile Ala Ser Asn Gly Gly Gly Lys Gln Ala Leu Glu Thr Val Gln Arg
            420                 425                 430
Leu Leu Pro Val Leu Cys Gln Ala His Gly Leu Thr Pro Gln Gln Val
        435                 440                 445
Val Ala Ile Ala Ser Asn Asn Gly Gly Lys Gln Ala Leu Glu Thr Val
450                 455                 460
Gln Arg Leu Leu Pro Val Leu Cys Gln Ala His Gly Leu Thr Pro Glu
465                 470                 475                 480
Gln Val Val Ala Ile Ala Ser Asn Ile Gly Gly Lys Gln Ala Leu Glu
                485                 490                 495
Thr Val Gln Ala Leu Leu Pro Val Leu Cys Gln Ala His Gly Leu Thr
            500                 505                 510
Pro Gln Gln Val Val Ala Ile Ala Ser Asn Gly Gly Arg Pro Ala
        515                 520                 525
Leu Glu
    530

<210> SEQ ID NO 54
<211> LENGTH: 47
<212> TYPE: DNA
<213> ORGANISM: Homo sapiens
<220> FEATURE:
<221> NAME/KEY: misc_feature
<223> OTHER INFORMATION: Target sequence within CD52 gene (CD52_T01)

<400> SEQUENCE: 54
ttcctcttcc tcctaccacc atcagcctcc tttacctgta ccataac                        47

<210> SEQ ID NO 55
<211> LENGTH: 49
<212> TYPE: DNA
<213> ORGANISM: Homo sapiens
<220> FEATURE:
<221> NAME/KEY: misc_feature
<223> OTHER INFORMATION: Target sequence within CD52 gene (CD52_T02)

<400> SEQUENCE: 55
ttcctcctac tcaccatcag cctcctggtt atggtacagg taagagcaa                      49

<210> SEQ ID NO 56
<211> LENGTH: 43
<212> TYPE: DNA
<213> ORGANISM: Homo sapiens

```
<220> FEATURE:
<221> NAME/KEY: misc_feature
<223> OTHER INFORMATION: Target sequence within CD52 gene (CD52_T04)

<400> SEQUENCE: 56
ttcctcctac tcaccacagc ctcctggtct tacctgtacc ata                43

<210> SEQ ID NO 57
<211> LENGTH: 43
<212> TYPE: DNA
<213> ORGANISM: Homo sapiens
<220> FEATURE:
<221> NAME/KEY: misc_feature
<223> OTHER INFORMATION: Target sequence within CD52 gene (CD52_T05)

<400> SEQUENCE: 57
tcctactcac catcagctcc tggttatttg ctcttacctg tac                43

<210> SEQ ID NO 58
<211> LENGTH: 47
<212> TYPE: DNA
<213> ORGANISM: Homo sapiens
<220> FEATURE:
<221> NAME/KEY: misc_feature
<223> OTHER INFORMATION: Target sequence within CD52 gene (CD52_T06)

<400> SEQUENCE: 58
ttatcccact tctcctctac agatacaaac tttttgtcct gagagtc            47

<210> SEQ ID NO 59
<211> LENGTH: 47
<212> TYPE: DNA
<213> ORGANISM: Homo sapiens
<220> FEATURE:
<221> NAME/KEY: misc_feature
<223> OTHER INFORMATION: Target sequence within CD52 gene (CD52_T07)

<400> SEQUENCE: 59
tggactctca ggacaaacga caccagccaa atgctgaggg gctgctg            47

<210> SEQ ID NO 60
<211> LENGTH: 530
<212> TYPE: PRT
<213> ORGANISM: Artificial sequence
<220> FEATURE:
<223> OTHER INFORMATION: synthetic polypeptide: Repeat CD52_T02-L

<400> SEQUENCE: 60

Leu Thr Pro Gln Gln Val Val Ala Ile Ala Ser Asn Gly Gly Lys
 1               5                  10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
```

-continued

```
            115                 120                 125
Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Ala His Gly Leu Thr Pro Gln
                195                 200                 205

Gln Val Val Ala Ile Ala Ser Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Glu Gln Val Val Ala Ile Ala Ser His Asp Gly Gly Lys
                275                 280                 285

Gln Ala Leu Glu Thr Val Gln Arg Leu Leu Pro Val Leu Cys Gln Ala
290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
                340                 345                 350

Asp Gly Gly Lys Gln Ala Leu Glu Thr Val Gln Arg Leu Leu Pro Val
                355                 360                 365

Leu Cys Gln Ala His Gly Leu Thr Pro Glu Gln Val Val Ala Ile Ala
370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Glu Gln Val
                435                 440                 445

Val Ala Ile Ala Ser His Asp Gly Gly Lys Gln Ala Leu Glu Thr Val
                450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
                515                 520                 525

Leu Glu
530
```

<210> SEQ ID NO 61
<211> LENGTH: 530
<212> TYPE: PRT
<213> ORGANISM: Artificial sequence
<220> FEATURE:
<223> OTHER INFORMATION: synthetic polypeptide: Repeat CD52_T02-R

<400> SEQUENCE: 61

```
Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Lys Gln Ala Leu Glu Thr Val Gln Arg Leu Leu Pro Val
        355                 360                 365
```

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 62
<211> LENGTH: 49
<212> TYPE: DNA
<213> ORGANISM: Homo sapiens
<220> FEATURE:
<221> NAME/KEY: misc_feature
<222> LOCATION: (1)..(49)
<223> OTHER INFORMATION: Target dCK2

<400> SEQUENCE: 62
tggttcctga acctgttgcc agatggtgca atgttcaaag tactcaaga                49

<210> SEQ ID NO 63
<211> LENGTH: 2814
<212> TYPE: DNA
<213> ORGANISM: artificial sequence
<220> FEATURE:
<223> OTHER INFORMATION: TALEN dCK2 LEFT

<400> SEQUENCE: 63
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480 ttgaccccc agcaggtggt ggccatcgcc agcaataatg gtggcaagca ggcgctggag   540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660

```
ccggtgctgt gccaggccca cggcttgacc ccccagcagg tggtggccat cgccagcaat      720
ggcggtggca agcaggcgct ggagacggtc agcggctgt tgccggtgct gtgccaggcc       780
cacggcttga ccccccagca ggtggtggcc atcgccagca atggcggtgg caagcaggcg      840
ctggagacgt ccagcggct gttgccggtg ctgtgccagg cccacggctt gaccccggag       900
caggtggtgg ccatcgccag ccacgatggc ggcaagcagg cgctggagac ggtccagcgg      960
ctgttgccgg tgctgtgcca ggcccacggc ttgaccccgg agcaggtggt ggccatcgcc     1020
agccacgatg gcggcaagca ggcgctggag acggtccagc ggctgttgcc ggtgctgtgc     1080
caggcccacg gcttgacccc ccagcaggtg gtggccatcg ccagcaatgg cggtggcaag     1140
caggcgctgg agacggtcca gcggctgttg ccggtgctgt gccaggccca cggcttgacc     1200
ccccagcagg tggtggccat cgccagcaat aatggtggca agcaggcgct ggagacggtc     1260
cagcggctgt tgccggtgct gtgccaggcc cacggcttga ccccggagca ggtggtggcc     1320
atcgccagca atattggtgg caagcaggcg ctggagacgg tgcaggcgct gttgccggtg     1380
ctgtgccagg cccacggctt gaccccggag caggtggtgg ccatcgccag caatattggt     1440
ggcaagcagg cgctggagac ggtgcaggcg ctgttgccgg tgctgtgcca ggcccacggc     1500
ttgaccccgg agcaggtggt ggccatcgcc agccacgatg gcggcaagca ggcgctggag     1560
acggtccagc ggctgttgcc ggtgctgtgc caggcccacg gcttgacccc ggagcaggtg     1620
gtggccatcg ccagccacga tggcggcaag caggcgctgg agacggtcca gcggctgttg     1680
ccggtgctgt gccaggccca cggcttgacc ccccagcagg tggtggccat cgccagcaat     1740
ggcggtggca agcaggcgct ggagacggtc agcggctgt tgccggtgct gtgccaggcc      1800
cacggcttga ccccccagca ggtggtggcc atcgccagca ataatggtgg caagcaggcg     1860
ctggagacgg tccagcggct gttgccggtg ctgtgccagg cccacggctt gaccccccag     1920
caggtggtgg ccatcgccag caatggcggt ggcaagcagg cgctggagac ggtccagcgg     1980
ctgttgccgg tgctgtgcca ggcccacggc ttgacccctc agcaggtggt ggccatcgcc     2040
agcaatggcg gcggcaggcc ggcgctggag agcattgttg cccagttatc tcgccctgat     2100
ccggcgttgg ccgcgttgac caacgaccac ctcgtcgcct tggcctgcct cggcgggcgt     2160
cctgcgctgg atgcagtgaa aaagggattg ggggatccta tcagccgttc ccagctggtg     2220
aagtccgagc tggaggagaa gaaatccgag ttgaggcaca agctgaagta cgtgccccac     2280
gagtacatcg agctgatcga gatcgcccgg aacagcaccc aggaccgtat cctggagatg     2340
aaggtgatgg agttcttcat gaaggtgtac ggctacaggg gcaagcacct gggcggctcc     2400
aggaagcccg acggcgccat ctacaccgtg ggctcccccca tcgactacgg cgtgatcgtg     2460
gacaccaagg cctactccgg cggctacaac ctgcccatcg gccaggccga cgaaatgcag     2520
aggtacgtgg aggagaacca gaccaggaac aagcacatca ccccaacga gtggtggaag     2580 gtgtacccct ccagcgtgac cgagttcaag ttcctgttcg tgtccggcca cttcaagggc     2640
aactacaagg cccagctgac caggctgaac cacatcacca actgcaacgg cgccgtgctg     2700
tccgtggagg agctcctgat cggcggcgag atgatcaagg ccggcaccct gaccctggag     2760
gaggtgagga ggaagttcaa caacggcgag atcaacttcg cggccgactg ataa           2814
```

<210> SEQ ID NO 64
<211> LENGTH: 2814
<212> TYPE: DNA
<213> ORGANISM: artificial sequence
<220> FEATURE:

<223> OTHER INFORMATION: TALEN dCK2 RIGHT

<400> SEQUENCE: 64

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccccgg agcaggtggt ggccatcgcc agccacgatg gcggcaagca ggcgctggag     540
acggtccagc ggctgttgcc ggtgctgtgc caggcccacg gcttgacccc ccagcaggtg     600
gtggccatcg ccagcaatgg cggtggcaag caggcgctgg agacggtcca gcggctgttg     660
ccggtgctgt gccaggccca cggcttgacc cccagcagg tggtggccat cgccagcaat     720
ggcggtggca agcaggcgct ggagacggtc agcggctgt tgccggtgct gtgccaggcc     780
cacggcttga ccccccagca ggtggtggcc atcgccagca ataatggtgg caagcaggcg     840
ctggagacgt ccagcggct gttgccggtg ctgtgccagg cccacggctt gaccccggag     900
caggtggtgg ccatcgccag caatattggt ggcaagcagg cgctggagac ggtgcaggcg     960
ctgttgccgg tgctgtgcca ggcccacggc ttgaccccc agcaggtggt ggccatcgcc    1020
agcaataatg gtggcaagca ggcgctggag acggtccagc ggctgttgcc ggtgctgtgc    1080
caggcccacg gcttgacccc ccagcaggtg gtggccatcg ccagcaatgg cggtggcaag    1140
caggcgctgg agacggtcca gcggctgttg ccggtgctgt gccaggccca cggcttgacc    1200
ccggagcagg tggtggccat cgccagcaat attggtggca agcaggcgct ggagacggtg    1260
caggcgctgt tgccggtgct gtgccaggcc cacggcttga ccccggagca ggtggtggcc    1320
atcgccagcc acgatggcgg caagcaggcg ctggagacgg tccagcggct gttgccggtg    1380
ctgtgccagg cccacggctt gaccccccag caggtggtgg ccatcgccag caatggcggt    1440
ggcaagcagg cgctggagac ggtccagcgg ctgttgccgg tgctgtgcca ggcccacggc    1500
ttgaccccc agcaggtggt ggccatcgcc agcaatggcg gtggcaagca ggcgctggag    1560
acggtccagc ggctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc cccagcagg tggtggccat cgccagcaat    1740
aatggtggca agcaggcgct ggagacggtc agcggctgt tgccggtgct gtgccaggcc    1800
cacggcttga ccccggagca ggtggtggcc atcgccagca atattggtgg caagcaggcg    1860
ctggagacgg tgcaggcgct gttgccggtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgaccccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctga tgcagtgaa aaagggattg ggggatccta tcagccgttc ccagctggtg    2220
aagtccgagc tggaggagaa gaaatccgag ttgaggcaca agctgaagta cgtgcccac    2280
```

```
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca ccccaacga gtggtggaag    2580 gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 65
<211> LENGTH: 59
<212> TYPE: DNA
<213> ORGANISM: Homo sapiens
<220> FEATURE:
<221> NAME/KEY: misc_feature
<222> LOCATION: (1)..(59)

<400> SEQUENCE: 65
tgatcctctt gtcccacaga tatccagaac cctgaccctg ccgtgtacca gctgagaga     59

<210> SEQ ID NO 66
<211> LENGTH: 2832
<212> TYPE: DNA
<213> ORGANISM: artificial sequence
<220> FEATURE:
<223> OTHER INFORMATION: TALEN TRAC LEFT

<400> SEQUENCE: 66
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcc ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccggag caggtggtgg ccatcgccag ccacgatggc     540
ggcaagcagg cgctggagac ggtccagcgg ctgttgccgg tgctgtgcca ggcccacggc     600
ttgacccccc agcaggtggt ggccatcgcc agcaatggcg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagcaat     840
attggtggca gcaggcgct ggagacggtg caggcgctgt gccggtgct gtgccaggcc     900 cacggcttga ccccccagca ggtggtggcc atcgccagca taatggtggg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
```

```
agcaatggcg gtggcaagca ggcgctggag acggtccagc ggctgttgcc ggtgctgtgc   1200
caggcccacg gcttgacccc ccagcaggtg gtggccatcg ccagcaataa tggtggcaag   1260
caggcgctgg agacggtcca gcggctgttg ccggtgctgt gccaggccca cggcttgacc   1320
ccccagcagg tggtggccat cgccagcaat aatggtggca agcaggcgct ggagacggtc   1380
cagcggctgt tgccggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtgcaggcg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccggagcagg tggtggccat cgccagccac   1860
gatggcggca agcaggcgct ggagacggtc cagcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280 ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcaccctga ccctggagga ggtgaggagg aagttcaaca acggcgagat caacttcgcg   2820
gccgactgat aa                                                      2832

<210> SEQ ID NO 67
<211> LENGTH: 2814
<212> TYPE: DNA
<213> ORGANISM: artificial sequence
<220> FEATURE:
<223> OTHER INFORMATION: TALEN TRAC RIGHT

<400> SEQUENCE: 67
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgcaca cgaagcgat cgttggcgtc    300
```

```
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480 ttgaccccc agcaggtggt ggccatcgcc agcaatggcg gtggcaagca ggcgctggag    540
acggtccagc ggctgttgcc ggtgctgtgc caggcccacg gcttgacccc ccagcaggtg    600
gtggccatcg ccagcaataa tggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc agcggctgt gccggtgct gtgccaggcc    780 cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
ccggagcagg tggtggccat cgccagccac gatggcggca agcaggcgct ggagacggtc   1260
cagcggctgt gccggtgct gtgccaggcc acggcttga ccccggagca ggtggtggcc   1320
atcgccagca atattggtgg caagcaggcg ctggagacgg tgcaggcgct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccgg agcaggtggt ggccatcgcc agcaatattg gtggcaagca ggcgctggag   1560
acggtgcagg cgctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagcaat   1740
attggtggca agcaggcgct ggagacggtg caggcgctgt gccggtgct gtgccaggcc   1800 cacggcttga ccccccagca ggtggtggcc atcgccagca atggcggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgaccccc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg caagcacct gggcggctcc   2400 aggaagcccg acggcgccat ctacaccgtg ggctccccca tcgactacgg cgtgatcgtg   2460
gacaccaagg cctactccgg cggctacaac ctgcccatcg ccaggccga cgaaatgcag   2520 aggtacgtgg aggagaacca gaccaggaac aagcacatca accccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
```

```
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 68
<211> LENGTH: 65
<212> TYPE: DNA
<213> ORGANISM: artificial sequence
<220> FEATURE:
<223> OTHER INFORMATION: Oligo T7 DEEP Forward dcK 2 locus

<400> SEQUENCE: 68

```
ccatctcatc cctgcgtgtc tccgactcag tagagacgag tgcttaatga aattgggcag    60
ggagc                                                                65
```

<210> SEQ ID NO 69
<211> LENGTH: 54
<212> TYPE: DNA
<213> ORGANISM: artificial sequence
<220> FEATURE:
<223> OTHER INFORMATION: Oligo T7 DEEP Reverse dcK 2 locus

<400> SEQUENCE: 69

```
cctatcccct gtgtgccttg gcagtctcag tgaaacccat tgatatggag agcc          54
```

<210> SEQ ID NO 70
<211> LENGTH: 65
<212> TYPE: DNA
<213> ORGANISM: artificial sequence
<220> FEATURE:
<223> OTHER INFORMATION: Oligo T7 DEEP Forward TRAC locus

<400> SEQUENCE: 70

```
ccatctcatc cctgcgtgtc tccgactcag tagagacgag ttggccaaga ttgatagctt    60
gtgcc                                                                65
```

<210> SEQ ID NO 71
<211> LENGTH: 55
<212> TYPE: DNA
<213> ORGANISM: artificial sequence
<220> FEATURE:
<223> OTHER INFORMATION: Oligo T7 DEEP Reverse TRAC locus

<400> SEQUENCE: 71

```
cctatcccct gtgtgccttg gcagtctcag aagtcagatt tgttgctcca ggcca         55
```

<210> SEQ ID NO 72
<211> LENGTH: 67
<212> TYPE: DNA
<213> ORGANISM: artificial sequence
<220> FEATURE:
<223> OTHER INFORMATION: Oligo T7 DEEP Forward HPRT locus

<400> SEQUENCE: 72

```
ccatctcatc cctgcgtgtc tccgactcag agcactgtag cacctaaatt tctctgatag    60
actaagg                                                              67
```

<210> SEQ ID NO 73
<211> LENGTH: 54
<212> TYPE: DNA
<213> ORGANISM: artificial sequence
<220> FEATURE:
<223> OTHER INFORMATION: Oligo T7 DEEP Reverse HPRT locus

<400> SEQUENCE: 73
cctatcccct gtgtgccttg gcagtctcag actaagtaat tagtaaggcc ctcc    54

<210> SEQ ID NO 74
<211> LENGTH: 2814
<212> TYPE: DNA
<213> ORGANISM: artificial sequence
<220> FEATURE:
<223> OTHER INFORMATION: TALEN HPRT 1 LEFT

<400> SEQUENCE: 74

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa cacccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgacccccc agcaggtggt ggccatcgcc agcaataatg gtggcaagca ggcgctggag | 540 |
| acggtccagc ggctgttgcc ggtgctgtgc caggcccacg gcttgacccc ggagcaggtg | 600 |
| gtggccatcg ccagcaatat tggtggcaag caggcgctgg agacggtgca ggcgctgttg | 660 |
| ccggtgctgt gccaggccca cggcttgacc ccggagcagg tggtggccat cgccagccac | 720 |
| gatggcggca agcaggcgct ggagacggtc agcggctgt tgccggtgct gtgccaggcc | 780 |
| cacggcttga ccccggagca ggtggtggcc atcgccagcc acgatggcgg caagcaggcg | 840 |
| ctggagacgg tccagcggct gttgccggtg ctgtgccagg cccacggctt gacccccag | 900 |
| caggtggtgg ccatcgccag caatggcggt ggcaagcagg cgctggagac ggtccagcgg | 960 |
| ctgttgccgg tgctgtgcca ggcccacggc ttgacccccc agcaggtggt ggccatcgcc | 1020 |
| agcaatggcg gtggcaagca ggcgctggag acggtccagc ggctgttgcc ggtgctgtgc | 1080 |
| caggcccacg gcttgacccc ccagcaggtg gtggccatcg ccagcaataa tggtggcaag | 1140 |
| caggcgctgg agacggtcca gcggctgttg ccggtgctgt gccaggccca cggcttgacc | 1200 |
| ccggagcagg tggtggccat cgccagcaat attggtggca agcaggcgct ggagacggtg | 1260 |
| caggcgctgt tgccggtgct gtgccaggcc cacggcttga ccccccagca ggtggtggcc | 1320 |
| atcgccagca atggcggtgg caagcaggcg ctggagacgg tccagcggct gttgccggtg | 1380 |
| ctgtgccagg cccacggctt gacccccag caggtggtgg ccatcgccag caatggcggt | 1440 |
| ggcaagcagg cgctggagac ggtccagcgg ctgttgccgg tgctgtgcca ggcccacggc | 1500 |
| ttgacccccc agcaggtggt ggccatcgcc agcaatggcg gtggcaagca ggcgctggag | 1560 |
| acggtccagc ggctgttgcc ggtgctgtgc caggcccacg gcttgacccc ggagcaggtg | 1620 |
| gtggccatcg ccagcaatat tggtggcaag caggcgctgg agacggtgca ggcgctgttg | 1680 |
| ccggtgctgt gccaggccca cggcttgacc ccccagcagg tggtggccat cgccagcaat | 1740 |
| ggcggtggca agcaggcgct ggagacggtc agcggctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gacccccag | 1920 |
| caggtggtgg ccatcgccag caatggcggt ggcaagcagg cgctggagac ggtccagcgg | 1980 |

-continued

| | |
|---|---|
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acgcgccat ctacaccgtg gctcccccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 75
<211> LENGTH: 2814
<212> TYPE: DNA
<213> ORGANISM: artificial sequence
<220> FEATURE:
<223> OTHER INFORMATION: TALEN HPRT 1 RIGHT

<400> SEQUENCE: 75

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa cacccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgacccccc agcaggtggt ggccatcgcc agcaatggcg gtggcaagca ggcgctggag | 540 |
| acggtccagc ggctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccggagcagg tggtggccat cgccagccac | 720 |
| gatggcggca gcaggcgct ggagacggtc agcggctgt tgccggtgct gtgccaggcc | 780 |
| cacggcttga ccccggagca ggtggtggcc atcgccagca atattggtgg caagcaggcg | 840 |
| ctggagacgg tgcaggcgct gttgccggtg ctgtgccagg cccacggctt gaccccggag | 900 |
| caggtggtgg ccatcgccag caatattggt ggcaagcagg cgctggagac ggtgcaggcg | 960 |
| ctgttgccgg tgctgtgcca ggcccacggc ttgaccccgg agcaggtggt ggccatcgcc | 1020 |
| agcaatattg gtggcaagca ggcgctggag acggtgcagg cgctgttgcc ggtgctgtgc | 1080 |
| caggcccacg gcttgacccc cagcaggtg gtggccatcg ccagcaatgg cggtggcaag | 1140 |
| caggcgctgg agacggtcca gcggctgttg ccggtgctgt gccaggccca cggcttgacc | 1200 |

-continued

```
ccggagcagg tggtggccat cgccagccac gatggcggca agcaggcgct ggagacggtc      1260
cagcggctgt tgccggtgct gtgccaggcc cacggcttga ccccggagca ggtggtggcc      1320
atcgccagcc acgatggcgg caagcaggcg ctggagacgg tccagcggct gttgccggtg      1380
ctgtgccagg cccacggctt gaccccccag caggtggtgg ccatcgccag caatggcggt      1440
ggcaagcagg cgctggagac ggtccagcgg ctgttgccgg tgctgtgcca ggcccacggc      1500
ttgaccccgg agcaggtggt ggccatcgcc agccacgatg gcggcaagca ggcgctggag      1560
acggtccagc ggctgttgcc ggtgctgtgc caggcccacg gcttgacccc ggagcaggtg      1620
gtggccatcg ccagcaatat tggtggcaag caggcgctgg agacggtgca ggcgctgttg      1680
ccggtgctgt gccaggccca cggcttgacc ccccagcagg tggtggccat cgccagcaat      1740
aatggtggca agcaggcgct ggagacggtc agcggctgt tgccggtgct gtgccaggcc      1800
cacggcttga ccccggagca ggtggtggcc atcgccagcc acgatggcgg caagcaggcg      1860
ctggagacgg tccagcggct gttgccggtg ctgtgccagg cccacggctt gaccccggag      1920
caggtggtgg ccatcgccag caatattggt ggcaagcagg cgctggagac ggtgcaggcg      1980
ctgttgccgg tgctgtgcca ggcccacggc ttgaccccct cagcaggtggt ggccatcgcc     2040 agcaatggcg gcggcaggcc ggcgctggag agcattgttg cccagttatc tcgccctgat      2100
ccggcgttgg ccgcgttgac caacgaccac ctcgtcgcct tggcctgcct cggcgggcgt      2160
cctgcgctga tgcagtgaa aagggattg ggggatccta tcagccgttc ccagctggtg        2220
aagtccgagc tggaggagaa gaaatccgag ttgaggcaca agctgaagta cgtgccccac      2280
gagtacatcg agctgatcga gatcgcccgg aacagcaccc aggaccgtat cctggagatg      2340
aaggtgatgg agttcttcat gaaggtgtac ggctacaggg gcaagcacct gggcggctcc      2400
aggaagcccg acgcgccat ctacaccgtg ggctccccca tcgactacgg cgtgatcgtg       2460
gacaccaagg cctactccgg cggctacaac ctgcccatcg gccaggccga cgaaatgcag      2520
aggtacgtgg aggagaacca gaccaggaac aagcacatca accccaacga gtggtggaag      2580
gtgtacccct ccagcgtgac cgagttcaag ttcctgttcg tgtccggcca cttcaagggc      2640
aactacaagg cccagctgac caggctgaac cacatcacca actgcaacgg cgccgtgctg      2700
tccgtggagg agctcctgat cggcggcgag atgatcaagg ccggcaccct gaccctggag      2760
gaggtgagga ggaagttcaa caacggcgag atcaacttcg cggccgactg ataa            2814
```

<210> SEQ ID NO 76
<211> LENGTH: 49
<212> TYPE: DNA
<213> ORGANISM: Homo sapiens
<220> FEATURE:
<221> NAME/KEY: misc_feature
<222> LOCATION: (1)..(49)

<400> SEQUENCE: 76

```
tgaccttgat ttattttgca tacctaatca ttatgctgag gatttggaa                   49
```

<210> SEQ ID NO 77
<211> LENGTH: 3201
<212> TYPE: DNA
<213> ORGANISM: artificial sequence
<220> FEATURE:
<223> OTHER INFORMATION: TALEN HPRT 2 LEFT

<400> SEQUENCE: 77

```
atgggcgatc ctaaaaagaa acgtaaggtc atcgattacc catacgatgt tccagattac      60
```

```
gctatcgata tcgccgaccc cattcgttcg cgcacaccaa gtcctgcccg cgagcttctg    120
cccggacccc aacccgatgg ggttcagccg actgcagatc gtggggtgtc tccgcctgcc    180
ggcggccccc tggatggctt gccggctcgg cggacgatgt cccggacccg gctgccatct    240 cccctgccc cctcacctgc gttctcggcg ggcagcttca gtgacctgtt acgtcagttc     300
gatccgtcac ttttaatac atcgcttttt gattcattgc ctcccttcgg cgctcaccat     360
acagaggctg ccacaggcga gtgggatgag gtgcaatcgg gtctgcgggc agccgacgcc    420
cccccaccca ccatgcgcgt ggctgtcact gccgcgcggc cccgcgcgc caagccggcg     480 ccgcgacgac gtgctgcgca accctccgac gcttcgccgg cggcgcaggt ggatctacgc    540
acgctcggct acagccagca gcaacaggag aagatcaaac cgaaggttcg ttcgacagtg    600
gcgcagcacc acgaggcact ggtcggccac gggtttacac acgcgcacat cgttgcgtta    660
agccaacacc cggcagcgtt agggaccgtc gctgtcaagt atcaggacat gatcgcagcg    720
ttgccagagg cgacacacga agcgatcgtt ggcgtcggca aacagtggtc cggcgcacgc    780
gctctggagg ccttgctcac ggtggcggga gagttgagag gtccaccgtt acagttggac    840
acaggccaac ttctcaagat tgcaaaacgt ggcggcgtga ccgcagtgga ggcagtgcat    900
gcatggcgca atgcactgac gggtgccccg ctcaacttga ccccccagca ggtggtggcc    960
atcgccagca ataatggtgg caagcaggcg ctggagacgg tccagcggct gttgccggtg   1020
ctgtgccagg cccacggctt gaccccggag caggtggtgg ccatcgccag caatattggt   1080
ggcaagcagg cgctggagac ggtgcaggcg ctgttgccgg tgctgtgcca ggcccacggc   1140
ttgacccccc agcaggtggt ggccatcgcc agcaataatg gtggcaagca ggcgctggag   1200
acggtccagc ggctgttgcc ggtgctgtgc caggcccacg gcttgacccc ccagcaggtg   1260
gtggccatcg ccagcaataa tggtggcaag caggcgctgg agacggtcca gcggctgttg   1320
ccggtgctgt gccaggccca cggcttgacc ccggagcagg tggtggccat cgccagcaat   1380
attggtggca agcaggcgct ggagacggtg caggcgctgt gccggtgct gtgccaggcc    1440 cacggcttga ccccccagca ggtggtggcc atcgccagca atggcggtgg caagcaggcg   1500
ctggagacgg tccagcggct gttgccggtg ctgtgccagg cccacggctt gaccccccag   1560
caggtggtgg ccatcgccag caatggcggt ggcaagcagg cgctggagac ggtccagcgg   1620
ctgttgccgg tgctgtgcca ggcccacggc ttgacccccc agcaggtggt ggccatcgcc   1680
agcaatggcg gtgcaagca ggcgctggag acggtccagc ggctgttgcc ggtgctgtgc    1740
caggcccacg gcttgacccc ccagcaggtg gtggccatcg ccagcaataa tggtggcaag   1800
caggcgctgg agacggtcca gcggctgttg ccggtgctgt gccaggccca cggcttgacc   1860
ccccagcagg tggtggccat cgccagcaat aatggtggca agcaggcgct ggagacggtc   1920
cagcggctgt tgccggtgct gtgccaggcc cacggcttga ccccggagca ggtggtggcc   1980
atcgccagca atattggtgg caagcaggcg ctggagacgg tgcaggcgct gttgccggtg   2040
ctgtgccagg cccacggctt gaccccggag caggtggtgg ccatcgccag caatattggt   2100
ggcaagcagg cgctggagac ggtgcaggcg ctgttgccgg tgctgtgcca ggcccacggc   2160
ttgaccccgg agcaggtggt ggccatcgcc agcaatattg gtggcaagca ggcgctggag   2220
acggtgcagg cgctgttgcc ggtgctgtgc caggcccacg gcttgacccc ccagcaggtg   2280
gtggccatcg ccagcaataa tggtggcaag caggcgctgg agacggtcca gcggctgttg   2340
ccggtgctgt gccaggccca cggcttgacc ccccagcagg tggtggccat cgccagcaat   2400
aatggtggca agcaggcgct ggagacggtc cagcggctgt tgccggtgct gtgccaggcc   2460
```

```
cacggcttga cccctcagca ggtggtggcc atcgccagca atggcggcgg caggccggcg    2520
ctggagagca ttgttgccca gttatctcgc cctgatccga gtggcagcgg aagtggcggg    2580
gatcctatca gccgttccca gctggtgaag tccgagctgg aggagaagaa atccgagttg    2640
aggcacaagc tgaagtacgt gccccacgag tacatcgagc tgatcgagat cgcccggaac    2700
agcacccagg accgtatcct ggagatgaag gtgatggagt tcttcatgaa ggtgtacggc    2760
tacaggggca agcacctggg cggctccagg aagcccgacg cgccatctca ccgtgggc    2820 tcccccatcg actacggcgt gatcgtggac accaaggcct actccggcgg ctacaacctg    2880
cccatcggcc aggccgacga aatgcagagg tacgtggagg agaaccagac caggaacaag    2940
cacatcaacc ccaacgagtg gtggaaggtg taccccctcca gcgtgaccga gttcaagttc    3000
ctgttcgtgt ccggccactt caagggcaac tacaaggccc agctgaccag gctgaaccac    3060
atcaccaact gcaacggcgc cgtgctgtcc gtggaggagc tcctgatcgg cggcgagatg    3120
atcaaggccg gcaccctgac cctggaggag gtgaggagga gttcaacaa cggcgagatc    3180 aacttcgcgg ccgactgata a                                              3201
```

<210> SEQ ID NO 78
<211> LENGTH: 3201
<212> TYPE: DNA
<213> ORGANISM: artificial sequence
<220> FEATURE:
<223> OTHER INFORMATION: TALEN HPRT 2 RIGHT

<400> SEQUENCE: 78

```
atgggcgatc ctaaaaagaa acgtaaggtc atcgattacc catacgatgt tccagattac      60
gctatcgata tcgccgaccc cattcgttcg cgcacaccaa gtcctgcccg cgagcttctg     120
cccggacccc aacccgatgg ggttcagccg actgcagatc gtggggtgtc tccgcctgcc     180
ggcggccccc tggatggctt gccggctcgg cggacgatgt cccggacccg gctgccatct     240 cccccctgccc cctcacctgc gttctcggcg ggcagcttca gtgacctgtt acgtcagttc     300
gatccgtcac tttttaatac atcgcttttt gattcattgc ctcccttcgg cgctcaccat     360
acagaggctg ccacaggcga gtgggatgag gtgcaatcgg gtctgcgggc agccgacgcc     420
cccccaccca ccatgcgcgt ggctgtcact gccgcgcggc cccgcgcgc caagccggcg     480 ccgcgacgac gtgctgcgca accctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta     660
agccaacacc cggcagcgtt agggaccgtc gctgtcaagt atcaggacat gatcgcagcg     720
ttgccagagg cgacacacga agcgatcgtt ggcgtcggca aacagtggtc cggcgcacgc     780
gctctggagg ccttgctcac ggtggcggga gagttgagag gtccaccgtt acagttggac     840
acaggccaac ttctcaagat tgcaaaacgt ggcggcgtga ccgcagtgga ggcagtgcat     900
gcatggcgca atgcactgac gggtgccccg ctcaacttga ccccggagca ggtggtggcc     960
atcgccagcc acgatggcgg caagcaggcg ctggagacgg tccagcggct gttgccggtg    1020
ctgtgccagg cccacggctt gaccccggag caggtggtgg ccatcgccag ccacgatggc    1080
ggcaagcagg cgctggagac ggtccagcgg ctgttgccgg tgctgtgcca ggcccacggc    1140
ttgaccccgg agcaggtggt ggccatcgcc agcaatattg gtggcaagca ggcgctggag    1200
acggtgcagg cgctgttgcc ggtgctgtgc caggcccacg gcttgacccc ccagcaggtg    1260
```

```
gtggccatcg ccagcaatgg cggtggcaag caggcgctgg agacggtcca gcggctgttg    1320
ccggtgctgt gccaggccca cggcttgacc ccggagcagg tggtggccat cgccagcaat    1380
attggtggca agcaggcgct ggagacggtg caggcgctgt tgccggtgct gtgccaggcc    1440
cacggcttga ccccggagca ggtggtggcc atcgccagca atattggtgg caagcaggcg    1500
ctggagacgg tgcaggcgct gttgccggtg ctgtgccagg cccacggctt gaccccccag    1560
caggtggtgg ccatcgccag caatggcggt ggcaagcagg cgctggagac ggtccagcgg    1620
ctgttgccgg tgctgtgcca ggcccacggc ttgaccccc agcaggtggt ggccatcgcc    1680
agcaatggcg gtggcaagca ggcgctggag acggtccagc ggctgttgcc ggtgctgtgc    1740
caggcccacg gcttgacccc ggagcaggtg gtggccatcg ccagcaatat tggtggcaag    1800
caggcgctgg agacggtgca ggcgctgttg ccggtgctgt gccaggccca cggcttgacc    1860
ccccagcagg tggtggccat cgccagcaat aatggtggca agcaggcgct ggagacggtc    1920
cagcggctgt tgccggtgct gtgccaggcc cacggcttga ccccccagca ggtggtggcc    1980
atcgccagca atggcggtgg caagcaggcg ctggagacgg tccagcggct gttgccggtg    2040
ctgtgccagg cccacggctt gaccccggag caggtggtgg ccatcgccag ccacgatggc    2100
ggcaagcagg cgctggagac ggtccagcgg ctgttgccgg tgctgtgcca ggcccacggc    2160
ttgacccccg gagcaggtgg tggccatcgc cagccacgatg gcggcaagca ggcgctggag    2220
acggtccagc ggctgttgcc ggtgctgtgc caggcccacg gcttgacccc ggagcaggtg    2280
gtggccatcg ccagcaatat tggtggcaag caggcgctgg agacggtgca ggcgctgttg    2340
ccggtgctgt gccaggccca cggcttgacc ccccagcagg tggtggccat cgccagcaat    2400
ggcggtggca agcaggcgct ggagacggtc cagcggctgt gccggtgct gtgccaggcc    2460 cacggcttga cccctcagca ggtggtggcc atcgccagca atggcggcgg caggccggcg    2520
ctggagagca ttgttgccca gttatctcgc cctgatccga gtggcagcgg aagtggcggg    2580
gatcctatca gccgttccca gctggtgaag tccgagctgg aggagaagaa atccgagttg    2640
aggcacaagc tgaagtacgt gccccacgag tacatcgagc tgatcgagat cgcccggaac    2700
agcacccagg accgtatcct ggagatgaag gtgatggagt tcttcatgaa ggtgtacggc    2760
tacaggggca agcacctggg cggctccagg aagcccgacg gcgccatcta caccgtgggc    2820
tcccccatcg actacggcgt gatcgtggac accaaggcct actccggcgg ctacaacctg    2880
cccatcggcc aggccgacga aatgcagagg tacgtggagg agaaccagac caggaacaag    2940
cacatcaacc ccaacgagtg gtggaaggtg taccccctcca gcgtgaccga gttcaagttc    3000
ctgttcgtgt ccggccactt caagggcaac tacaaggccc agctgaccag gctgaaccac    3060
atcaccaact gcaacggcgc cgtgctgtcc gtgcaggagc tcctgatcgg cggcgagatg    3120
atcaaggccg gcaccctgac cctggaggag gtgaggagga agttcaacaa cggcgagatc    3180
aacttcgcgg ccgactgata a                                              3201
```

<210> SEQ ID NO 79
<211> LENGTH: 45
<212> TYPE: DNA
<213> ORGANISM: Homo sapiens
<220> FEATURE:
<221> NAME/KEY: misc_feature
<222> LOCATION: (1)..(45)

<400> SEQUENCE: 79

```
tgaggatttg gaaagggtgt ttattcctca tggactaatt atgga                       45
```

METHOD OF ENGINEERING CHEMOTHERAPY DRUG RESISTANT T-CELLS FOR IMMUNOTHERAPY

SEQUENCE LISTING

The instant application contains a Sequence Listing which has been filed electronically in ASCII format and is hereby incorporated by reference in its entirety. Said ASCII copy, created on Sep. 1, 2016, is named DI201322US1_ST25.txt and is 202,273 bytes in size.

FIELD OF THE INVENTION

The present invention relates to the use of "off-the-shelf" allogeneic therapeutic cells for immunotherapy in conjunction with chemotherapy to treat patients with cancer. In particular, the inventors developed a method of engineering allogeneic T-cells resistant to chemotherapeutic agents. The therapeutic benefits afforded by this strategy should be enhanced by the synergistic effects between chemotherapy and immunotherapy. In particular, the present invention relates to a method for modifying T-cells by inactivating at least one gene encoding T-cell receptor component and by modifying said T-cells to confer drug resistance. The invention opens the way to standard and affordable adoptive immunotherapy strategies for treating cancer.

BACKGROUND OF THE INVENTION

Adoptive immunotherapy, which involves the transfer of autologous antigen-specific T-cells generated ex vivo, is a promising strategy to treat cancer. The T-cells used for adoptive immunotherapy can be generated either by expansion of antigen-specific T cells or redirection of T-cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T-cells has been shown to be successful in treating melanoma. Novel specificities in T-cells have been successfully generated through the genetic transfer of transgenic T cell receptors or chimeric antigen receptors (CARs). CARs are synthetic receptors consisting of a targeting moiety that is associated with one or more signaling domains in a single fusion molecule. CARs have successfully allowed T-cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

Ideally, one would like to use a standardized therapy in which allogeneic therapeutic cells could be pre-manufactured, characterized in detail, and available for immediate administration to patients. However, allogeneic T-cells are obtained from individuals belonging to the same species but are genetically dissimilar. Thus, endogenous TCR specificities of allogeneic cells recognize the host tissue as foreign, resulting in graft versus host disease (GvHD), which can lead to serious tissue damage and death. T cell receptors (TCR) are cell surface receptors that participate in the activation of T cells in response to the presentation of antigen. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cells proliferation and the potential development of GVHD. In order to effectively use allogeneic cells, the inventors inactivate the TCRalpha or TCRbeta gene which results in the elimination of the TCR from the surface of T-cells and thus prevent recognition of alloantigen and thus GVHD.

Although outstanding progress has been made in the fields of cancer detection and tumor cell biology, the treatment of late-stage and metastatic cancer remains a major challenge. Cytotoxic chemotherapy agents remain among the most used and successfully employed anti-cancer treatments. Several cytotoxic agents such as anti-metabolites, alkylating agents, anthracyclines, DNA methyltransferase inhibitors, platinum compounds and spindle poisons have been developed to kill cancer cells. However, they are not uniformly effective, and the introduction of these agents with novel therapies, such as immunotherapies, is problematic. For example, chemotherapy agents can be detrimental to the establishment of robust anti-tumor immunocompetent cells due to the agents' non-specific toxicity profiles. Small molecule-based therapies targeting cell proliferation pathways may also hamper the establishment of anti-tumor immunity. However, if chemotherapy regimens that are transiently effective can be combined with novel immunocompetent cell therapies then significant improvement in anti-neoplastic therapy might be achieved (for review (Dasgupta, McCarty et al. 2011)). Thus, to use "off-the-shelf" allogeneic therapeutic cells in conjunction with chemotherapy, the inventors develop a method of engineering allogeneic T-cell resistant to chemotherapeutic agents. The therapeutic benefits afforded by this strategy should be enhanced by the synergistic effects between chemotherapy and immunotherapy. Moreover, drug resistance can also benefit from the ability to selectively expand the engineered T-cell thereby avoiding the problems due to inefficient gene transfer to these cells.

SUMMARY OF THE INVENTION

In one aspect, the present invention provides methods for engineering immune cells to make them resistant to purine nucleotide analogs (PNA) chemotherapy drugs, such a clorofarabine et fludarabine, so that they can be used in cancer immunotherapy treatments in patients pre-treated with conventional chemotherapies. The immune cells can originate from the patient, such as in the case of TIL (Tumor Infiltrating Lymphocytes), in view of operating autologous treatments, or from donors in view of producing allogeneic cells, which can be used in allogeneic treatments.

In the later case, when the immune cells are T-cells, the present invention also provides methods to engineer T-cells that are made both resistant to chemotherapy drugs and allogeneic. Such methods comprise the step of inactivating at least one gene encoding a T-Cell Receptor (TCR) component, in particular TCRalpha, TCRbeta genes, in addition to the inactivation of a drug sensitizing gene, such as dcK and HPRT genes.

According to another aspect, the resistance to drugs can be conferred to a T-cell by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell according to the invention.

The present invention encompasses the isolated cells or cell lines obtainable by the method of the invention, more particularly isolated immune cells comprising any of the proteins, polypeptides, allelic variants, altered or deleted genes or vectors described herein.

The immune cells of the present invention or cell lines can further comprise exogenous recombinant polynucleotides, in particular CARs or suicide genes or they can comprise altered or deleted genes coding for checkpoint proteins or ligands thereof that contribute to their efficiency as a therapeutic product, ideally as an "off the shelf" product. In another aspect, the present invention concerns the method for treating or preventing cancer in the patient by administrating an engineered immune cell obtainable by the above methods.

FIG. 1 corresponds to a schematic representation of pathways and cellular toxicity of purine nucleoside analogs (PNAs); the inactivation of the enzyme deoxycytidine kinase (dCK) confers resistance to the drugs clofarabine and fludarabine;

FIG. 2 shows that the inactivation of the enzyme hypoxanthine-guanine phosphoribosyltransferase (HPRT) confers resistance to the drugs 6-Mercaptopurine (6MP) and 6 thio-guanine (6TG);

FIG. 3 depicts the overall dCK gene architecture in terms of exons and introns, and FIG. 4 shows the workflow followed to generate and to characterize HPRT KO T cells; D0 represents Day 0, Dn represents Day n; T7 corresponds to the endo T7 assay;

FIG. 5 represents the results obtained from endo T7 assay to check the processing of the dCK gene; the upper band corresponds to the non processed WT dCK gene and the 2 lower bands correspond to the processed dCK gene;

FIG. 6 represents cell expansion of dCK KO T-cells treated with 5 µg or 10 µg of mRNA encoding dCK2 TALE-nuclease and WT T-cells controls 1 and 2 over a period of 14 days after electroporation.

Figure 10:
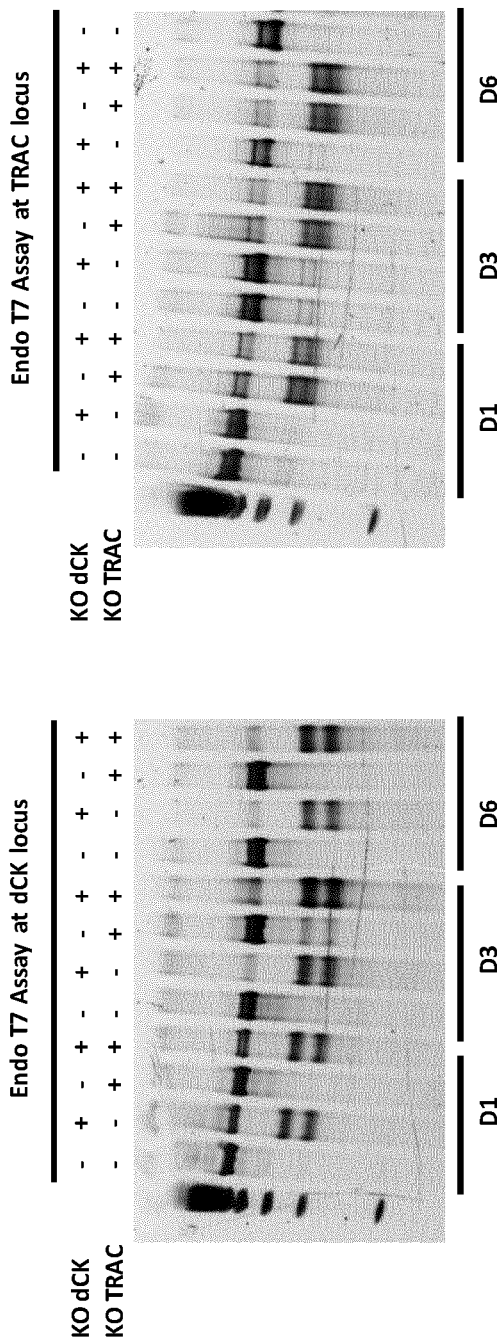
Figure 11:
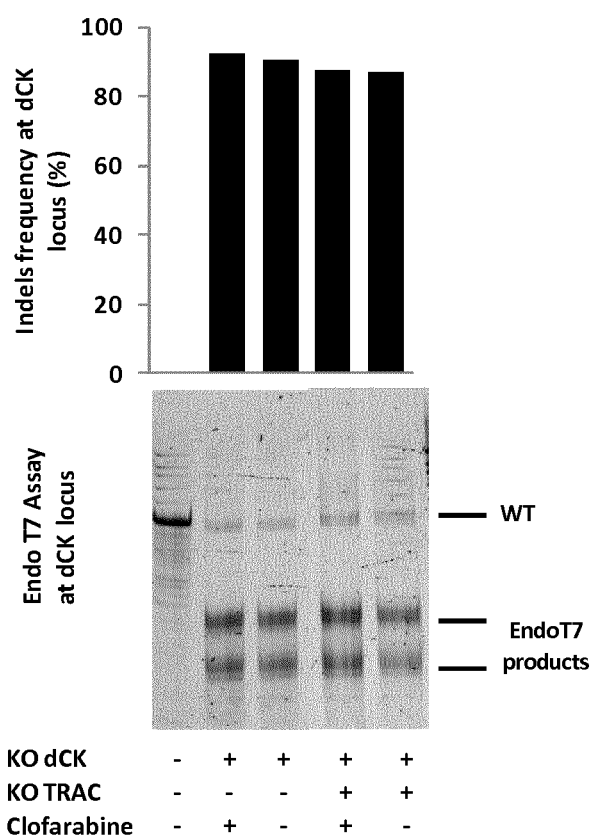
Figure 12:
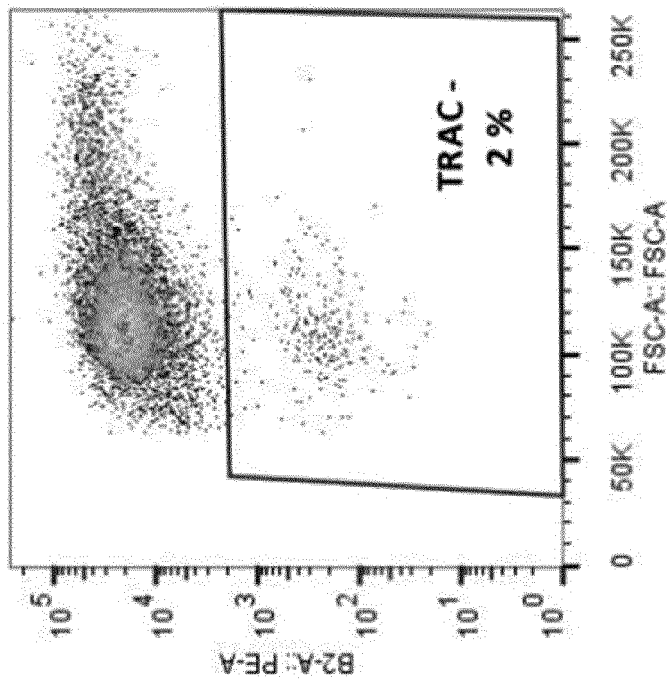
Figure 12:
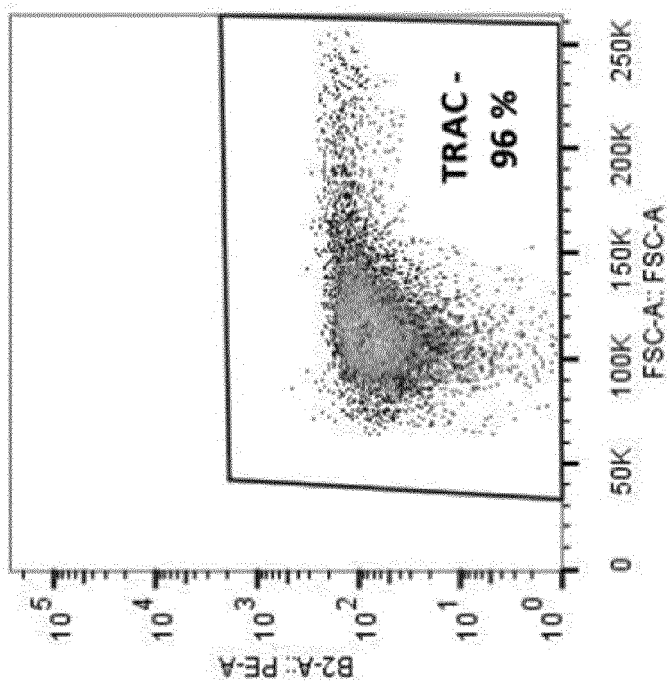
Figure 12:
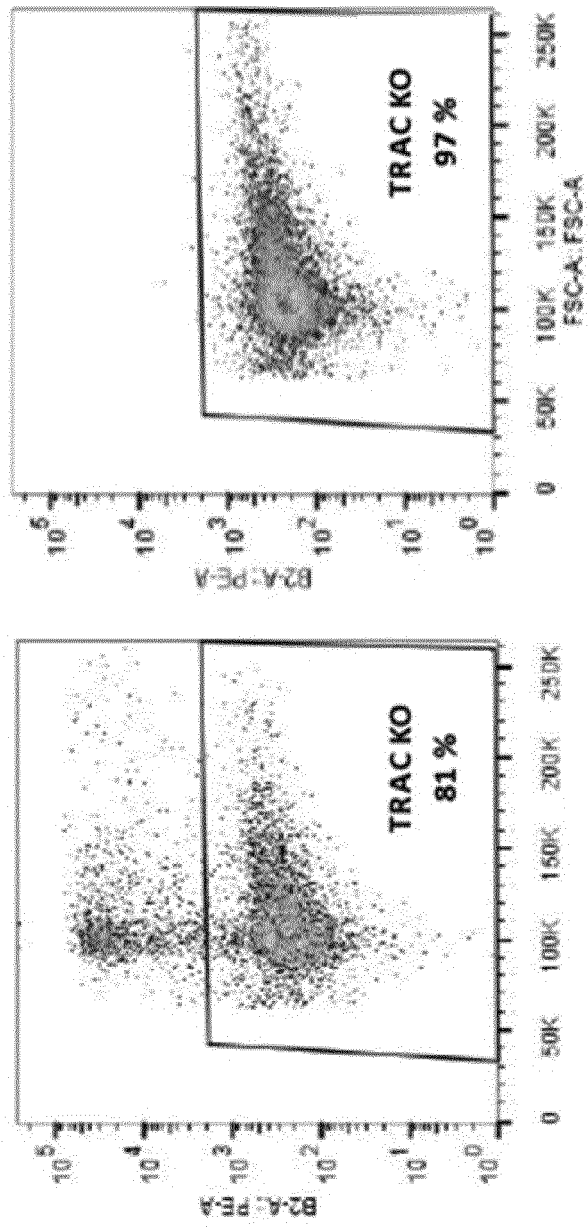
Figure 12:
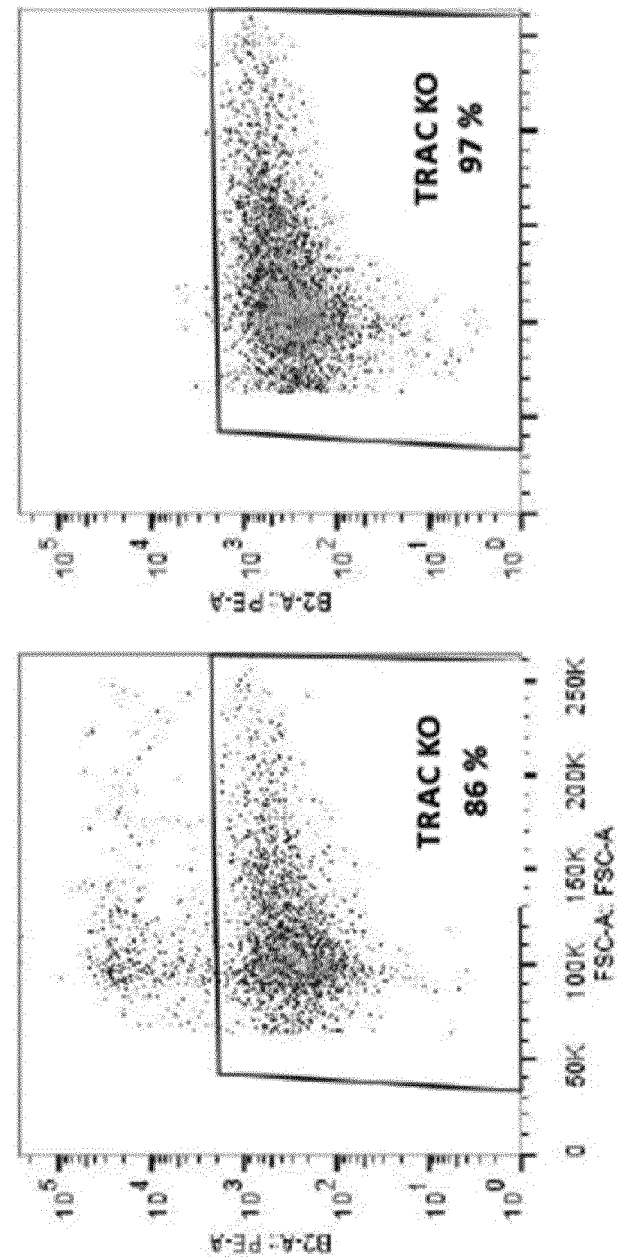
Figure 13:
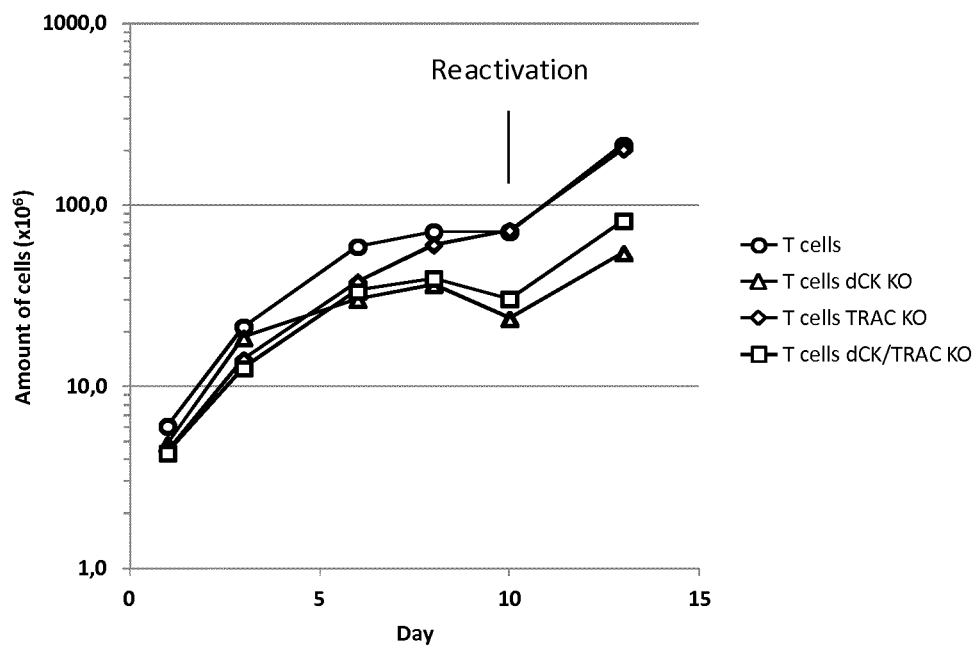
Figure 14:
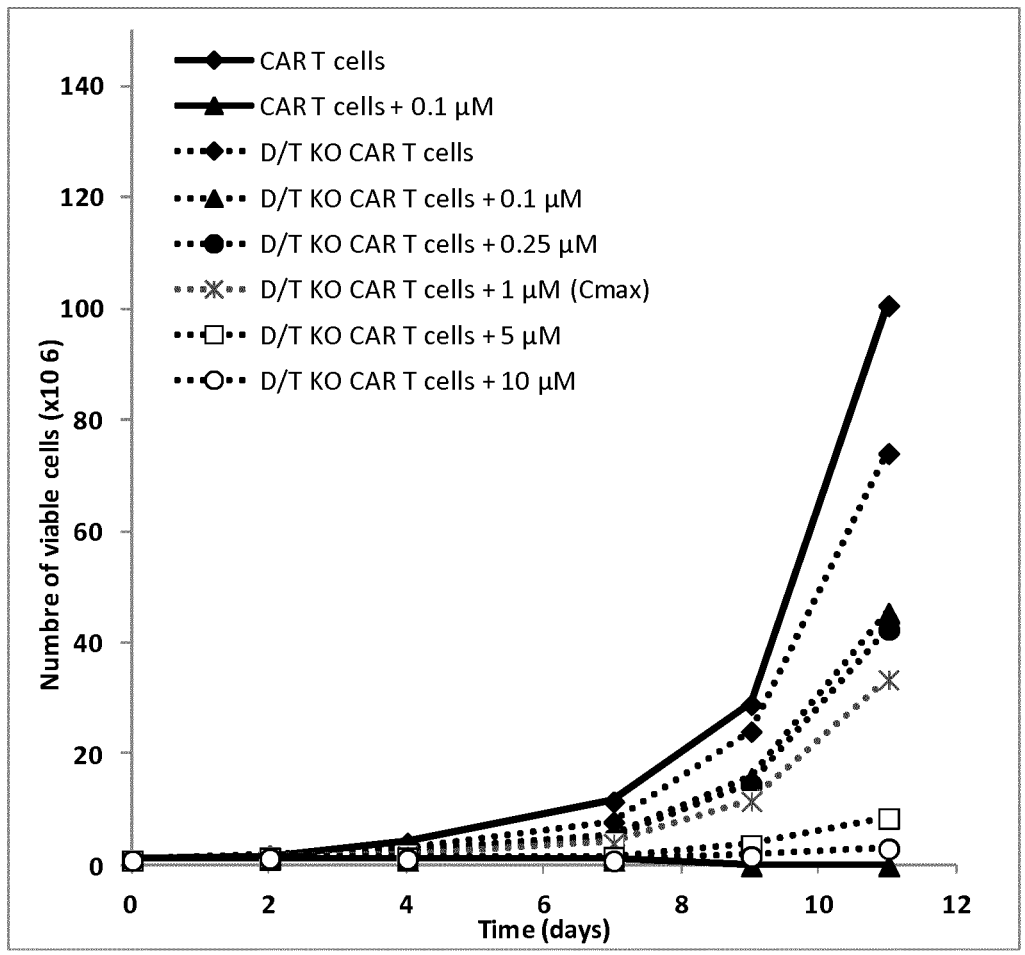
Figure 15:
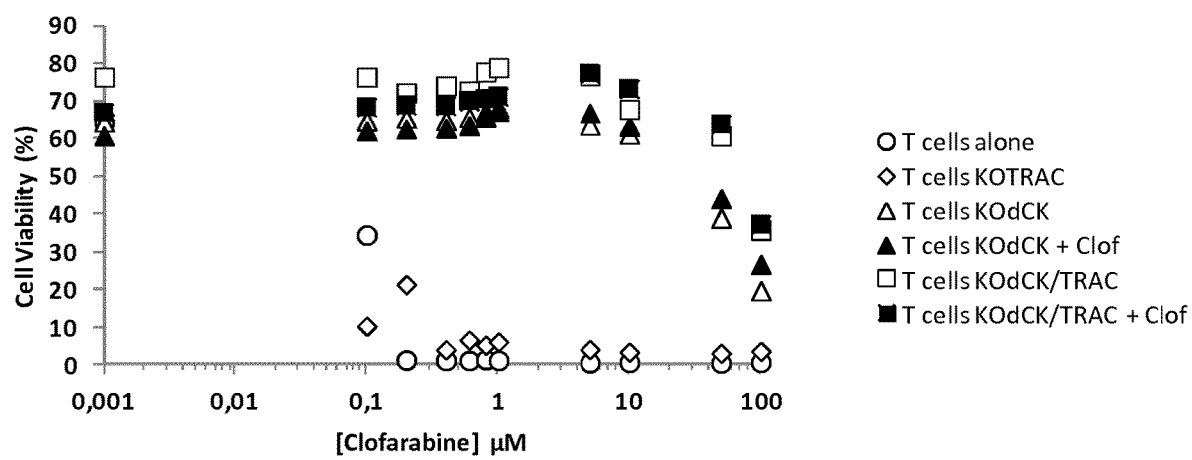
Figure 16:
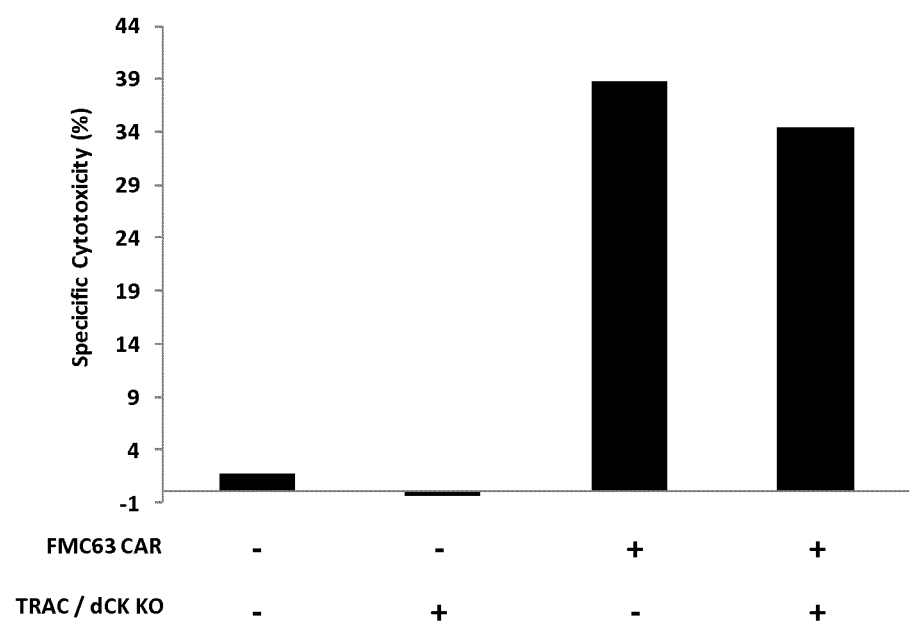
Figure 17:
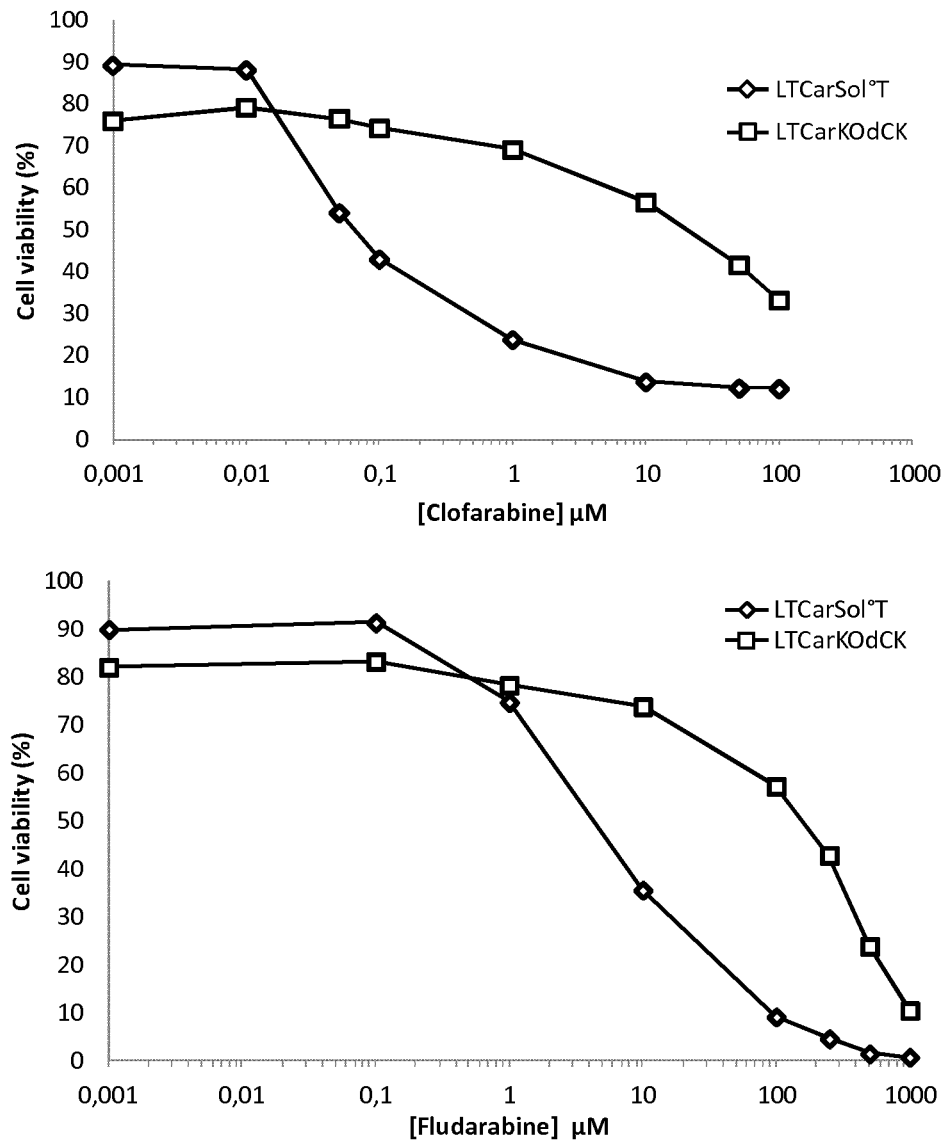
Figure 18:
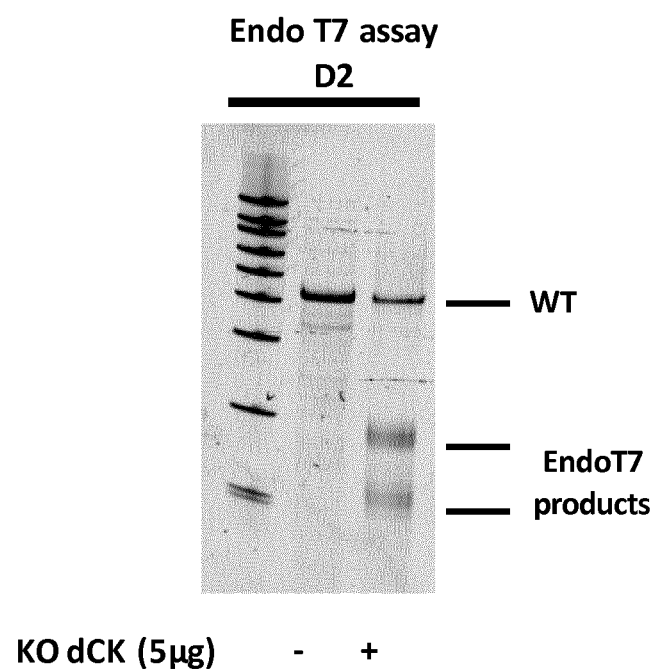
Figure 19:
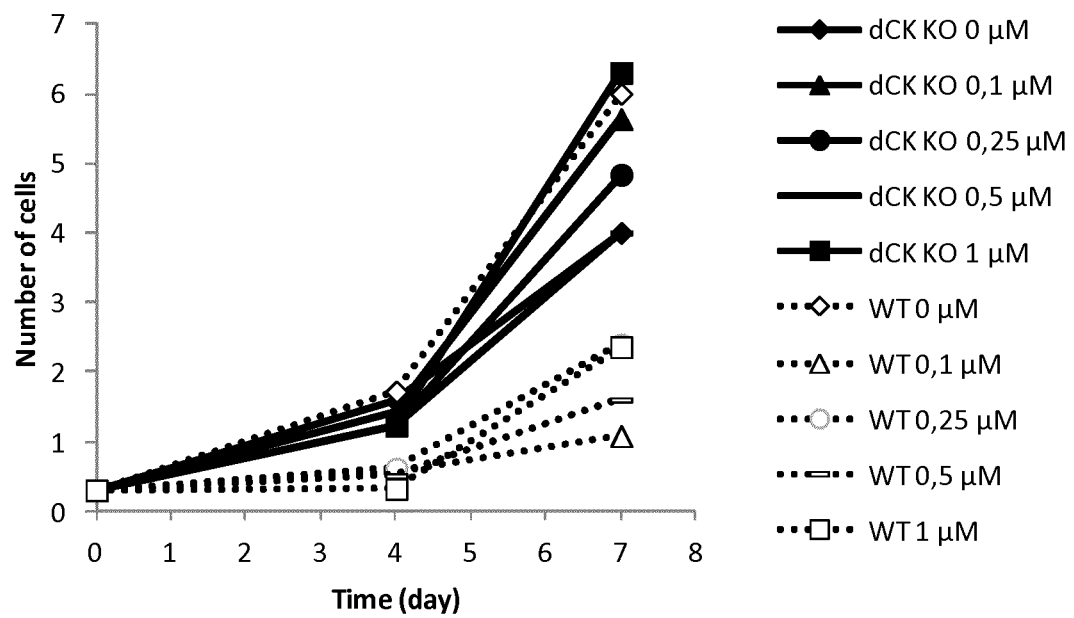
Figure 20:
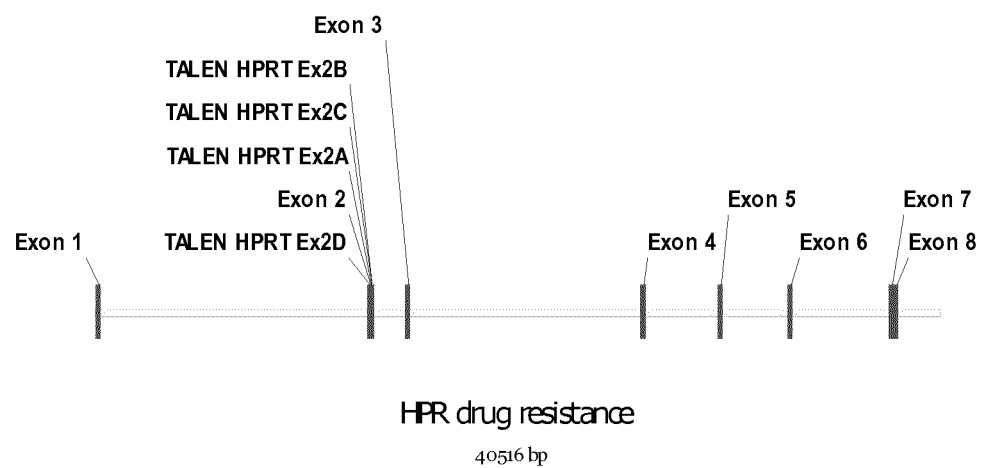
Figure 21:
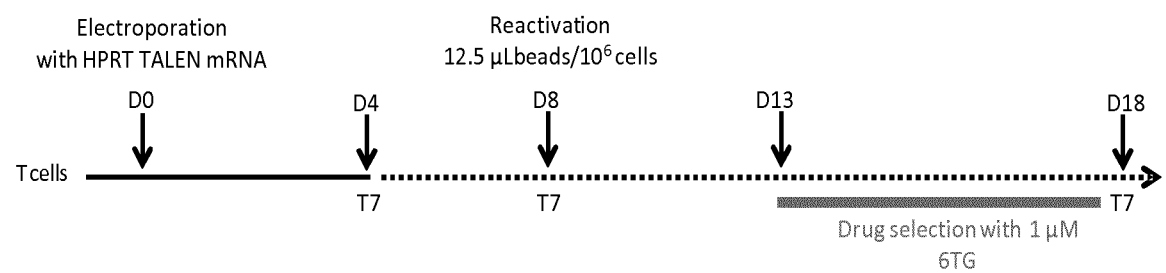
Figure 22:
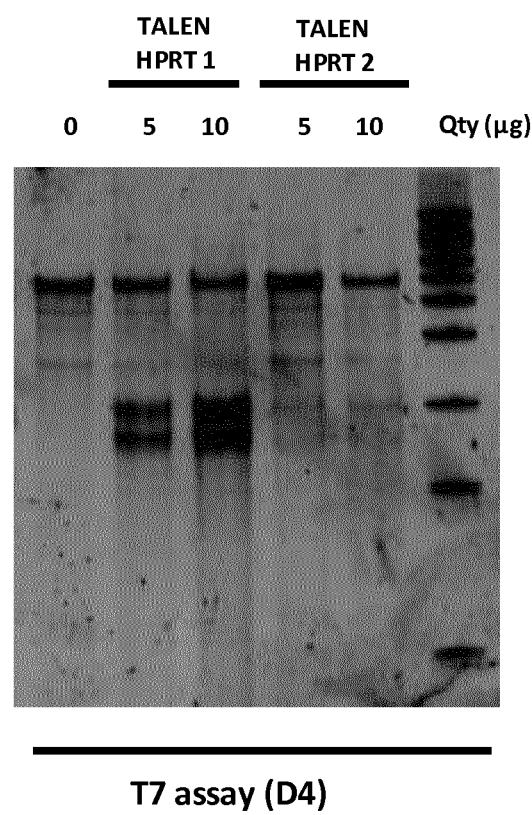
Figure 23:
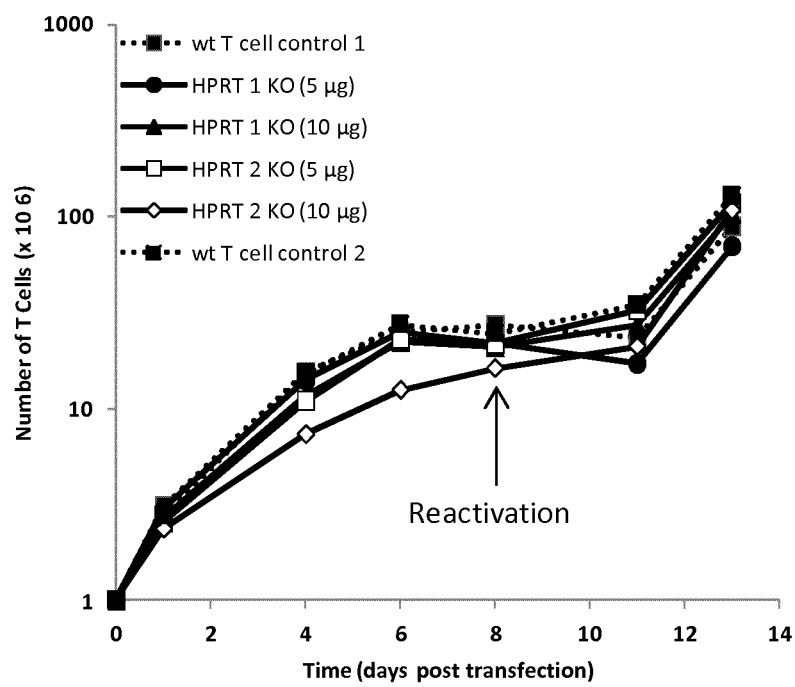
Figure 24:
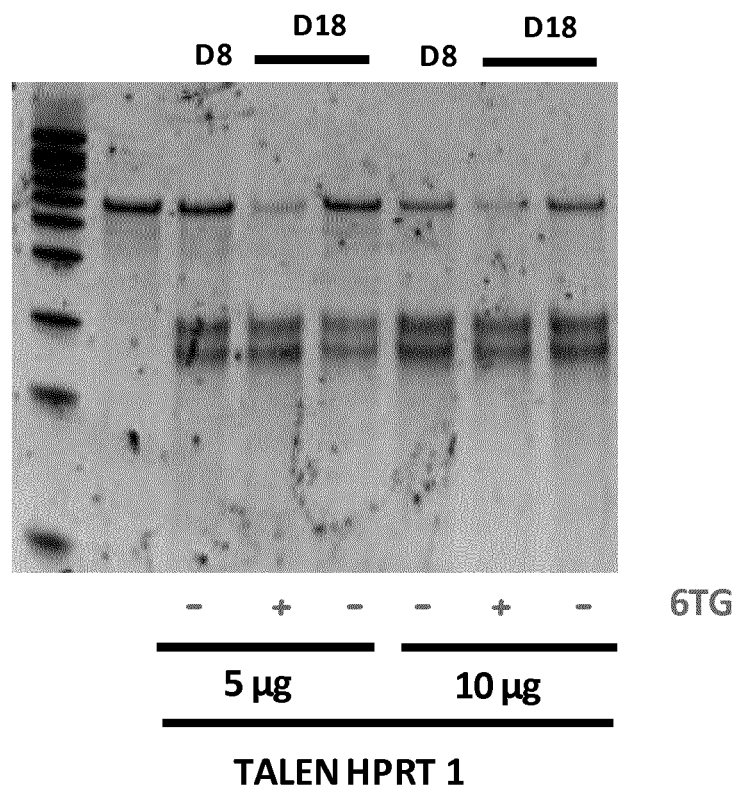
Figure 25:
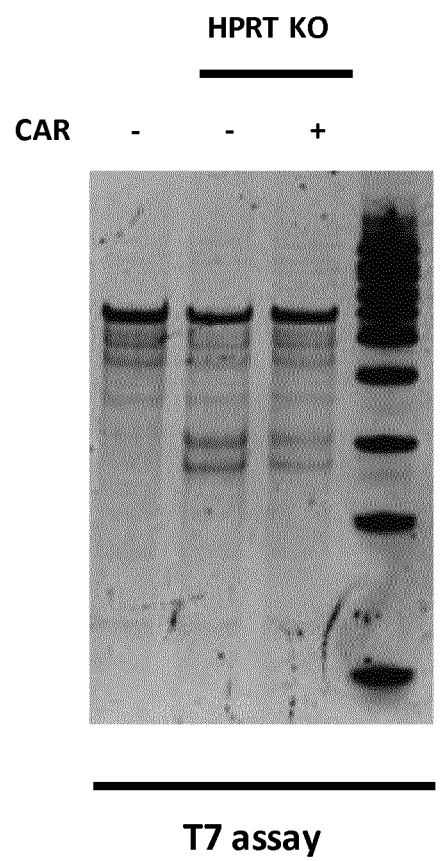
Figure 26:
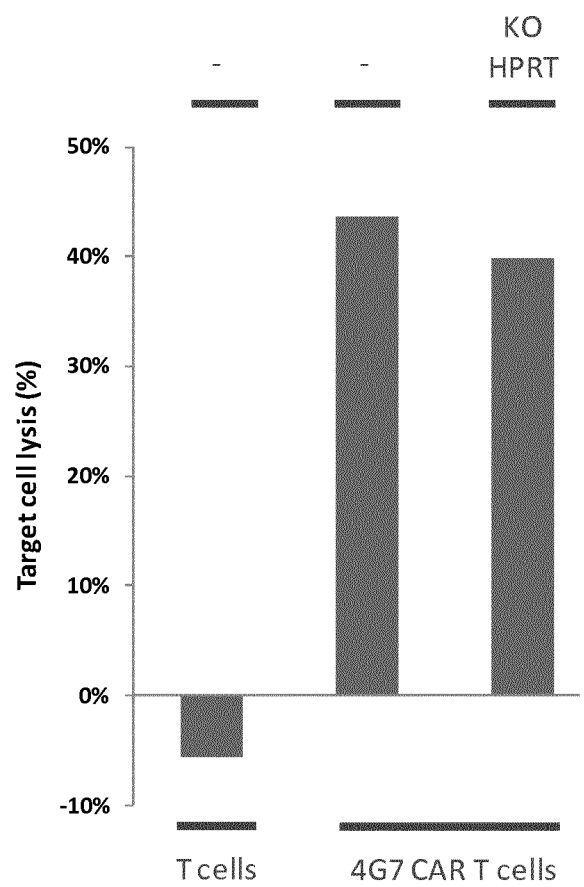
Figure 27:
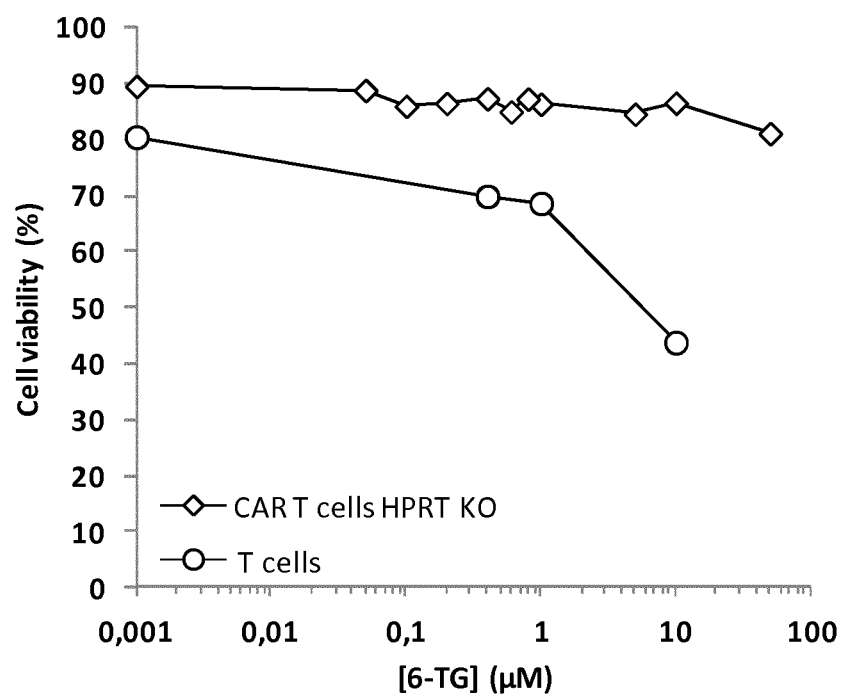

FIG. 10 corresponds to an endo T7 assay to check genetically the efficacy of double KO dCK/TRAC in T-cells at different times after electoporation (D1, D3 and D6). The primers used for each locus are presented in the example, for simple KO dCK T-cell (+−) and simple KO TRAC T-cell (−+), double KO dCK/TRAC T-cells (++) and WT T cells (−−); the lower bands mean a correct dCK and TRAC gene processing;

FIG. 11 corresponds to an endo T7 assay and deep sequencing data to check the efficacy of dCK inactivation in the presence (+) or in the absence (−) of clofarabine, with (+) or without (−) TRAC inactivation, the legend is the same than in FIG. 10; the indel frequency was performed to evaluate the rate of insertions/deletions at the dCK locus;

FIG. 12A represents the labeling control experiment performed with T cells in the presence (labeled T cells) or in the absence of anti TCR mAb-PE (unlabeled T cells);

FIG. 12B monitors the TCAR negative cells collected after incubation in the presence or in the absence of clofarabine, before and after TRAC KO T cells purification. These cells were also inactivated for dCK gene;

FIG. 13 shows growth rate for simple KO dCK and TRAC T-cells and double KO dCK/TRAC T cells versus WT T-cells in the absence of clofarabine for a period of 12 days after electroporation;

FIG. 14 shows growth rate curves of dCK/TCAR double KO CAR T-cells in media having different clofarabine doses (from 0.1 to 10 µM) compared to CAR T cells (with or without clofarabine) for a period of 11 days;

FIG. 15 shows percentage of cell viability for simple KO dCK or TRAC T cells, double KO dCK/TCAR T-cells versus WT T-cells in media having different clofarabine doses (from 1 nM to 100 µM); this graph allows the determination of IC50 for clofarabine on each T cells population;

FIG. 16 represents the percentage of specific cytotoxicity for the double KO TRAC/dCK CAR T cells compared to the CAR FMC63 T cells (both expressing the CD19 antigen) versus double KO TRAC/dCK T cells (without CAR, so does not express CD19 antigen) and WT T cells (no KO and no CAR);

FIG. 17 shows the percentage of cell viability for double KO dCK/TCAR CAR T-cells versus CAR T-cells control, when these T-cells were incubated in increasing doses of clofarabine (10 ng to 100 µg, upper graph), and fludarabine (10 µM to 100 µM, lower graph). These graphs allows determination of IC50 for both drugs clofarabine and fludarabine;

FIG. 18 corresponds to an endo T7 assay at Day 2 (D2) to check genetically the efficacy of dCK inactivation in Daudi cells (+) (5 µg of mRNA encoding dCK TALE-nuclease was used) versus WT cells (−). The upper band corresponds to the non processed dCK gene whereas the 2 lower bands to the products of dCK inactivation;

FIG. 19 represents the growth rate (expressed in ×10$^6$ cells) for a period of 7 days of KO dCK Daudi cells versus WT Daudi cells in the absence or presence of increasing amounts of clofarabine (0.1 to 1 µM);

FIG. 20 shows the overall HPRT gene architecture in terms of exons and introns) and location of different TALE-nuclease target sites (all of them in Exon 2);

FIG. 21 depicts the workflow which was used to generate and characterize HPRT KO T cells;

FIG. 22 represents an endo T7 assay to check HPRT gene inactivation in T cells by TALE-nuclease HPRT pairs n° 1 and T pair n° 2 (2 doses were tested: 5 μg and 10 μg), Day 4 (D4);

FIG. 23 represents the growth rate (expressed in $\times 10^6$ cells) for a period of 13 days of KO HPRT T cells, by using 5 or 10 μg of TALE-nuclease HPRT 1 pair (HPRT1) or TALE-nuclease HPRT 2 pair (HPRT2), versus WT T cells control 1 and control 2;

FIG. 24 represents an endo T7 assay to check HPRT gene inactivation in T cells using 5 or 10 μg TALE-nuclease HPRT pairs n° 1 (TALE-nuclease HPRT 1), versus WT T cells [symbolized par (−)] at D8 and D18, when these T-cells were incubated in 1 μM of the drug 6TG;

FIG. 25 represents an endo T7 assay to check HPRT gene inactivation in T cells in the presence or in the absence of 4G7 CAR, this assay was performed without 6TG selection;

FIG. 26 shows the percentage of specific cytotoxicity for the KO HPRT CAR T cells compared to the CAR 4G7 T cells (both expressing the CD19 antigen) and WT T cells (no KO and no CAR);

FIG. 27 shows the percentage of cell viability for KO HPRT CAR T-cells versus WT T cells in increasing doses of 6TG drug (10 ng to 50 μM).

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Drug Resistant T-Cells

The terms "therapeutic agent", "chemotherapeutic agent", or "drug" as used herein refers to a compound or a derivative thereof that can interact with a cancer cell, thereby reducing the proliferative status of the cell and/or killing the cell. Examples of chemotherapeutic agents include, but are not limited to, alkylating agents (e.g., cyclophosphamide, ifosamide), metabolic antagonists (e.g., purine nucleoside antimetabolite such as clofarabine, fludarabine or 2'-deoxyadenosine, methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

As used herein, a cell which is "resistant or tolerant" to an agent means a cell which has been genetically modified so that the cell proliferates in the presence of an amount of an agent that inhibits or prevents proliferation of a cell without the modification.

Expression of Drug Resistance Genes

In a particular embodiment, said drug resistance can be conferred to the T-cell by the expression of at least one drug resistance gene. Said drug resistance gene refers to a nucleic acid sequence that encodes "resistance" to an agent, such as a chemotherapeutic agent (e.g. methotrexate). In other words, the expression of the drug resistance gene in a cell permits proliferation of the cells in the presence of the agent to a greater extent than the proliferation of a corresponding cell without the drug resistance gene. A drug resistance gene of the invention can encode resistance to antimetabolite, methotrexate, vinblastine, cisplatin, alkylating agents, anthracyclines, cytotoxic antibiotics, anti-immunophilins, their analogs or derivatives, and the like.

Several drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

One example of drug resistance gene can also be a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (SEQ ID NO: 14, GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 ((Schweitzer, Dicker et al. 1990); International application WO94/24277; U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide set forth in SEQ ID NO: 14. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (SEQ ID NO: 15; NP_000875.2) that lead to a significantly increased resistance to IMPDH inhibitor. The mutations are preferably at positions T333 and/or 5351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue. Correspondence of amino acid positions described herein is frequently expressed in terms of the positions of the amino acids of the form of wild-type human IMPDH2 polypeptide set forth in SEQ ID NO: 15.

Another drug resistance gene is the mutant form of calcineurin. Calcineurin (PP2B) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue of SEQ ID NO: 16. Correspondence of amino acid positions described herein is frequently expressed in terms of the positions of the amino acids of the form of wild-type human calcineurin heterodimer a polypeptide set forth in SEQ ID NO: 16 (GenBank: ACX34092.1).

In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagines at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence SEQ ID NO: 17. Correspondence of amino acid positions described herein is frequently expressed in terms of the positions of the amino acids of the form of wild-type human calcineurin heterodimer b polypeptide set forth in SEQ ID NO:17 (GenBank: ACX34095.1).

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, Kurpad et al. 1999). In a particular embodiment, AGT mutant form can comprise a mutated amino acid of the wild type AGT position P140, in the amino acid sequence SEQ ID NO: 18 (UniProtKB: P16455). In a preferred embodiment, said proline at position 140 is replaced with a lysine residue.

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (NP_000918).

Drug resistance gene can also be cytotoxic antibiotics, such as ble gene or mcrA gene. Ectopic expression of ble gene or mcrA in an immune cell gives a selective advantage when exposed to the chemotherapeutic agent, respectively the bleomycine or the mitomycin C.

The most practical approach to gene therapy is the addition of a gene to engineer T-cell by using efficient gene delivery with vectors, preferably viral vector. Thus, in a particular embodiment, said drug resistance gene can be expressed in the cell by introducing a transgene preferably encoded by at least one vector into a cell.

The random insertion of genes into the genome may lead to the inappropriate expression of the inserted gene or the gene near the insertion site. Specific gene therapy using homologous recombination of exogenous nucleic acid comprising endogenous sequences to target genes to specific sites within the genome can allow engineering secure T-cells. As described above, the genetic modification step of the method can comprise a step of introduction into cells of an exogeneous nucleic acid comprising at least a sequence encoding the drug resistance gene and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Endonucleolytic breaks are known to stimulate the rate of homologous recombination. Thus, in a particular embodiment, the method of the invention further comprises the step of expressing in the cell a rare-cutting endonuclease which is able to cleave a target sequence within an endogenous gene. Said endogenous gene can encode for examples DHFR, IMPDH2, calcineurin or AGT. Said rare-cutting endonuclease can be a TALE-nuclease, a Zinc finger nuclease, a CRISPR/Cas9 endonuclease, a MBBBD-nuclease or a meganuclease.

Inactivation of Drug Sensitizing Genes

In another particular embodiment, said drug resistance can be conferred to the T-cell by the inactivation of a drug sensitizing gene. For the first time, the inventor sought to inactivate potential drug sensitizing gene to engineer T-cell for immunotherapy.

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, the step of inactivating at least one drug sensitizing gene comprises introducing into the cell a rare-cutting endonuclease able to disrupt at least one drug sensitizing gene. In a more particular embodiment, said cells are transformed with nucleic acid encoding a rare-cutting endonuclease capable of disrupting a drug sensitizing gene, and said rare-cutting endonuclease is expressed into said cells. Said rare-cutting endonuclease can be a meganuclease, a Zinc finger nuclease, CRISPR/Cas9 nuclease, A MBBBD-nuclease or a TALE-nuclease. In a preferred embodiment, said rare-cutting endonuclease is a TALE-nuclease.

Figure 1:
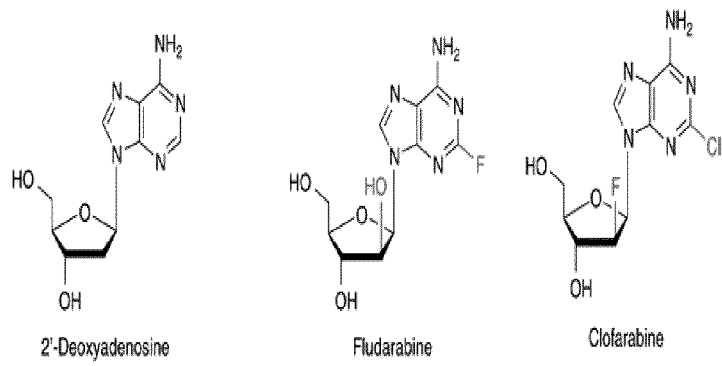
Figure 1:
Figure 1:
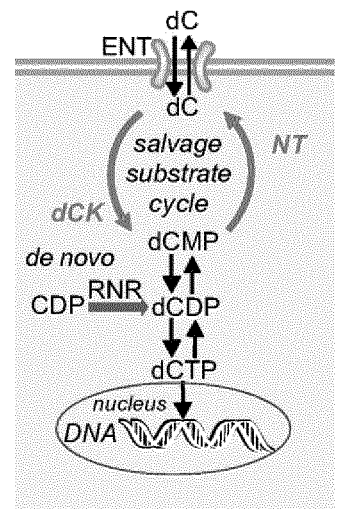

In a preferred embodiment, drug sensitizing gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production (cf presumed mechanism of action in FIG. 1).

Preferably, the inactivation of dCK in T cells is mediated by TALE nuclease. To achieve this goal, several pairs of dCK TALE-nuclease have been designed, assembled at the polynucleotide level and validated by sequencing. Examples of TALE-nuclease pairs which can be used according to the invention are depicted by SEQ ID No 63 and SEQ ID No 64. When this pair of TALE-nuclease is used, the dCK target sequence corresponds to SEQ ID No 62.

As shown in the examples, this dCK inactivation in T cells confers resistance to purine nucleoside analogs (PNAs) such as clofarabine and fludarabine.

In another preferred embodiment, the dCK inactivation in T cells is combined with an inactivation of TRAC genes rendering these double knock out (KO) T cells both resistant to drug such as clofarabine and allogeneic. This double features is particularly useful for a therapeutic goal, allowing "off-the-shelf" allogeneic cells for immunotherapy in conjunction with chemotherapy to treat patients with cancer. This double KO inactivation dCK/TRAC can be performed simultaneously or sequentially. One example of TALE-nuclease dCK/TRAC pairs which gave success in the invention is the use of SEQ ID No 63 and SEQ ID No 64 and SEQ ID No 66 and No 67 respectively, The target sequences in the 2 loci (dCK and TRAC) are depicted in SEQ ID No 62 and SEQ ID No 65 respectively.

Figure 2:
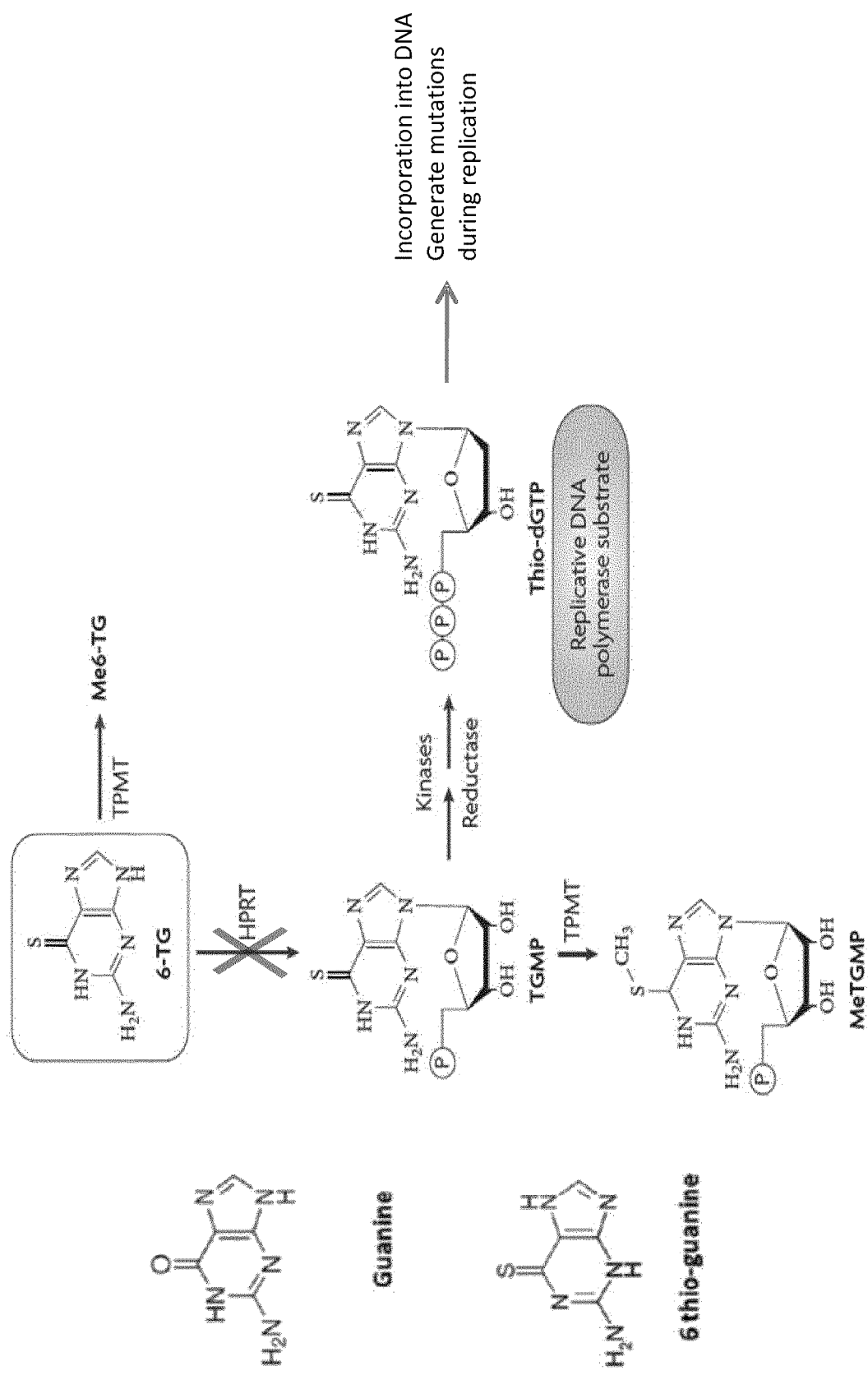

Another example of enzyme which can be inactivated is human hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Guanines analogs are metabolized by HPRT transferase that catalyzes addition of phosphoribosyl moiety and enables the formation of TGMP (FIG. 2). Guanine analogues including 6 mercapthopurine (6MP) and 6 thioguanine (6TG) are usually used as lymphodepleting drugs to treat ALL. They are metabolized by HPRT (hypoxanthine phosphoribosyl transferase that catalyzes addition of phosphoribosyl moiety and enables formation TGMP. Their subsequent phosphorylations lead to the formation of their triphosphorylated forms that are eventually integrated into DNA. Once incorporated into DNA, thio GTP impairs fidelity of DNA replication via its thiolate groupment and generate random point mutation that are highly deleterious for cell integrity.

In another embodiment, the inactivation of the CD3 normally expressed at the surface of the T-cell can confer resistance to anti-CD3 antibodies such as teplizumab.

CD19+/Luc+ Drug Resistant Daudi Cells for Testing the Cytotoxicity of by Drug Resistant Allogenic CAR T Cells The present invention encompasses also a method for manufacturing target cells which express both a surface receptor specific to the CAR T cells and a resistance gene. These target cells are particularly useful for testing the cytoxicity of CAR T cells. These cells are readily resistant to clinically relevant dose of clofarabine and harbor lupciferase activity. This combination of features enable traking them in vivo in a mice model. More particularly, they can be used to assess the cytotoxicity properties drug resistant T cells in mice in the presence of clofarabine or other PNAs. Clofarabine resistant Daudi cells mimick the physiological state of acute lymphoblastic leukemia (ALL) patients relapsing form induction therapy, that harbor drug resistant B cell malignancies. Thus, these cells are of great interest to evaluate the reliability and cytotoxicity of drug resistant CAR T cells. Preferably, these target cells are CD19+ Luciferase+ Daudi cells. Isolated cell The present invention also relates to an isolated cell obtainable by the method described above. In particular, the present invention relates to an isolated T-cell resistant to a drug which comprises at least one disrupted gene encoding a T-cell receptor component. In a particular embodiment, said T-cell expresses at least one drug resistance gene, preferably ble gene or mcrA gene or gene encoding a mutant DHFR, a mutant IMPDH2, a mutant AGT or a mutant calcineurin. In another particular embodiment, said T-cell comprises at least one disrupted drug sensitizing gene such as dCK or HPRT gene. In a more particular embodiment, said isolated T-cell comprises a disrupted HPRT gene and express a DHFR mutant; said isolated T-cell comprises a disrupted HPRT gene and express a IMPDH2 mutant; said isolated T-cell comprises a disrupted HPRT gene and express a calcineurin mutant; said isolated T-cell comprises a disrupted HPRT gene and express a AGT mutant. In another preferred embodiment, the said isolated cell expresses a Chimeric Antigen Receptor (CAR), which can be CD19 or CD123.

Allogeneic T-Cell Resistant to a Drug

In particular, the present invention relates to an allogeneic T-cell resistant to a drug, specifically suitable for immunotherapy. The resistance of a drug can be confer by inactivation of drug sensitizing genes or by expression of drug resistance genes such as previously described. Some examples of drugs which suit to the invention are the purine nucleoside analogues (PNAs) such as clofarabine or fludarabine, or other drugs such as 6-Mercaptopurine (6MP) and 6 thio-guanine (6TG).

Cell according to the present invention refers to a cell of hematopoietic origin functionally involved in the initiation and/or execution of innate and/or adaptative immune response. Cell according to the present invention is preferably a T-cell obtained from a donor. Said T cell according to the present invention can be derived from a stem cell. The stem cells can be adult stem cells, embryonic stem cells, more particularly non-human stem cells, cord blood stem cells, progenitor cells, bone marrow stem cells, totipotent stem cells or hematopoietic stem cells. Representative human stem cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T-cell lines available and known to those skilled in the art, may be used. In another embodiment, said cell is preferably derived from a healthy donor. In another embodiment, said cell is part of a mixed population of cells which present different phenotypic characteristics.

Multiple Drug Resistance

In another particular embodiment, the inventors sought to develop an "off-the shelf" immunotherapy strategy, using allogeneic T-cells resistant to multiple drugs to mediate selection of engineered T-cells when the patient is treated with different drugs. The therapeutic efficiency can be significantly enhanced by genetically engineering multiple drug resistance allogeneic T-cells. Such a strategy can be particularly effective in treating tumors that respond to drug combinations that exhibit synergistic effects. Moreover multiple resistant engineered T-cells can expand and be selected using minimal dose of drug agents.

Thus, the method according to the present invention can comprise modifying T-cell to confer multiple drug resistance to said T-cell. Said multiple drug resistance can be conferred by either expressing more than one drug resistance gene or by inactivating more than one drug sensitizing gene. In another particular embodiment, the multiple drug resistance can be conferred to said T-cell by expressing at least one drug resistance gene and inactivating at least one drug sensitizing gene. In particular, the multiple drug resistance can be conferred to said T-cell by expressing at least one drug resistance gene such as mutant form of DHFR, mutant form of IMPDH2, mutant form of calcineurin, mutant form of MGMT, the ble gene, and the mcrA gene and inactivating at least one drug sensitizing gene such as HPRT gene. In a preferred embodiment, multiple drug resistance can be conferred by inactivating HPRT gene and expressing a mutant form of DHFR; or by inactivating HPRT gene and expressing a mutant form of IMPDH2; or by inactivating HPRT gene and expressing a mutant form of calcineurin; by inactivating HPRT gene and expressing a mutant form of MGMT; by inactivating HPRT gene and expressing the ble gene; by inactivating HPRT gene and expressing the mcrA gene.

Method of Engineering Drug Resistance Allogeneic T-Cells:

To improve cancer therapy and selective engraftment of allogeneic T-cells, drug resistance is conferred to said cells to protect them from the toxic side effects of chemotherapy agent. The drug resistance of T-cells also permits their enrichment in or ex vivo, as T-cells which express the drug resistance gene will survive and multiply relative to drug sensitive cells. In particular, the present invention relates to a method of engineering allogeneic and drug resistance T-cells resistant for immunotherapy comprising:

(a) Providing a T-cell;
(b) Selecting at least one drug;
(c) Modifying said T-cell by inactivating at least one gene encoding a T-cell receptor (TCR) component;
(d) Modifying T-cell to confer drug resistance to said T-cell;
(e) Expanding said engineered T-cell in the presence of said drug.

Allogeneic T-Cells

The present invention relates to allogeneic immunotherapy. Engraftment of allogeneic T-cells is possible by inactivating at least one gene encoding a TCR component. TCR is rendered not functional in the cells by inactivating TCR alpha gene and/or TCR beta gene(s). TCR inactivation in allogeneic T-cells avoids GvHD. By inactivating a gene it is intended that the gene of interest is not expressed in a functional protein form. In particular embodiments, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art. In a particular embodiment, the step of inactivating at least a gene encoding a component of the T-cell receptor (TCR) into the cells of each individual sample comprises introducing into the cell a rare-cutting endonuclease able to disrupt at least one gene encoding a component of the T-cell receptor (TCR). In a more particular embodiment, said cells of each individual sample are transformed with nucleic acid encoding a rare-cutting endonuclease capable of disrupting at least one gene encoding a component of the T-cell receptor (TCR), and said rare-cutting endonuclease is expressed into said cells.

Said rare-cutting endonuclease can be a meganuclease, a Zinc finger nuclease, CRISPR/Cas9 nuclease, a TALE-nuclease or a MBBBD-nuclease. In a preferred embodiment, said rare-cutting endonuclease is a TALE-nuclease. By TALE-nuclease is intended a fusion protein consisting of a DNA-binding domain derived from a Transcription Activator Like Effector (TALE) and one nuclease catalytic domain to cleave a nucleic acid target sequence (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012). In the present invention new TALE-nucleases have been designed for precisely targeting relevant genes for adoptive immunotherapy strategies.

Preferred TALE-nucleases according to the invention are those recognizing and cleaving the target sequence selected from the group consisting of: SEQ ID NO: 1 to 5 (TCRalpha), SEQ ID NO: 6 and 7 (TCRbeta). Said TALE-nucleases preferably comprise a polypeptide sequence selected from SEQ ID NO: 8 to SEQ ID NO: 13. In another embodiment, additional catalytic domain can be further introduced into the cell with said rare-cutting endonuclease to increase mutagenesis in order to enhance their capacity to inactivate targeted genes. In particular, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX2 polypeptide. Said additional catalytic domain may be fused to a nuclease fusion protein or chimeric protein according to the invention optionally by a peptide linker.

Endonucleolytic breaks are known to stimulate the rate of homologous recombination. Thus, in another embodiment, the genetic modification step of the method further comprises a step of introduction into cells of an exogeneous nucleic acid comprising at least a sequence homologous to a portion of the target nucleic acid sequence, such that homologous recombination occurs between the target nucleic acid sequence and the exogeneous nucleic acid. In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogeneous nucleic acid. Preferably, homologous sequences of at least 50 bp, preferably more than 100 bp and more preferably more than 200 bp are used within said donor matrix. In a particular embodiment, the homologous sequence can be from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

In a particular embodiment, said exogenous nucleic acid can comprise a transgene encoding for the drug resistance gene according to the present invention.

Engineering of Further Possible T-Cells Attributes

The immune cells according to the invention may be further engineered to acquire additional attributes that participate to their more specific or efficient therapeutic use.

Chimeric Antigen Receptors

Chimeric Antigen Receptors (CAR) are able to redirect immune cell specificity and reactivity toward a selected target exploiting the ligand-binding domain properties. Thus, in another particular embodiment, the method further comprises a step of introducing into said lymphocytes a Chimeric Antigen Receptor. Said Chimeric Antigen Receptor combines a binding domain against a component present on the target cell, for example an antibody-based specificity for a desired antigen (e.g., tumor antigen) with a T-cell receptor-activating intracellular domain to generate a chimeric protein that exhibits a specific anti-target cellular immune activity. Generally, CAR consists of an extracellular single chain antibody (scFv) fused to the intracellular signaling domain of the T-cell antigen receptor complex zeta chain (scFv:ξ) and have the ability, when expressed in T-cells, to redirect antigen recognition based on the monoclonal antibody's specificity. One example of CAR used in the present invention is a CAR directing against CD19 antigen and can comprise as non limiting example the amino acid sequence: SEQ ID NO: 19 or 20.

Inactivation of Immune-Checkpoint Genes

T-cell-mediated immunity includes multiple sequential steps involving the clonal selection of antigen specific cells, their activation and proliferation in secondary lymphoid tissue, their trafficking to sites of antigen and inflammation, the execution of direct effector function and the provision of help (through cytokines and membrane ligands) for a multitude of effector immune cells. Each of these steps is regulated by counterbalancing stimulatory and inhibitory signal that fine-tune the response. It will be understood by those of ordinary skill in the art, that the term "immune checkpoints" means a group of molecules expressed by T-cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), LAIR1 (also known as CD305, GenBank accession number: CR542051.1, (Meyaard, Adema et al. 1997)), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7 (Nicoll, Ni et al. 1999), SIGLEC9 (Zhang, Nicoll et al. 2000; Ikehara, Ikehara et al. 2004), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF (Quigley, Pereyra et al. 2010), GUCY1A2, GUCY1A3, GUCY1B2, GUCY1B3 which directly inhibit immune cells. For example, CTLA-4 is a cell-surface protein expressed on certain CD4 and CD8 T-cells; when engaged by its ligands (B7-1 and B7-2) on antigen presenting cells, T-cell activation and effector function are inhibited. Thus the present invention relates to a method of engineering allogeneic T-cell resistant to drug, further comprising modifying T-cells by inactivating at least one protein involved in the immune check-point, in particular PD1 and/or CTLA-4. In a preferred embodiment, the step of inactivating at least one protein involved in the immune checkpoint is realized by expressing a rare-cutting endonuclease able to specifically cleave a target sequence within the immune checkpoint gene. In a preferred embodiment, said rare-cutting endonuclease is a TALE-nuclease. For example said TALE-nuclease can specifically cleave the target sequence selected from the group consisting of: SEQ ID NO: 21 to 23 (CTLA-4) and SEQ ID NO: 24 and SEQ ID NO: 25 (PDCD1), and in a more preferred embodiment said TALE-nuclease comprises amino acid sequence selected from the group consisting of SEQ ID NO: 26 to SEQ ID NO: 35.

Immunosuppressive Resistant T Cells

Allogeneic cells are rapidly rejected by the host immune system. It has been demonstrated that, allogeneic leukocytes present in non-irradiated blood products will persist for no more than 5 to 6 days (Boni, Muranski et al. 2008). Thus, to prevent rejection of allogeneic cells, the host's immune system has to be usually suppressed to some extent. However, in the case of adoptive immunotherapy the use of immunosuppressive drugs also have a detrimental effect on the introduced therapeutic T cells. Therefore, to effectively use an adoptive immunotherapy approach in these conditions, the introduced cells would need to be also resistant to the immunosuppressive treatment. Thus, in particular embodiment, the method according to the present invention further comprises a step of modifying T-cells to make them resistant immunosuppressive agent, preferably by inactivating at least one gene encoding a target for an immunosuppressive agent. An immunosuppressive agent is an agent that suppresses immune function by one of several mechanisms of action. In other words, an immunosuppressive agent is a role played by a compound which is exhibited by a capability to diminish the extent of an immune response. The method according to the invention allows conferring immunosuppressive resistance to T cells for immunotherapy by inactivating the target of the immunosuppressive agent in T cells. As non limiting examples, targets for immunosuppressive agent can be a receptor for an immunosuppressive agent such as: CD52, glucocorticoid receptor (GR), a FKBP family gene member and a cyclophilin family gene member. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. Said rare-cutting endonuclease can be a meganuclease, a Zinc finger nuclease or a TALE-nuclease. Preferred TALE-nucleases according to the invention are those recognizing and cleaving the target sequence selected from the group consisting of: SEQ ID NO: 36 to 41 (GR), and SEQ ID NO: 54 to 59 (CD52). Said TALE-nucleases preferably comprise a polypeptide sequence selected from SEQ ID NO: 42 to SEQ ID NO: 53 and SEQ ID NO: 60 to SEQ ID NO: 61.

Suicide Genes

In another aspect, since engineered T-cells can expand and persist for years after administration, it is desirable to include a safety mechanism to allow selective deletion of administrated T-cells. Thus, in some embodiments, the method of the invention can comprises the transformation of said T-cells with a recombinant suicide gene. Said recombinant suicide gene is used to reduce the risk of direct toxicity and/or uncontrolled proliferation of said T-cells once administrated in a subject (Quintarelli C, Vera F, blood 2007; Tey S K, Dotti G., Rooney C M, boil blood marrow transplant 2007). Suicide genes enable selective deletion of transformed cells in vivo. In particular, the suicide gene has the ability to convert a non-toxic pro-drug into cytotoxic drug or to express the toxic gene expression product. In other words, "Suicide gene" is a nucleic acid coding for a product, wherein the product causes cell death by itself or in the presence of other compounds. A representative example of such a suicide gene is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil. Suicide genes also include as non limiting examples caspase-9 or caspase-8 or cytosine deaminase. Caspase-9 can be activated using a specific chemical inducer of dimerization (CID). Suicide genes can also be polypeptides that are expressed at the surface of the cell and can make the cells sensitive to therapeutic monoclonal antibodies. As used herein "prodrug" means any compound useful in the methods of the present invention that can be converted to a toxic product. The prodrug is converted to a toxic product by the gene product of the suicide gene in the method of the present invention. A representative example of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy- 2-fluoro-β-D-arabinofuranosyl)-5-iodouracil], 6-methoxypurine arabinoside for VZV-TK, and 5-fluorocytosine for cytosine deaminase.

Delivery Methods

The different methods described above involve expressing a protein of interest such as drug resistance gene, rare-cutting endonuclease, Chimeric Antigen Receptor (CAR), suicide gene into a cell. As non-limiting example, said protein of interest can be expressed in the cell by its introduction as a transgene preferably encoded by at least one plasmid vector. Polypeptides may be expressed in the cell as a result of the introduction of polynucleotides encoding said polypeptides into the cell. Alternatively, said polypeptides could be produced outside the cell and then introduced thereto. Methods for introducing a polynucleotide construct into cells are known in the art and include as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells. Said plasmid vector can comprise a selection marker which provides for identification and/or selection of cells which received said vector. Different transgenes can be included in one vector. Said vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

In a more preferred embodiment of the invention, polynucleotides encoding polypeptides according to the present invention can be mRNA which is introduced directly into the cells, for example by electroporation. The inventors determined the optimal condition for mRNA electroporation in T-cell. The inventor used the cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, Mass. 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell.

Activation and Expansion of T-Cells

Whether prior to or after genetic modification of the T-cells, the T-cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T-cells can be expanded in vitro or in vivo. Generally, the T cells of the invention are expanded by contact with an agent that stimulates a CD3 TCR complex and a co-stimulatory molecule on the surface of the T-cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell. As non limiting examples, T-cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell.

Conditions appropriate for T-cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, -10, -2, IL-15, TGFp, IL-21 and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics.

Therapeutic Applications

In another embodiment, said isolated T-cells obtained as previously described can be used in allogeneic adoptive cell immunotherapy. In particular, said T-cells according to the present invention can be used for treating cancer, infections or auto-immune disease in a patient in need thereof. In another aspect, the present invention relies on methods for treating patients in need thereof, said method comprising at least one of the following steps:
(a) providing an isolated T-cell obtainable by any one of the methods previously described;
(b) Administrating said cells to said patient.

On one embodiment, said T-cells of the invention can undergo robust in vivo expansion and can persist for an extended amount of time.

Said treatment can be ameliorating, curative or prophylactic. The invention is particularly suited for allogeneic immunotherapy, insofar as it enables the transformation of T-cells, typically obtained from donors, into non-alloreactive cells. This may be done under standard protocols and reproduced as many times as needed. The resulting modified T-cells are administered to one or several patients, being made available as an "off the shelf" therapeutic product.

Cells that can be used with the disclosed methods are described in the previous section. Said treatment can be used to treat patients diagnosed with cancer, viral infection, autoimmune disorders. Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the allogeneic T-cell resistant to drugs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. In an embodiment of the present invention, childhood acute lymphoblastic leukemia (ALL) and amyotrophic myeloma leukemia (AML) diseases are typically treated by allogeneic drug resistant T-cells according to the invention. This can be achieved by using drug resistant KO TRAC CD19$^+$ CAR T-cells and drug resistant KO TRAC CD123$^+$ T-cells respectively.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment is administrated into patients undergoing an immunosuppressive treatment. The present invention preferably relies on cells or population of cells, which have been made resistant to at least one drug agent according to the present invention due to either expression of a drug resistance gene or the inactivation of a drug sensitizing gene. In this aspect, the drug treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, intracranially, by intravenous or intralymphatic injection, or intraperitoneally. In one embodiment, the cell compositions of the present invention are preferably administered by intravenous injection.

The administration of the cells or population of cells can consist of the administration of $10^3$-$10^{10}$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or pharmaceutical composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T-cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T-cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Pharmaceutical Composition

The isolated T-cells of the present invention may be administered either alone, or as a pharmaceutical composition in combination with diluents and/or with other components such as IL-2 or other cytokines or cell populations. Briefly, pharmaceutical compositions of the present invention may comprise T-cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g. aluminum hydroxide); and preservatives. Compositions of the present invention are preferably formulated for intravenous administration. Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Method for Testing Cytoxicity of Isolated CAR T Cells and a Kit for its Use

Another embodiment of the invention encompasses a method for testing cytotoxicity of isolated Chimeric Antigen Receptor (CAR) T cells such as described previously towards drug resistant target cells; both said isolated CAR T cells expressing a Chimeric Antigen Receptor (CAR) and target cells expressing at least a particular surface antigen (and optionally a marker gene such as luciferase), comprising:
 (a) Preparing both said population of T-cells and target cells;
 (b) Incubating said T-cells population with at least said specific target cells;
 (c) Determining the viability rate of said specific target cells.

The resistance gene can be chosen amongst those presented in a precedent section.

Preferably, said resistance gene is dCK.

The surface antigen to be chosen in the present invention is one which can be expressed in T cells by Chimeric Antigen Receptors (CAR), and depends to the cell to be targeted and is usually specific to cancerous cells. Preferably, the surface antigen to be used in the CAR T cell is CD19, as this antigen appears to be expressed specifically in certain lymphomas or leukemias such as acute lymphocytic leukemia (ALL).

Finally, the present invention concerns a kit for performing method for testing cytotoxicity of a CAR T cell with respect to a target cell, comprising:
 (d) Said T cells population endowed with a CAR specific for an antigen;
 (e) Said target cells expressing said antigen;
 (f) Optionally a culture medium;
both T cells and target cells having been made resistant to chemotherapy drugs according to the invention.

The present application does not only seek protection for a general method for engineering T-cells resistant to purine nucleotide analogs (PNA) drugs and 6TG. It is more broadly drawn to methods of obtaining T-cells, which are both resistant to chemotherapy drugs and allogeneic, encompassing at least one of the following objects:
 1) A method of engineering allogeneic and drug resistant T-cells for immunotherapy comprising:
  (a) Providing a T-cell;
  b) Selecting at least one chemotherapy drug, said T-cell is sensitive to;
  (c) Modifying said T-cell by inactivating at least one gene encoding a T-cell receptor (TCR) component;
  (d) Modifying said T-cell to confer drug resistance to said chemotherapy drug;
  (e) Expanding said engineered T-cell, optionally in the presence of said drug.
 2) The method of claim 1 wherein at least one gene encoding a TCR component is inactivated by expressing a rare-cutting endonuclease able to cleave a target sequence within at least one gene encoding a TCR component.
 3) The method of claim 1 or 2 wherein said drug resistance is conferred to the T-cell by inactivating at least one drug sensitizing gene.
 4) The method of claim 3 wherein said drug sensitizing gene is inactivated by expressing a rare-cutting endonuclease able to cleave a target sequence within said drug sensitizing gene.
 5) The method of claim 4 wherein said rare-cutting endonuclease is a TALE-nuclease.
 6) The method of claims 3 to 5 wherein said drug sensitizing gene is dCK.
 7) The method of claim 6 wherein dCK gene is inactivated by TALE-nucleases.
 8) The method of claim 7 wherein TALE-nucleases dCK gene inactivation is performed by using the TALE-nucleases of SEQ ID No 63 and SEQ ID No 64, and the dCK target sequence is SEQ ID No 62.
 9) The method of claims 3 to 5 wherein said drug sensitizing gene is HPRT.
 10) The method of claim 1 wherein said drug resistance is conferred to the T-cell by expressing at least one drug resistance gene.
 11) The method of claim 10 wherein said drug resistance gene is a mutated dihydrofolate reductase (DHFR) protein which confers resistance to an anti-folate treatment, preferably methotrexate (MTX).
 12) The method of claim 11 wherein said mutated DHFR comprises at least one amino acid mutation at position selected from the group consisting of: G15, L22, F31, or F34 in the SEQ ID NO: 14.
 13) The method of claim 12 wherein said mutated DHFR comprises two amino acid mutations in position L22 and F31 in the SEQ ID NO: 14.
 14) The method of claim 10 wherein said drug resistance gene is a mutated inosine-5'-monophosphate deshydrogenase II (IMPDH2) which confers resistance to an IMPDH inhibitor, preferably mycophenolate mofetil (MMF).
 15) The method of claim 14 wherein said mutated IMPDH2 comprises at least one amino acid mutation at position T333 and/or 5351 in SEQ ID NO: 15.
 16) The method of claim 10 wherein said drug resistance gene is a mutated calcineurin (CN) heterodimer a and/or b which confers resistance to calcineurin inhibitor, preferably FK506 and/or CsA.
 17) The method of claim 16 wherein said mutated calcineurin heterodimer a comprises at least one amino acid mutation at position selected from the group consisting of: V314, Y341, M347, T351, W352, L354 and K360 in SEQ ID NO: 16.
 18) The method of claim 17 wherein said mutated calcineurin heterodimer a comprises amino acid mutations at positions: T351 and L354 in SEQ ID NO: 16.
 19) The method of claim 17 wherein said mutated calcineurin heterodimer a comprises amino acid mutations at positions: V314 and Y341 in SEQ ID NO: 17.
 20) The method of claim 16 wherein said mutated calcineurin heteromdimer b comprises at least one amino acid mutation at position selected from the group consisting of: V120, N123, L124 and K125 in SEQ ID NO: 17.
21) The method of claim 20 wherein said mutated calcineurin heterodimer b comprises amino acid mutations in positions: L124 and K125 of SEQ ID NO: 17.
22) The method according to any one of claims 10 to 21 wherein said drug resistance gene is expressed in the T-cell by introducing into the T-cell a transgene encoding said drug resistance gene.
23) The method according to any one of claims 10 to 21 wherein said drug resistance gene is expressed in the T-cell, by introducing into the T-cell a donor matrix which comprises at least one homologous sequence of an endogenous gene and a sequence encoding drug resistance gene such that homologous recombination occurs between endogenous genes and said donor matrix.
24) The method of claim 23 further comprising introducing a rare-cutting endonuclease into the T-cell able to selectively cleave a target sequence within said endogenous gene, such that homologous recombination rate is stimulated.
25) The method according to claim 24, wherein said rare-cutting endonuclease is a TALE-nuclease.
26) The method according to any one of claims 1 to 25 further comprising expressing in the T-cell a Chimeric Antigen Receptor.
27) The method according to any one of claims 1 to 26 said Chimeric Antigen Receptor is CD19+ or CD123+.
28) The Method according to any one of claims 1 to 27 further comprising inactivating an immune-checkpoint gene.
29) The method according to any one of claims 1 to 28, wherein said engineered T-cells are expanded in patient's blood.
30) The method according to any one of claims 1 to 28, wherein said engineered T-cells are expanded in-vitro.
31) The method according to any one of claims 1 to 30, wherein said engineered T-cells are expanded in presence of said drug.
32) An isolated T-cell or cell line obtainable from the method of any one of claims 1 to 31.
33) An isolated T-cell resistant to a drug which comprises at least one disrupted gene encoding a T-cell Receptor component.
34) The isolated T-cell of claim 33 expressing at least one drug resistance gene.
35) The isolated T-cell of claim 33 wherein said drug resistance gene is selected from the group consisting of: ble gene, mcrA gene and genes encoding mutant DHFR, mutant IMPDH2, mutant calcineurin and mutant AGT.
36) The isolated T-cell of claim 33 comprising at least one disrupted drug sensitizing gene, preferably HPRT gene.
37) The isolated T-cell of any one of claims 32 to 36 wherein said isolated T-cell is endowed with a Chimeric Antigen Receptor (CAR) specific for an antigen.
38) The isolated T-cell of claim 37 wherein said CAR target CD19+ cells or CD123+ cells;
39) An isolated T-cell according to any one of claims 32 to 38 for its use as a medicament.
40) An isolated T-cell according to claims 32 to 39 for treating a cancer, an auto-immune condition or an infection by a pathogen.
41) An isolated T-cell according to claim 40 for its use as a treatment of acute lymphoblasic leukemia (ALL) or amyotrophic myeloma leukemia (AML).
42) A pharmaceutical composition comprising at least one isolated T-cell according to any one of claims 32 to 41.
43) A method for treating a patient in need thereof comprising:
(a) Preparing a population of T-cells according to the method of any one of claims 1 to 27;
(b) Administrating said transformed T-cells to said patient.
44) The method according to claim 36 wherein said patient is being treated with said drug used in the method of claims 1 to 31.
45) Method for testing cytotoxicity of isolated Chimeric Antigen Receptor (CAR) T cells according to any one of claims 32 to 41 on drug resistant target cells; both said isolated CAR T cells expressing a Chimeric Antigen Receptor (CAR) and target cells expressing at least a particular surface antigen (and optionally a marker gene such as luciferase), comprising:
(a) Preparing both said population of T-cells and target cells;
(b) Incubating said T-cells population with at least said specific target cells;
(c) Determining the viability rate of said specific target cells.
46) A method of claim 45, wherein the said resistance gene is dCK.
47) A method of claim 44 or claim 45 wherein said surface antigen is CD19.
48) A method of claim 47 wherein said target is CD19+ Luciferase+ Daudi cells.
49) A kit for performing method for testing cytotoxicity of a CAR T cell with respect to a target cell, comprising:
(a) a T cells population endowed with a CAR specific for an antigen;
(b) target cells expressing said antigen;
said both T cells and target cells having been made resistant to a chemotherapy drug.

Definitions

In the description above, a number of terms are used extensively. The following definitions are provided to facilitate understanding of the present embodiments.

Amino acid residues in a polypeptide sequence are designated herein according to the one-letter code, in which, for example, Q means Gln or Glutamine residue, R means Arg or Arginine residue and D means Asp or Aspartic acid residue.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "nucleic acid molecule" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Nucleic acids can be either single stranded or double stranded.

By "gene" is meant the basic unit of heredity, consisting of a segment of DNA arranged in a linear manner along a chromosome, which codes for a specific protein or segment of protein, small RNA and the like. A gene typically includes a promoter, a 5' untranslated region, one or more coding sequences (exons), optionally introns, a 3' untranslated region. The gene may further comprise a terminator, enhancers and/or silencers.

The term "transgene" means a nucleic acid sequence (encoding, e.g. one or more polypeptides), which is partly or entirely heterologous, i.e. foreign, to the host cell into which it is introduced, or, is homologous to an endogenous gene of the host cell into which it is introduced, but which can be designed to be inserted, or can be inserted, into the cell genome in such a way as to alter the genome of the cell into which it is inserted (e.g. it is inserted at a location which differs from that of the natural gene or its insertion results in a knockout). A transgene can include one or more transcriptional regulatory sequences and any other nucleic acid, such as introns, that may be necessary for optimal expression of the selected nucleic acid encoding polypeptide. The polypeptide encoded by the transgene can be either not expressed, or expressed but not biologically active, in cells in which the transgene is inserted.

By "genome" it is meant the entire genetic material contained in a cell such as nuclear genome, chloroplastic genome, mitochondrial genome.

By "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length. The endonuclease according to the present invention recognizes and cleaves nucleic acid at specific polynucleotide sequences, further referred to as "target sequence". The rare-cutting endonuclease can recognize and generate a single- or double-strand break at specific polynucleotides sequences.

In a particular embodiment, said rare-cutting endonuclease according to the present invention can be a Cas9 endonuclease. Indeed, recently a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010). In the present invention, guide RNA can be designed for example to specifically target a gene encoding a TCR component. Following the pairing between the guide RNA and the target sequence, Cas9 induce a cleavage within TCR gene.

Rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

Said rare-cutting endonuclease can be a modular DNA binding nuclease. By modular DNA binding nuclease is meant any fusion proteins comprising at least one catalytic domain of an endonuclease and at least one DNA binding domain or protein specifying a nucleic acid target sequence. The DNA binding domain is generally a RNA or DNA-binding domain formed by an independently folded polypeptide or protein domain that contains at least one motif that recognizes double- or single-stranded polynucleotides. Many such polypeptides have been described in the art having the ability to bind specific nucleic acid sequences. Such binding domains often comprise, as non limiting examples, helix-turn helix domains, leucine zipper domains, winged helix domains, helix-loop-helix domains, HMG-box domains, Immunoglobin domains, B3 domain or engineered zinc finger domain.

According to a preferred embodiment of the invention, the DNA binding domain is derived from a Transcription Activator like Effector (TALE), wherein sequence specificity is driven by a series of 33-35 amino acids repeats originating from *Xanthomonas* or *Ralstonia* bacterial proteins. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base ($T_0$) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence.

Other engineered DNA binding domains are modular base-per-base specific nucleic acid binding domains (MBBBD) (PCT/US2013/051783). Said MBBBD can be engineered, for instance, from the newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011). MBBBD proteins comprise modules of about 31 to 33 amino acids that are base specific. These modules display less than 40% sequence identity with *Xanthomonas* TALE common repeats, whereas they present more polypeptides sequence variability. When they are assembled together, these modular polypeptides can although target specific nucleic acid sequences in a quite similar fashion as *Xanthomonas* TALE-nucleases. According to a preferred embodiment of the present invention, said DNA binding domain is an engineered MBBBD binding domain comprising between 10 and 30 modules, preferably between 16 and 20 modules. The different domains from the above proteins (modules, N and C-terminals) from *Burkholderia* and *Xanthomonas* are useful to engineer new proteins or scaffolds having binding properties to specific nucleic acid sequences. In particular, additional N-terminal and C-terminal domains of engineered MBBBD can be derived from natural TALE like AvrBs3, PthXo1, AvrHah1, PthA, Tal1c as non-limiting examples.

"TALE-nuclease" or "MBBBD-nuclease" refers to engineered proteins resulting from the fusion of a DNA binding domain typically derived from Transcription Activator like Effector proteins (TALE) or MBBBD binding domain, with an endonuclease catalytic domain. Such catalytic domain is preferably a nuclease domain and more preferably a domain having endonuclease activity, like for instance I-TevI, ColE7, NucA and Fok-I. In a particular embodiment, said nuclease is a monomeric TALE-Nuclease or MBBBD-nuclease. A monomeric Nuclease is a nuclease that does not require dimerization for specific recognition and cleavage, such as the fusions of engineered DNA binding domain with the catalytic domain of I-TevI described in WO2012138927. In another particular embodiment, said rare-cutting endonuclease is a dimeric TALE-nuclease or MBBBD-nuclease, preferably comprising a DNA binding domain fused to FokI. TALE-nuclease have been already described and used to stimulate gene targeting and gene modifications (Boch, Scholze et al. 2009; Moscou and Bogdanove 2009; Christian, Cermak et al. 2010). Such engineered TALE-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "chimeric antigen receptor" (CAR) it is meant a chimeric receptor which comprises an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

In a preferred embodiment, said extracellular ligand-binding domain comprises a single chain antibody fragment (scFv) comprising the light ($V_L$) and the heavy ($V_H$) variable fragment of a target antigen specific monoclonal antibody joined by a flexible linker. In a preferred embodiment, said scFV is derived from a CD19 or a CD123 antibody. Preferably, said scFV of the present invention comprises a scFV derived from a CD19 monoclonal antibody 4G7 (Peipp, Saul et al. 2004)

The signal transducing domain or intracellular signaling domain of the CAR according to the present invention is responsible for intracellular signaling following the binding of extracellular ligand binding domain to the target resulting in the activation of the immune cell and immune response. Preferred examples of signal transducing domain for use in a CAR can be the cytoplasmic sequences of the T-cell receptor and co-receptors that act in concert to initiate signal transduction following antigen receptor engagement. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. In particular embodiment the signal transduction domain of the CAR of the present invention comprises a co-stimulatory signal molecule. A co-stimulatory molecule is a cell surface molecule other than an antigen receptor or their ligands that is required for an efficient immune response. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

The CAR according to the present invention is expressed on the surface membrane of the cell. Thus, the CAR can comprise a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can further comprise a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

Downregulation or mutation of target antigens is commonly observed in cancer cells, creating antigen-loss escape variants. Thus, to offset tumor escape and render immune cells more specific to target, the CD19 specific CAR can comprise another extracellular ligand-binding domains, to simultaneously bind different elements in target thereby augmenting immune cell activation and function. Examples of CD19 specific CAR are ScFv FMC63 (Kochenderfer J N, Wilson W H, Janik J E, et al. *Eradication of B-lineage cells and regression of lymphoma in a patient treated with autologous T cells genetically engineered to recognize CD19. Blood* 2010; 116(20):4099-410) or ScFv 4G7 CAR (described in the application filed under the number PCT/EP2014/059662). In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

The terms "vector" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

By "delivery vector" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g. vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non-integrative lentiviral vectors (or NILV)" is meant efficient gene delivery vectors that do not integrate the genome of a target cell through the action of the virus integrase.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO: 8 to SEQ ID NO: 20 and SEQ ID NO: 26 to SEQ ID NO: 35.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated;

<<knockout>> means that the gene is mutated to that extend it cannot be expressed;

"TRAC" refers to "T cell receptor alpha constant>> and corresponds to TCRα subunit constant gene.

In addition to the preceding features, the invention comprises further features which will emerge from the following examples illustrating the method of engineering allogeneic and resistant T-cells for immunotherapy, as well as to the appended drawings.

Example 1: Generation and Characterization of Clofarafine Resistant T Cells

TALE-Nuclease-Mediated Inactivation of dCK

Figure 3:
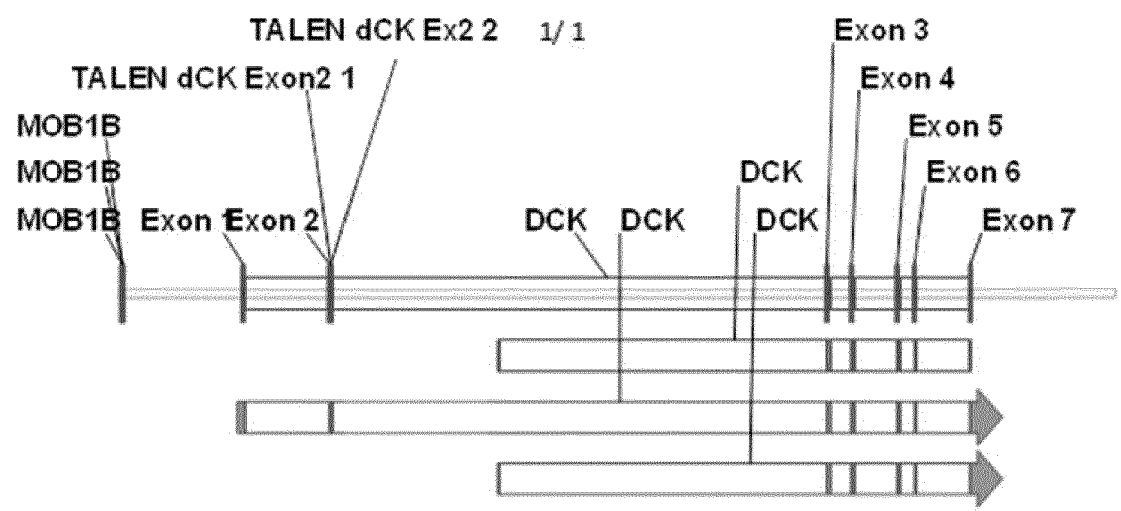
Figure 4:
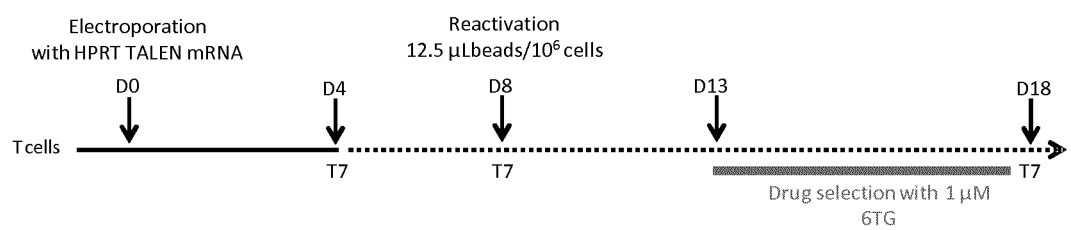

To inactivate dCK, two pairs of dCK TALE-nucleases were designed, assembled and validated by sequencing; subsequent work was performed only with the pair named TALE-nuclease dCK2 and having SEQ ID NO:63 and SEQ ID NO:64. The details regarding the dCK gene overall architecture (exons and introns) and the sequences of TALE-nuclease target sites located in the exon 2 are indicated in FIG. 3.

The dCK target sequence for the TALE-nuclease dCK2 pair corresponds to SEQ ID No 62.

Once validated, mRNAs encoding the two TALE-nucleases were produced, polyadenylated and used to electroporate T cells using pulse agile technology (5 or 10 μg of TALE-nuclease mRNA left and right were used) such as described in the WO 2013/176915. A cold temperature shock was performed by incubating T cells at 30° C. immediately after electroporation and for 24 hours. A reactivation (12.5 μl beads/$10^6$ cells) was performed at D8 (8 days after the electroporation).

The resulting T cells were allowed to grow and eventually characterized genotypically (by Endo T7 assay and deep sequencing at dCK and TRAC loci) as well as phenotypically. Their phenotypical characterization consisted of (i), checking their ability to grow in the presence or absence of drug (ii), determining the $IC_{50}$ of PNAs, clofarabine and fludarabine, toward T cells and (iii), determining the extent of TRAC inactivation by FACS analysis when double KO is performed.

Genotypic Characterization of dCK KO T Cells

Figure 5:
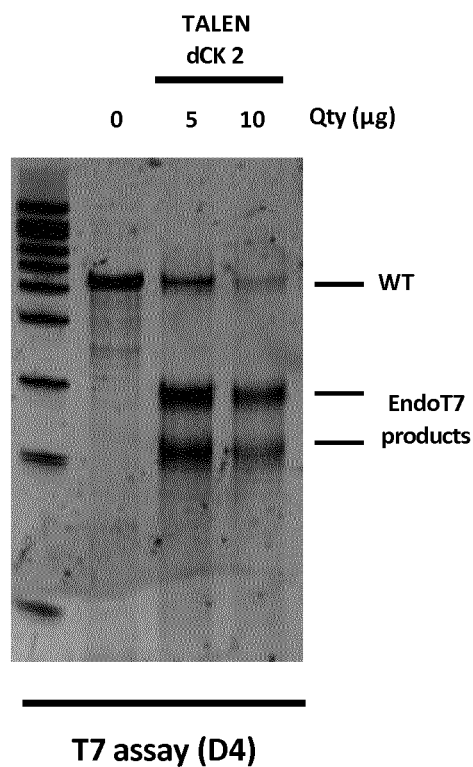

To assess the efficiency of dCK gene inactivation, cells transfected with either 5 or 10 μg of TALE-nuclease mRNA were grown for 4 days (D4, 4 days after electroporation) and collected to perform T7 assays at the dCK locus (FIG. 5).

The sequences for the primers used in these T7 assays correspond to the SEQ ID No 68 and SEQ ID No 69. The T7 assay protocol is described in Reyon, D., Tsai, S. Q., Khayter, C., Foden, J. A., Sander, J. D., and Joung, J. K. (2012) FLASH assembly of TALE-nucleases for high-throughput genome editing. *Nat Biotechnologies*.

The results from this endo T7 assay show that, when 5 and 10 μg of left and right dCK2 TALE-nuclease were transfected, significant gene processing indicating that dCK is efficiently inactivated.

Determination of Growth Rate of dCK KO T Cells

Figure 6:
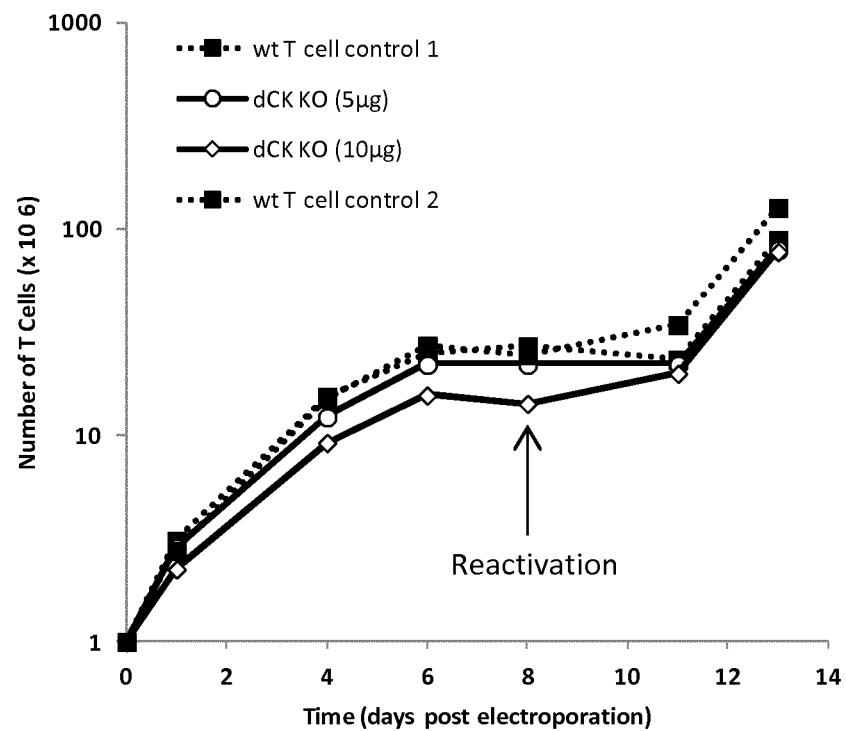

As presented in FIG. 6, dCK KO cells display similar growth rate with respect to WT cells. In addition, they could be reactivated at D8 with the same efficiency than WT T cells.

Selection of dCK KO T Cell in the Presence of Clofarabine dCK KO or WT T cells were allowed to grow from D8 to D13 and then incubated with or without 1 μM clofarabine until D18. Cells were collected at D8 (before drug addition) and at D18 (after drug incubation) and were used to perform an endo T7 assay.

Figure 7:
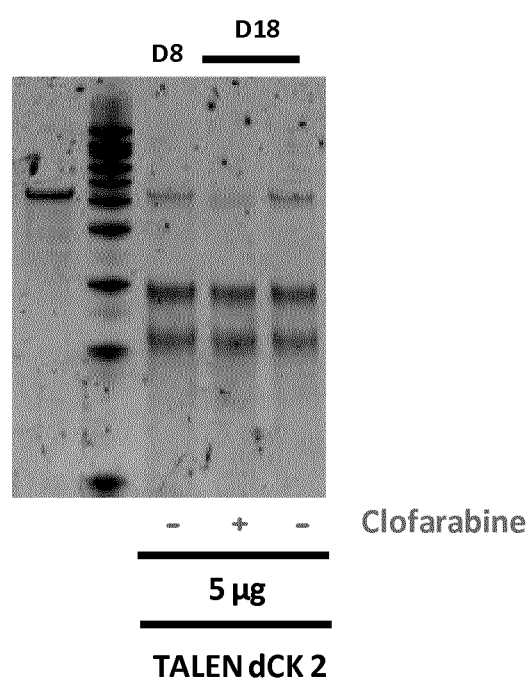
FIG. 7 represents the endo T7 assay performed at Day 8 (D8) to check the dCK inactivation in T cells (by using 5 µg of TALE-nuclease dCK 2 pair) in the presence of 1 µM clofarabine (+) or in the absence of clofarabine (−)

The results presented in FIG. 7 show that the presence of 1 µM clofarabine in the media at D18, selectively enriched dCK KO T cells when compared to the WT T-cell (2 bands of lower molecular weight for the dCK KO T-cell compared to a single band of higher molecular weight for the WT T-cells). This indicated that TALE-nuclease-mediated inactivation of dCK allows selection of drug resistant T cells over WT T cells. Thus, dCK KO T cells are able to resist to the presence of 1 µM clofarabine which corresponds to a clinically relevant dose for the treatment of acute lymphoblastic leukemia (ALL) according to the $C_{max}$ reported by European Medecines Agency (EMA).

Determination of IC50 for Clofarabine on dCK KO T Cells Versus WT T Cells

To further investigate the ability of T cells to resist to clofarabine, IC50 for this drug was determined on dCK KO and WT T cells. The cells were collected 3 days after transfection were incubated for 2 days in the presence of increasing concentration of clofarabine (0 to 10 µM). At the end of clofarabine incubation, viability of T cells was determined by FACS analysis2.

Figure 8:
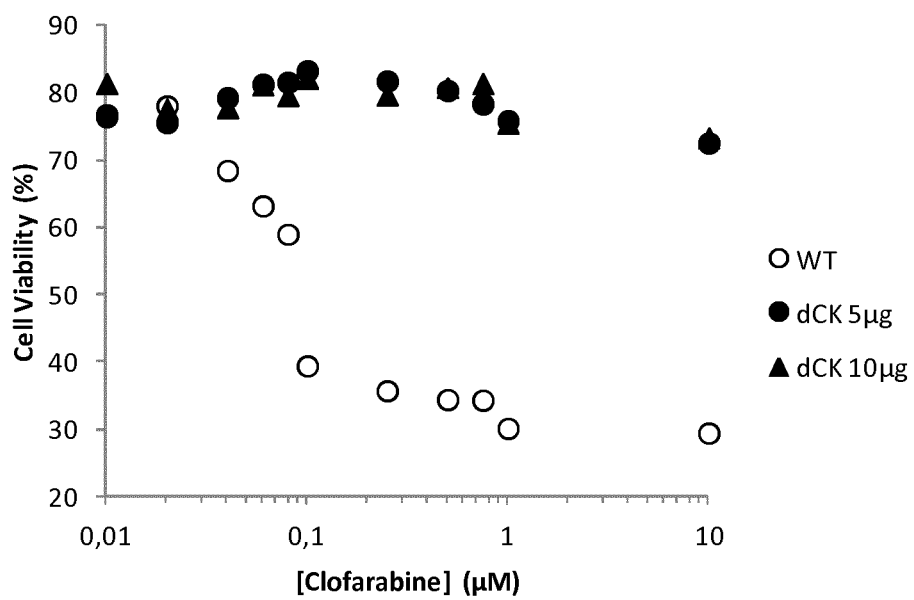
FIG. 8 represents the percentage of cell viability of WT and dCK KO T cells (treated with 5 µg or 10 µg of mRNA encoding dCK2 TALE-nuclease pair) cultured for two days in the presence of increasing amount of clofarabine (10 nM to 10 µM). This graph allows to determine the Clofarabine IC50 toward both cell populations.

The results presented in FIG. 8 show clearly that the processing of dCK gene mediated by TALE-nucleases efficiently inactivates dCK activity in T cells. Such inactivation correlates to clofarabine resistance, contrasting with the sensitivity of WT T cells. The IC50 values (amount of drug to add in the media to decrease cell viability to 50%) correspond respectively to about 100 nM and 10 µM for WT and dCK KO T cells.

Altogether, this first set of data allows to conclude that TALE-nuclease-mediated inactivation of dCK gene is efficient. Inactivation of dCK doesn't impair the growth rate of engineered T cells while enabling them to resist to clinically relevant dose of clofarabine.

Figure 9:
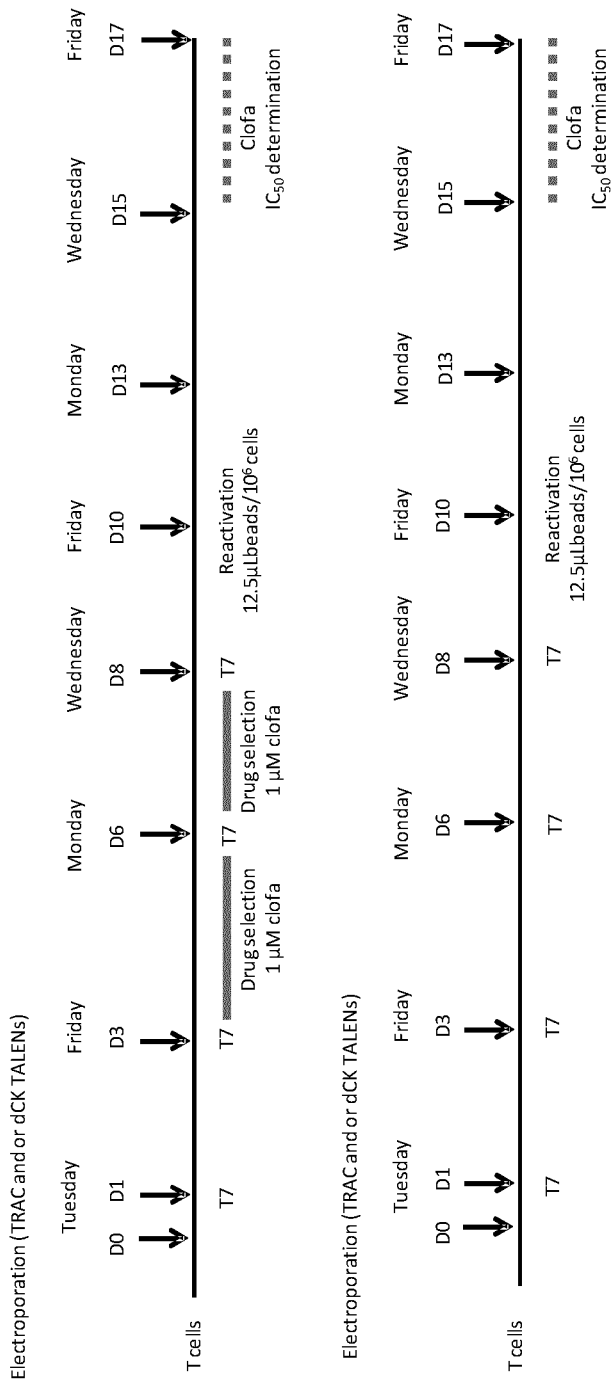
FIG. 9 shows the 2 workflows used to generate and characterize clofarabine resistant allogeneic T cells; the upper one corresponds to the case when a drug selection was performed in constrast to the lower one when no drug selection was done; Day 0 (D0) is the day when the double electroporation by TRAC and dCK TALE-nucleases was realized.

Example 2: Generation and Characterization of Clofarabine Resistant Allogeneic T Cells To develop and manufacture clofarabine resistant allogeneic CAR T cells, dCK and TRAC genes are inactivated simultaneously. After having demonstrated in Example 1 that dCK inactivation was successful, TRAC/dCK double KO T cells were generated and characterized. Two workflows presented in FIG. 9 were followed in parallel. One of them corresponds to a period of 5 days incubation of cells in the presence of clofarabine.

Genotypic Characterization

To first assess the efficiency as well as the kinetic of TRAC and/or dCK gene inactivations, transfected cells were grown for 6 days and collected at D1, D3 and D6 to perform T7 assays at the dCK and TRAC loci. To achieve that, 2 pairs primers having respectively SEQ ID No 68 and No 69; and SEQ ID No 70 and No 71 were used in the T7 assays for the dCK and TRAC loci.

The protocol used in the one described in Reyon, D., Tsai, S. Q., Khayter, C., Foden, J. A., Sander, J. D., and Joung, J. K. (2012) FLASH assembly of TALE-nucleases for high-throughput genome editing. *Nat Biotechnol*

The results presented in FIG. 10 show that TALE-nuclease-mediated single TRAC and dCK KO are highly efficient even at D1. Even though double KO cells couldn't have been characterized as homogeneous population, it appears that the TRAC/dCK double KO is also highly efficient.

The cells were then grown in the presence or in the absence of 1 µM clofarabine. At D6 (six days after the transfection) and after 3 days of culture in the presence or in the absence of clofarabine, cells were collected and dCK KO efficiency was determined by endo T7 assay and high throughput DNA sequencing.

The protocol used for deep sequencing is described in Shendure, J., & Ji, H. (2008). Next-generation DNA sequencing. *Nature biotechnology*, 26(10), 1135-1145.

The results presented in FIG. 11 show that the frequency of indels generated at the dCK locus is around 80-90% in all the experiments. This indicated once again that TALE-nuclease-mediated inactivation of dCK is highly efficient, even when it is combined with a simultaneous TRAC inactivation. The presence of 1 µM clofarabine in the culture media for 5 days does not increase the dCK KO-specific T7 band as seen in the first set of experiments. This suggested that in this particular experiment, dCK inactivation was successful enough to allow engineered T cells to grow in the presence of clofarabine. Interestingly, this indicated that if dCK KO is efficient enough, there is no need to select T cells in the presence of clofarabine to get drug resistant T cells. Therefore, this feature represents a clear advantage in the manufacturing of drug resistant allogeneic T cells.

Phenotypic Assessment of TCAR KO Efficiency

TRAC KO T cells collected from for the double KO experiment were analysed and purified by FACS (CliniMACS). The results presented in FIG. 12A show labeling experiment of T cells with or without of anti TCR mAb-PE. FIG. 12B relates also to mAb-PE labeling of T-cell in media with or without clofarabine, before and after TRAC KO T cells purification.

The results show that the efficiency of TCR KO is high (around 85%) in T cells treated with TRAC and dCK mRNA (dCK/TRAC double knock out). The method of purification allows for efficient selection/purification of TCR negative cells up to 99.3% of purity.

Phenotypic Characterization of TRAC/dCK KO T Cells

Growth rate of T-cells in the absence of clofarabine is shown in FIG. 13. Even if KO dCK T display a slight growth defect, these could be reactivated at D10 with the same efficiency than WT T cells.

Growth rate of T-cells in the presence of Clofarabine is shown in FIG. 14. This experiment was performed on double KO dCK/TCAR T CAR T-cells (FMC63 which is described in patent application having the filing number PCT/EP2014/059662.) by culturing these cells during 11 days in media having different clofarabine (from 0.1 µM to 10 µM). The results presented in FIG. 14 show clearly that cell expansion for the double KO dCK/TCAR CAR T-cells is correct up to the 1 µM clofarabine (which corresponds to Cmax), even if the growth less marked than that of these cells without drug.

Determination of IC50 for Clofarabine on Engineered T Cells Versus WT T-Cells

To further investigate the ability of double KO T cells to handle clofarabine, IC50 for this drug was determined. T cells were grown with or without clofarabine between D3 and D8 (see workflow 2 in FIG. 9), then they were incubated for 2 days (from D15 to D17) in media with different concentrations of clofarabine. T cells viability was then assessed by FACS analysis using the count bright kit.

The results presented FIG. 15 show that dCK and dCK/TRAC KO T cells display a significant ability to resist to clofarabine compared to negative control T cells and to TRAC simple KO T cells. Noteworthy, cells selection by using 1 µM clofarabine for 5 days between D3 and D8 (see workflow 2 in FIG. 9) doesn't improve their capacity to resist to clofarabine. This suggests that the dCK inactivation is efficient enough and that the 5 days incubation for drug selection is not needed to obtain clofarabine resistant allogeneic CAR T cells.

Cytotoxicity of Drug Resistant Allogeneic CAR T Cells

The cytotoxicity assay was performed as follows: 10 CAR T cells (FMC63, see above for the reference) were incubated with DAUDI cells (specific targets) and K562 cells (non specific targets) for 5 hours. Cells were then collected and viability of DAUDI and K562 cells were determinated by calculating the frequency of targeted cell lysis.

The results presented in FIG. 16 show that dCK/TRAC double KO CAR T cells display similar targeted cytotoxicity than WT CAR T cells (35% of targeted cytotoxicity). This indicated that inactivation of dCK and TRAC genes do not influence the cytotoxicity of CAR FMC63 T cells.

These cells were then used to determined their sensitivity for clofarabine and fludarabine as performed before. The results presented in FIG. 17 show that dCK/TRAC KO CAR T cells have a significant ability to resist to clofarabine compared to CAR T cells negative control ($IC_{50}$=500 nM and 0.1 nM respectively). Similar results were obtained with fludarabine ($IC_{50}$=400 µM and 10 µM for double KO CAR T cells and T CAR respectively).

Conclusions

Altogether, these experiments show that a simultaneous inactivation of dCK and TRAC genes is highly efficient and allows to generate more than 70% of double KO T cells with a single round of electroporation. Interestingly, due to this high efficiency, there is no need for time consuming selection step. Engineered T cells display marked capacity to resist to clofarabine and remained at their maximum of viability under the pressure of clinically relevant clofarabine dose.

Example 3: Generation of Clofarabine-Resistant Daudi Cells

The objective is to prepare drug resistant $CD19^+/Luc^+$ Daudi target cells to assess the cytotoxicity of clofarabine resistant allogeneic CAR T cells.

Genotypic Characterization of dCK KO Daudi Cells dCK TALE-nuclease mRNA were prepared and Daudi cells were electroporated by dCK TALE-nuclease mRNA according to the protocols described in the WO2013/176915.

An endo T7 assay has been performed to assess dCK KO efficiency such as in Example 1. The analysis was performed 2 days post transfection. The primers have SEQ ID No 68 and No 69.

The results presented in FIG. 18 show a high inactivation of dCK gene.

Phenotypic Characterization of dCK KO Daudi Cells

Daudi cells were cultured in media having different concentrations of clofarabine (0; 0.1; 0.25; 0.5 and 1 µM) for several days and counted at each passage.

The results presented in FIG. 19 show that dCK KO Daudi cells were able to grow in the presence of up to 1 µM clofarabine. Their growth rate was similar to the one of WT T cells grown in the absence of clofarabine suggesting that dCK inactivation doesn't impair the ability of Daudi to grow. As expected, WT Daudi cells growth was clearly impaired. This results demonstrate that dCK $KO-CD19^+$-$Luc^+$-$GFP^+$ cells were successfully generated.

Example 4: Generation and Characterization of 6TG Resistant T Cells

To develop 6MP and 6TG resistant T cells (HPRT KO T cells), HPRT gene was TALE-nuclease-mediated inactivated as follows. Overall HPRT gene architecture (exons and introns) and location of different TALE-nuclease target sites are shown in FIG. 20.

TALE-Nuclease-Mediated Inactivation of HPRT Gene

The workflow used in this experiment to generate and characterize HPRT single KO T cells is reported in FIG. 21. To inactivate the HPRT gene, 2 pairs of HPRT TALE-nucleases was designed, assembled and validated by sequencing (for HPRT 1: SEQ ID No 74 and SEQ ID No 75; for HPRT2: SEQ ID No 77 and SEQ ID No 78). The details regarding the HPRT gene overall architecture (exons and introns) and the location of TALE-nuclease target sites are indicated in FIG. 20. The target sequences for HPRT1 and HPRT2 TALE-nucleases pairs correspond to SEQ ID No 76 and SEQ ID No 79 respectively.

Genotypic Characterization of HPRT KO T Cells

HPRT KO T cells were genotypically characterized at D4 by an endo T7 assay showing HPRT gene inactivation in T cells. The pair of primers used in this assay have SEQ ID No 72 and SEQ ID No 73. The results presented in FIG. 22 show that the pair of HPRT TALE-nucleases was able to highly efficiently process HPRT gene.

Growth Rate of HPRT KO T Cells

According to the results presented in FIG. 23, KO HPRT cells show a growth rate similar to WT T cells despite a bit lower for the TALE-nuclease HPRT2 pair (performed with 10 µg of TALE-nuclease). Nevertheless, T cells inactivated by 10 µg of TALE-nuclease HPRT2 pair were reactivated at D10 with the same efficiency than WT T cells, indicating that HPRT inactivation doesn't significantly impair T cells growth. The TALE-nuclease HPRT1 pair was chosen in the following experiments.

Selection of HPRT KO T Cells in the Presence of 6TG

HPRT KO or WT T cells were allowed to grow from D8 to D13 and then incubated in the presence or in the absence of 1 µM 6TG until D18 (workflow shown in FIG. 22). Cells were collected at D8 (before drug addition) and at D18 (after drug incubation) and were used to perform an endo T7 assay. The pair of primers used have the sequences SEQ ID No 72 and SEQ ID No 73. The results presented in FIG. 24 show that the presence of 1 µM 6TG in the media allows the selective enrichment of HPRT KO T cells (as seen by the less dense WT band in the presence of 6TG at D18).

Generation of HPRT KO CAR T Cells

To investigate the influence of HPRT inactivation on cytotoxic activity of CAR T cells, T cells transduced with CAR 4G7 lentiviral vector (such as described in the application filed under the number PCT/EP2014/059662) were electroporated with TALE-nuclease HPRT1 encoding mRNA. All the experiments described below were performed with engineered T cells generated without any 6TG selection. The efficiency of HPRT processing was assessed by endo T7 assay. The pair of primers used for this assay correspond to SEQ ID No 72 and SEQ ID No 73. The results presented in FIG. 25 show that HPRT gene was successfully inactivated in the presence or in the absence of CAR 4G7. A better inactivation of HPRT is obtained in T cells than in CAR T cells.

Cytotoxic Properties of HPRT KO CAR-T Cells to Daudi Cells

The cytotoxicity assay was performed as schematically represented in FIG. 27. A set of 10 CAR T cells are incubated during 5 hours with Daudi cells (specific targets) and K562 cells (non specific targets). Cells are then collected and viability of Daudi and K562 cells were determinated for calculating the frequency of targeted cell lysis. The results presented in FIG. 26 show that HPRT KO CAR T cells have a targeted cytotoxicity similar to that of WT CAR T cells. This indicates that the inactivation of HPRT gene does not influence the cytotoxicity of CAR 4G7 T cells.

Determination of IC50 for 6TG on Engineered T Cells Versus WT T Cells

The results presented in FIG. 27 show that processing of HPRT gene (as seen earlier by T7 assay) efficiently inactivates HPRT activity in T cells. Such inactivation confers 6TG resistance that contrasts with the sensitivity of WT T cells to this drug. IC50 can be approximately determined to 10 nM and >100 µM for WT and HPRT KO T cells respectively.

Conclusion

Altogether, these results show that the inactivation of HPRT gene is efficient. Such inactivation enables T cells to resist to high dose of 6TG without the need to purify by a time consuming process. It is shown also that HPRT inactivation can be performed in CAR T cell to a slightly lower extent. Such inactivation doesn't impair the cytotoxic properties of CAR T cells to Daudi cells.

REFERENCES

Bardenheuer, W., K. Lehmberg, et al. (2005). "Resistance to cytarabine and gemcitabine and in vitro selection of transduced cells after retroviral expression of cytidine deaminase in human hematopoietic progenitor cells." *Leukemia* 19(12): 2281-8.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boch, J., H. Scholze, et al. (2009). "Breaking the code of DNA binding specificity of TAL-type III effectors." *Science* 326(5959): 1509-12.

Brewin, J., C. Mancao, et al. (2009). "Generation of EBV-specific cytotoxic T cells that are resistant to calcineurin inhibitors for the treatment of posttransplantation lymphoproliferative disease." *Blood* 114(23): 4792-803.

Cermak, T., E. L. Doyle, et al. (2011). "Efficient design and assembly of custom TALEN and other TAL effector-based constructs for DNA targeting." *Nucleic Acids Res* 39(12): e82.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339(6121): 819-23.

Critchlow, S. E. and S. P. Jackson (1998). "DNA end-joining: from yeast to man." *Trends Biochem Sci* 23(10): 394-8.

Dasgupta, A., D. McCarty, et al. (2011). "Engineered drug-resistant immunocompetent cells enhance tumor cell killing during a chemotherapy challenge." *Biochem Biophys Res Commun* 391(1): 170-5.

Deltcheva, E., K. Chylinski, et al. (2011). "CRISPR RNA maturation by trans-encoded small RNA and host factor RNase III." *Nature* 471(7340): 602-7.

Deng, D., C. Yan, et al. (2012). "Structural basis for sequence-specific recognition of DNA by TAL effectors." *Science* 335(6069): 720-3.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Geissler, R., H. Scholze, et al. (2011). "Transcriptional activators of human genes with programmable DNA-specificity." *PLoS One* 6(5): e19509.

Hacke, K., J. A. Treger, et al. (2013). "Genetic modification of mouse bone marrow by lentiviral vector-mediated delivery of hypoxanthine-Guanine phosphoribosyltransferase short hairpin RNA confers chemoprotection against 6-thioguanine cytotoxicity." *Transplant Proc* 45(5): 2040-4.

Huang, P., A. Xiao, et al. (2011). "Heritable gene targeting in zebrafish using customized TALENs." *Nat Biotechnol* 29(8): 699-700.

Ikehara, Y., S. K. Ikehara, et al. (2004). "Negative regulation of T cell receptor signaling by Siglec-7 (p70/AIRM) and Siglec-9." *J Biol Chem* 279(41): 43117-25.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Jonnalagadda, M., C. E. Brown, et al. (2013). "Engineering human T cells for resistance to methotrexate and mycophenolate mofetil as an in vivo cell selection strategy." *PLoS One* 8(6): e65519.

Kushman, M. E., S. L. Kabler, et al. (2007). "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1." *Carcinogenesis* 28(1): 207-14.

Lackner, G., N. Moebius, et al. (2011). "Complete genome sequence of *Burkholderia rhizoxinica*, an Endosymbiont of *Rhizopus microsporus*." *J Bacteriol* 193(3): 783-4.

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "Modularly assembled designer TAL effector nucleases for targeted gene knock-out and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mahfouz, M. M., L. Li, et al. (2012). "Targeted transcriptional repression using a chimeric TALE-SRDX repressor protein." *Plant Mol Biol* 78(3): 311-21.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

*Mali*, P., L. Yang, et al. (2013). "RNA-guided human genome engineering via Cas9." *Science* 339(6121): 823-6.

Maze, R., C. Kurpad, et al. (1999). "Retroviral-mediated expression of the P140A, but not P140A/G156A, mutant form of 06-methylguanine DNA methyltransferase protects hematopoietic cells against 06-benzylguanine sensitization to chloroethylnitrosourea treatment." *J Pharmacol Exp Ther* 290(3): 1467-74.

Meyaard, L., G. J. Adema, et al. (1997). "LAIR-1, a novel inhibitory receptor expressed on human mononuclear leukocytes." *Immunity* 7(2): 283-90.

Miller, J. C., S. Tan, et al. (2011). "A TALE nuclease architecture for efficient genome editing." *Nat Biotechnol* 29(2): 143-8.

Morbitzer, R., P. Romer, et al. (2011). "Regulation of selected genome loci using de novo-engineered transcription activator-like effector (TALE)-type transcription factors." *Proc Natl Acad Sci USA* 107(50): 21617-22.

Moscou, M. J. and A. J. Bogdanove (2009). "A simple cipher governs DNA recognition by TAL effectors." *Science* 326(5959): 1501.

Mussolino, C., R. Morbitzer, et al. (2011). "A novel TALE nuclease scaffold enables high genome editing activity in combination with low toxicity." *Nucleic Acids Res* 39(21): 9283-93.

Nicoll, G., J. Ni, et al. (1999). "Identification and characterization of a novel siglec, siglec-7, expressed by human natural killer cells and monocytes." *J Biol Chem* 274(48): 34089-95.

Nivens, M. C., T. Felder, et al. (2004). "Engineered resistance to camptothecin and antifolates by retroviral coexpression of tyrosyl DNA phosphodiesterase-I and thymidylate synthase." *Cancer Chemother Pharmacol* 53(2): 107-15.

Park, T. S., S. A. Rosenberg, et al. (2011). "Treating cancer with genetically engineered T cells." *Trends Biotechnol* 29(11): 550-7.

Quigley, M., F. Pereyra, et al. (2010). "Transcriptional analysis of HIV-specific CD8+ T cells shows that PD-1 inhibits T cell function by upregulating BATE." *Nat Med* 16(10): 1147-51.

Sander, J. D., L. Cade, et al. (2011). "Targeted gene disruption in somatic zebrafish cells using engineered TALENs." *Nat Biotechnol* 29(8): 697-8.

Sangiolo, D., M. Lesnikova, et al. (2007). "Lentiviral vector conferring resistance to mycophenolate mofetil and sensitivity to ganciclovir for in vivo T-cell selection." *Gene Ther* 14(21): 1549-54.

Schweitzer, B. I., A. P. Dicker, et al. (1990). "Dihydrofolate reductase as a therapeutic target." *Faseb J* 4(8): 2441-52.

Sorek, R., C. M. Lawrence, et al. (2013). "CRISPR-mediated Adaptive Immune Systems in Bacteria and Archaea." *Annu Rev Biochem.*

Stoddard, B. L. (2005). "Homing endonuclease structure and function." *Q Rev Biophys* 38(1): 49-95.

Sugimoto, Y., S. Tsukahara, et al. (2003). "Drug-selected co-expression of P-glycoprotein and gp91 in vivo from an MDR1-bicistronic retrovirus vector Ha-MDR-IRES-gp91." *J Gene Med* 5(5): 366-76.

Takebe, N., S. C. Zhao, et al. (2001). "Generation of dual resistance to 4-hydroperoxycyclophosphamide and methotrexate by retroviral transfer of the human aldehyde dehydrogenase class 1 gene and a mutated dihydrofolate reductase gene." *Mol Ther* 3(1): 88-96.

Tesson, L., C. Usal, et al. (2011). "Knockout rats generated by embryo microinjection of TALENs." *Nat Biotechnol* 29(8): 695-6.

Weber, E., R. Gruetzner, et al. (2011). "Assembly of designer TAL effectors by Golden Gate cloning." *PLoS One* 6(5): e19722.

Yam, P., M. Jensen, et al. (2006). "Ex vivo selection and expansion of cells based on expression of a mutated inosine monophosphate dehydrogenase 2 after HIV vector transduction: effects on lymphocytes, monocytes, and CD34+ stem cells." *Mol Ther* 14(2): 236-44.

Zhang, F., L. Cong, et al. (2011). "Efficient construction of sequence-specific TAL effectors for modulating mammalian transcription." *Nat Biotechnol* 29(2): 149-53.

Zhang, J. Q., G. Nicoll, et al. (2000). "Siglec-9, a novel sialic acid binding member of the immunoglobulin superfamily expressed broadly on human blood leukocytes." *J Biol Chem* 275(29): 22121-6.

Zielske, S. P., J. S. Reese, et al. (2003). "In vivo selection of MGMT(P140K) lentivirus-transduced human NOD/SCID repopulating cells without pretransplant irradiation conditioning." *J Clin Invest* 112(10): 1561-70.

The invention claimed is:

1. A method of producing ex-vivo immune cells that are resistant to a purine analogue drug, comprising:
   (a) providing an immune cell;
   (b) transfecting said immune cell with a nucleic acid sequence encoding a rare-cutting endonuclease specifically targeting a gene expressing an enzyme having deoxycytidine kinase activity (dcK—EC 2.7.1.74), wherein said rare-cutting endonuclease is a CRISPR/Cas9 nuclease or a TALE-nuclease;
   (c) expressing said endonuclease in said immune cells to obtain targeted inactivation of said dcK gene; and
   (d) expanding the engineered immune cells obtained in step c).

2. The method of claim 1, wherein the immune cells are primary cells.

3. The method of claim 2, wherein the immune cells are T-cells.

4. The method of claim 3, wherein the immune cells are TIL (Tumor Infiltrating Cells).

5. The method of claim 1, wherein the immune cells originate from a patient diagnosed with cancer.

6. The method according to claim 1, wherein the immune cells are further inactivated in their genes encoding TCRalpha or TCRbeta, to make them allogeneic.

7. The method according to claim 1, wherein the rare-cutting endonuclease is a TALE-nuclease.

8. The method according to claim 3, further comprising expressing in the T-cell a Chimeric Antigen Receptor.

9. The method according to claim 1, further comprising inactivating an immune-checkpoint gene.

10. An isolated T-cell resistant to a purine analogue, wherein the T-cell comprises at least one disrupted gene encoding a T-cell Receptor component; wherein the T-cell has the drug sensitizing gene dCK inactivated by using a rare cutting endonuclease,
   wherein said rare-cutting endonuclease is a CRISPR/Cas9 nuclease or a TALE-nuclease and the T-cell is endowed with a Chimeric Antigen Receptor (CAR) specific for an antigen.

11. The isolated T-cell of claim 10, wherein the TCR inactivation is by use of a CRISPR/Cas9 nuclease or a TALE-nuclease.

12. An isolated T-cell of claim 11, wherein the rare-cutting endonuclease is a TALE-nuclease.

13. A pharmaceutical composition comprising at least one isolated T-cell according to claim 10.

14. A method for treating a patient with leukemia or lymphoma comprising:
   (a) preparing a population of T-cells according to claim 10; and
   (b) administering the T-cells to the patient.

15. The method for treating a patient according to claim 14, further comprising administering a purine analog drug to the patient.

16. A population of T cells, which has a frequency of indels generated by using a rare-cutting endonuclease at the dCK locus higher than 80%, wherein said rare-cutting endonuclease is a CRISPR/Cas9 nuclease or a TALE-nuclease, and has at least one feature selected from: (a) the population is resistant to a dose of clofarabine of at least 1 µM, (b) the population is resistant to a dose of fludarabine of at least 100 µM, (c) the population has an IC50 for clofarabine of at least 10 µM, and (d) the population has an IC50 for fludarabine of at least 400 µM.

17. The method according to claim 1, wherein the rare-cutting endonuclease is a CRISPR/Cas9 nuclease.

* * * * *